(12) United States Patent
Levine

(10) Patent No.: US 7,135,303 B2
(45) Date of Patent: Nov. 14, 2006

(54) REGULATORS OF TYPE-1 TUMOR NECROSIS FACTOR RECEPTOR AND OTHER CYTOKINE RECEPTOR SHEDDING

(75) Inventor: Stewart Levine, North Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 541 days.

(21) Appl. No.: 10/220,443

(22) PCT Filed: Feb. 28, 2001

(86) PCT No.: PCT/US01/06464

§ 371 (c)(1),
(2), (4) Date: Dec. 19, 2002

(87) PCT Pub. No.: WO01/64856

PCT Pub. Date: Sep. 7, 2001

(65) Prior Publication Data

US 2003/0215820 A1    Nov. 20, 2003

Related U.S. Application Data

(60) Provisional application No. 60/185,586, filed on Feb. 28, 2000.

(51) Int. Cl.
G01N 33/53 (2006.01)
C12Q 1/68 (2006.01)
C12P 21/02 (2006.01)
A61K 48/00 (2006.01)
C12N 5/06 (2006.01)

(52) U.S. Cl. ............................ 435/7.72; 6/7.1; 6/69.1; 6/320.1; 6/325; 514/44; 530/350; 536/23.5

(58) Field of Classification Search .................. None
See application file for complete search history.

(56) References Cited

U.S. PATENT DOCUMENTS 5,972,680 A * 10/1999 Knowles et al. ............ 435/219

FOREIGN PATENT DOCUMENTS

| DE | 12 48 204 B | 8/1967 |
|---|---|---|
| EP | 0 657 536 A1 | 6/1995 |
| WO | WO 98 20140 A1 | 5/1998 |
| WO | WO 99 58559 A2 | 11/1999 |
| WO | WO 99 63088 A2 | 12/1999 |
| WO | WO 00 32221 A2 | 6/2000 |
| WO | WO 00 73454 A1 | 12/2000 |
| WO | WO 00 75375 A1 | 12/2000 |

OTHER PUBLICATIONS

Fitzgerald et al. The Cytokines Facts Book (2$^{nd}$ edition); San Diego: Academic Press, 2001, pp. 21-28.*
Thomas (Ed). Tabers Cyclopedic Medical Dictionary (15$^{th}$ edition); Philadelphia: F.A. Davis Company, 1985, p. 870.*
Cui et al., Database' Em_Hum [Online] EBML; Feb. 16, 2000, Accession No. AF222340.
Garcia-Alvarez et al., *Eur. J. Biochem.*, 202, 993-1002 (1991).
Hattori et al., *J. Biochem.*, 125(5), 931-938 (1999).
Hirokawa et al., *Bioinform.*, 14(4), 378-379 (1998).
Hofmann et al., *Biol. Chem. Hoppe-Seyler* 374, 166 (1993).
Keller et al., *J. Biol. Chem.*, 270(40), 23612-23618 (1995).
Kyte et al., *J. Mol. Biol.*, 157, 105-132 (1982).
Levine et al., *Am. J. Respir.Cell Mol. Biol.*, 12(2), 196-204 (1995).
Li et al., *Genomics*, 17, 657-664 (1993).
McGuffin et al., *Bioinform.*, 16(4), 404-405 (2000).
Nanus et al., *Proc. Natl. Acad. Sci, USA*, 90, 7069-7073 (1993).
Olsen et al., *FEBS Lett.*, 238(2), 307-314 (1988).
Persson et al., *J. Mol. Biol.* 237, 182-192 (1994).
Rogi et al., *J. Biol. Chem*, 271(1), 56-61 (1996).
Schauder et al., *Proc. Natl. Acad. Sci. USA*, 91, 9534-9538 (1994).
Tan et al., *FEBS Lett.*, 306(1), 9-16 (1992).
Tobler et al., *J. Neurochem*, 68(3), 889-897 (1997).
von Heijne, *J. Mol. Biol.*, 225, 487-494 (1992).
Wilson et al., *Nature*, 368, 32-38 (1994).
*Zinc Metalloproteases in Health and Disease*, Taylor & Francis, London, England (1996), Hooper, p. 1-21, and Wang and Cooper, p. 131-151.

* cited by examiner

*Primary Examiner*—Janet L. Andres
*Assistant Examiner*—Gregory S Emch
(74) *Attorney, Agent, or Firm*—Leydig, Voit & Mayer, Ltd

(57) ABSTRACT

The present invention provides compositions and methods for the regulation of cytokine signaling through the Tumor Necrosis Factor (TNF) pathway. Specifically, the invention provides a novel gene, polypeptide and related compositions and methods for the regulation of ectodomain shedding. In preferred embodiments, methods and compositions for the regulation of TNF Type-1 Receptor ectodomain shedding are provided. The present invention finds use in therapeutics, diagnostics, and drug screening applications.

17 Claims, 14 Drawing Sheets

FIGURE 1

SEQUENCE LISTING

<160> NUMBER OF SEQ ID NOS: 11
<210> SEQ ID NO 1
<211> LENGTH: 4845
<212> TYPE: DNA
<213> ORGANISM: Homo sapiens

<400> SEQUENCE: 1
gcacgagagc taggccggcg gcagtggtgg tggcggcggc gcaagggtga gggcggcccc    60

-continued

```
agaaccccag gtaggtagag caagaagatg gtgtttctgc ccctcaaatg gtcccttgca      120
accatgtcat ttctactttc ctcactgttg gctctcttaa ctgtgtccac tccttcatgg      180
tgtcagagca ctgaagcatc tccaaaacgt agtgatggga caccatttcc ttggaataaa      240
atacgacttc ctgagtacgt catcccagtt cattatgatc tcttgatcca tgcaaacctt      300
accacgctga ccttctgggg aaccacgaaa gtagaaatca cagccagtca gcccaccagc      360
accatcatcc tgcatagtca ccacctgcag atatctaggg ccacccctcag gaagggagct     420 ggagagaggc tatcggaaga accccctgcag gtcctggaac accccgtca ggagcaaatt      480 gcactgctgg ctcccgagcc cctccttgtc gggctcccgt acacagttgt cattcactat      540
gctggcaatc tttcggagac tttccacgga ttttacaaaa gcacctacag aaccaaggaa      600
ggggaactga ggatactagc atcaacacaa tttgaaccca ctgcagctag aatgcctttt      660
ccctgctttg atgaacctgc cttcaaagca gtttctcaa tcaaaattag aagagagcca       720
aggcacctag ccatctccaa tatgccattg gtgaaatctg tgactgttgc tgaaggactc      780
atagaagacc attttgatgt cactgtgaag atgagcacct atctggtggc cttcatcatt     840
tcagattttg agtctgtcag caagataacc aagagtggag tcaaggtttc tgtttatgct     900
gtgccagaca agataaatca agcagattat gcactggatg ctgcggtgac tcttctagaa     960 tttatgagg attatttcag cataccgtat cccctaccca aacaagatct tgctgctatt     1020
cccgactttc agtctggtgc tatggaaaac tggggactga caacatatag agaatctgct    1080
ctgttgtttg atgcagaaaa gtcttctgca tcaagtaagc ttggcatcac aatgactgtg    1140
gcccatgaac tggctcacca gtggtttggg aacctggtca ctatggaatg gtggaatgat    1200
ctttggctaa atgaaggatt tgccaaattt atggagtttg tgtctgtcag tgtgacccat    1260
cctgaactga agttggaga ttatttcttt ggcaaatgtt ttgacgcaat ggaggtagat     1320
gctttaaatt cctcacaccc tgtgtctaca cctgtggaaa tcctgctcca gatccgggag    1380
atgtttgatg atgtttctta tgataaggga gcttgtattc tgaatatgct aagggagtat    1440
cttagtgctg acgcatttaa aagtggtatt gtacagtatc tccagaagca tagctataaa    1500
aatacaaaaa acgaggacct gtgggatagt atggcaagta tttgccctac agatggtgta    1560
aaagggatgg atggcttttg ctctagaagt caacattcat cttcatcctc acattggcat    1620
caggaagggg tggatgtgaa aaccatgatg aacacttgga cactgcagaa gggttttccc    1680
ctaataacca tcacagtgag ggggaggaat gtacacatga agcaagagca ctacatgaag    1740
ggctctgacg gcgccccgga cactgggtac ctgtggcatg ttccattgac attcatcacc    1800
agcaaatccg acatggtcca tcgattttg ctaaaaacaa aaacagatgt gctcatcctc     1860
ccagaagagg tggaatggat caaatttaat gtgggcatga atggctatta cattgtgcat    1920
tacgaggatg atggatggga ctctttgact ggccttttaa aggaacaca cacagcagtc      1980 agcagtaatg atcgggcgag tctcattaac aatgcatttc agctcgtcag cattgggaag    2040
ctgtccattg aaaaggcctt ggatttatcc ctgtacttga acatgaaac tgaaattatg     2100 cccgtgtttc aaggttgaa tgagctgatt cctatgtata agttaatgga gaaagagat     2160 atgaatgaag tggaaactca attcaaggcc ttcctcatca ggctgctaag ggacctcatt    2220
gataagcaga catggacaga cgagggctca gtctcagagc gaatgctgcg gagtcaacta    2280
ctactcctcg cctgtgtgca caactatcag ccgtgcgtac agagggcaga aggctatttc    2340
agaaagtgga aggaatccaa tggaaacttg agcctgcctg tcgacgtgac cttggcagtg    2400
tttgctgtgg gggcccagag cacagaaggc tgggattttc tttatagtaa atatcagttt    2460
```

```
tctttgtcca gtactgagaa aagccaaatt gaatttgccc tctgcagaac ccaaaataag   2520
gaaaagcttc aatggctact agatgaaagc tttaagggag ataaaataaa aactcaggag   2580
tttccacaaa ttcttacact cattggcagg aacccagtag gatacccact ggcctggcaa   2640
tttctgagga aaaactggaa caaacttgta caaaagtttg aacttggctc atcttccata   2700
gcccacatgg taatgggtac aacaaatcaa ttctccacaa gaacacggct tgaagaggta   2760
aaaggattct tcagctcttt gaaagaaaat ggttctcagc tccgttgtgt ccaacagaca   2820
attgaaacca ttgaagaaaa catcggttgg atggataaga attttgataa aatcagagtg   2880
tggctgcaaa gtgaaaagct tgaacgtatg taaaaattcc tcccttgcca ggttcctgtt   2940
atctctaatc accaacattt tgttgagtgt attttcaaac tagagatggc tgttttggct   3000
ccaactggag atacttttt  cccttcaact catttttga ctatccctgt gaaaagaata    3060
gctgttagtt tttcatgaat gggctatcgc taccatgtgt tttgttcatc acaggtgttg   3120
ccctgcaacg taaacccaag tgttgggttc cctgccacag aagaataaag taccttattc   3180
ttctcatttt atagtttatg cttaagcacc cgtgtccaaa accctgtacc ccatgtttat   3240
cattcataaa ctgtttcatc agtctcctcg aaagactctg aatagtcgac tactgaacaa   3300
tgaacacctg gatctgagac taagccggac gatgactggg ttaaagctct cccggctcac   3360
ccctccagac ccgctgccca tccctcttcc ttgctccatg cccaggggct gacttgtaaa   3420
ggccaagtca tcaagctttc ttgccctttg gatgttggtc agtggggagc cggagagctg   3480
gagctggggt cggaggaggt agtaggtgga ggtgttcttc cctgattccc ttgcgggatg   3540
cctcgggctg gcctcccctg agggttttag ctccgagagg ggaccctctt ttccacacag   3600
ccttctccac ctctggattt tggtaactgc tccctcctca tcccttcagg attagtggcc   3660
tcagtgggag tctggctttt actagtcctg gcggacttgt ggtttctaca taatgtgctc   3720
gcacttttgc aaaaaatctt cttttatag  aaccctcctc agataattct gagtgtcatc   3780
tatttccctg actggtacag tatctcttct gaaaagcag  agtgcattca agtctgtagg   3840 aaaaccctt  tcttagggag gtgatttttt ttctctctct gcttcttatt tggcctactt   3900
tacaatttct aactaactag ttattggcat ttactgacag taaattattg cagtcaccaa   3960
taaatgatag tacattgtga aacaaaatat ttgctcatat tagcaaatag gacattcttt   4020
ggctttgaag tctttctttt gtgaagactt cacacacggt tgcttcagca cacagttgct   4080
gctcaggttt tatgtataga tgataataat agaaagcaca gtttactaac atggtaaacc   4140
aacggagttc aagtcaagtc agttaatacc ctaagaatta gatttatttt cttattctga   4200
aaacttgcta cacagggact tatctaaccc atagtgtgct ctgttgctga cttgattcaa   4260
gttgcagcgt gttttgcgct gactctaagg tgcggaaatc ctcacacctg gcaaaggaga   4320
attcaaactg aacttttga  atataaggca aaaacttcaa gataagggaa tatgattgat   4380
gattggtacg aaaaatgtca aaatgtgttc ccctaataca cgacaaaata gagtgacttc   4440
tggacataaa tctgccattt attaaaccat tcactacaac aaataaatag gtataaaagt   4500
ggaattggaa ttttttatact tatttgttgt agtgaatggt ttaataaaaa tagaaatcac   4560
tggtaatttc caccccaaac taaactattt cccttctttt aaaaaaatac aaaccaaga    4620 ttttaatgta aaatattttg ctttaattgt attttatgcc ttgattaatg aaacatggaa   4680
atattgattt tcagttttgg tcacctgagg aacctatctt tgtttgcttt tggaaaagcc   4740
cattttctaa acagatacaa tattgccaca acaatgtgca gaaaccttt  tgataataaa   4800
```

-continued

```
aaattgttct tgcctctaa aaaaaaaaaa aaaaaaaaaa aaaaa                    4845
```

<210> SEQ ID NO 2
<211> LENGTH: 941
<212> TYPE: PRT
<213> ORGANISM: Homo sapiens
<400> SEQUENCE: 2

```
Met Val Phe Leu Pro Leu Lys Trp Ser Leu Ala Thr Met Ser Phe Leu
1               5                   10                  15

Leu Ser Ser Leu Leu Ala Leu Leu Thr Val Ser Thr Pro Ser Trp Cys
            20                  25                  30

Gln Ser Thr Glu Ala Ser Pro Lys Arg Ser Asp Gly Thr Pro Phe Pro
        35                  40                  45

Trp Asn Lys Ile Arg Leu Pro Glu Tyr Val Ile Pro Val His Tyr Asp
    50                  55                  60

Leu Leu Ile His Ala Asn Leu Thr Thr Leu Thr Phe Trp Gly Thr Thr
65                  70                  75                  80

Lys Val Glu Ile Thr Ala Ser Gln Pro Thr Ser Thr Ile Ile Leu His
                85                  90                  95

Ser His His Leu Gln Ile Ser Arg Ala Thr Leu Arg Lys Gly Ala Gly
            100                 105                 110

Glu Arg Leu Ser Glu Glu Pro Leu Gln Val Leu Glu His Pro Arg Gln
        115                 120                 125

Glu Gln Ile Ala Leu Leu Ala Pro Glu Pro Leu Leu Val Gly Leu Pro
    130                 135                 140

Tyr Thr Val Val Ile His Tyr Ala Gly Asn Leu Ser Glu Thr Phe His
145                 150                 155                 160

Gly Phe Tyr Lys Ser Thr Tyr Arg Thr Lys Glu Gly Glu Leu Arg Ile
                165                 170                 175

Leu Ala Ser Thr Gln Phe Glu Pro Thr Ala Ala Arg Met Ala Phe Pro
            180                 185                 190

Cys Phe Asp Glu Pro Ala Phe Lys Ala Ser Phe Ser Ile Lys Ile Arg
        195                 200                 205

Arg Glu Pro Arg His Leu Ala Ile Ser Asn Met Pro Leu Val Lys Ser
    210                 215                 220

Val Thr Val Ala Glu Gly Leu Ile Glu Asp His Phe Asp Val Thr Val
225                 230                 235                 240

Lys Met Ser Thr Tyr Leu Val Ala Phe Ile Ile Ser Asp Phe Glu Ser
                245                 250                 255

Val Ser Lys Ile Thr Lys Ser Gly Val Lys Val Ser Val Tyr Ala Val
            260                 265                 270

Pro Asp Lys Ile Asn Gln Ala Asp Tyr Ala Leu Asp Ala Ala Val Thr
        275                 280                 285

Leu Leu Glu Phe Tyr Glu Asp Tyr Phe Ser Ile Pro Tyr Pro Leu Pro
    290                 295                 300

Lys Gln Asp Leu Ala Ala Ile Pro Asp Phe Gln Ser Gly Ala Met Glu
305                 310                 315                 320

Asn Trp Gly Leu Thr Thr Tyr Arg Glu Ser Ala Leu Leu Phe Asp Ala
                325                 330                 335

Glu Lys Ser Ser Ala Ser Ser Lys Leu Gly Ile Thr Met Thr Val Ala
            340                 345                 350

His Glu Leu Ala His Gln Trp Phe Gly Asn Leu Val Thr Met Glu Trp
        355                 360                 365
```

```
Trp Asn Asp Leu Trp Leu Asn Glu Gly Phe Ala Lys Phe Met Glu Phe
    370                 375                 380

Val Ser Val Ser Val Thr His Pro Glu Leu Lys Val Gly Asp Tyr Phe
385                     390                 395                 400

Phe Gly Lys Cys Phe Asp Ala Met Glu Val Asp Ala Leu Asn Ser Ser
                405                 410                 415

His Pro Val Ser Thr Pro Val Glu Asn Pro Ala Gln Ile Arg Glu Met
            420                 425                 430

Phe Asp Asp Val Ser Tyr Asp Lys Gly Ala Cys Ile Leu Asn Met Leu
        435                 440                 445

Arg Glu Tyr Leu Ser Ala Asp Ala Phe Lys Ser Gly Ile Val Gln Tyr
    450                 455                 460

Leu Gln Lys His Ser Tyr Lys Asn Thr Lys Asn Glu Asp Leu Trp Asp
465                 470                 475                 480

Ser Met Ala Ser Ile Cys Pro Thr Asp Gly Val Lys Gly Met Asp Gly
                485                 490                 495

Phe Cys Ser Arg Ser Gln His Ser Ser Ser Ser His Trp His Gln
                500                 505                 510

Glu Gly Val Asp Val Lys Thr Met Met Asn Thr Trp Thr Leu Gln Lys
            515                 520                 525

Gly Phe Pro Leu Ile Thr Ile Thr Val Arg Gly Arg Asn Val His Met
    530                 535                 540

Lys Gln Glu His Tyr Met Lys Gly Ser Asp Gly Ala Pro Asp Thr Gly
545                 550                 555                 560

Tyr Leu Trp His Val Pro Leu Thr Phe Ile Thr Ser Lys Ser Asp Met
                565                 570                 575

Val His Arg Phe Leu Leu Lys Thr Lys Thr Asp Val Leu Ile Leu Pro
        580                 585                 590

Glu Glu Val Glu Trp Ile Lys Phe Asn Val Gly Met Asn Gly Tyr Tyr
    595                 600                 605

Ile Val His Tyr Glu Asp Asp Gly Trp Asp Ser Leu Thr Gly Leu Leu
    610                 615                 620

Lys Gly Thr His Thr Ala Val Ser Ser Asn Asp Arg Ala Ser Leu Ile
625                 630                 635                 640

Asn Asn Ala Phe Gln Leu Val Ser Ile Gly Lys Leu Ser Ile Glu Lys
                645                 650                 655

Ala Leu Asp Leu Ser Leu Tyr Leu Lys His Glu Thr Glu Ile Met Pro
            660                 665                 670

Val Phe Gln Gly Leu Asn Glu Leu Ile Pro Met Tyr Lys Leu Met Glu
        675                 680                 685

Lys Arg Asp Met Asn Glu Val Glu Thr Gln Phe Lys Ala Phe Leu Ile
    690                 695                 700

Arg Leu Leu Arg Asp Leu Ile Asp Lys Gln Thr Trp Thr Asp Glu Gly
705                 710                 715                 720

Ser Val Ser Glu Arg Met Leu Arg Ser Gln Leu Leu Leu Ala Cys
                725                 730                 735

Val His Asn Tyr Gln Pro Cys Val Gln Arg Ala Glu Gly Tyr Phe Arg
        740                 745                 750

Lys Trp Lys Glu Ser Asn Gly Asn Leu Ser Leu Pro Val Asp Val Thr
    755                 760                 765

Leu Ala Val Phe Ala Val Gly Ala Gln Ser Thr Glu Gly Trp Asp Phe
770                 775                 780

Leu Tyr Ser Lys Tyr Gln Phe Ser Leu Ser Ser Thr Glu Lys Ser Gln
```

```
                785                 790                 795                 800
    Ile Glu Phe Ala Leu Cys Arg Thr Gln Asn Lys Glu Lys Leu Gln Trp
                    805                 810                 815
    Leu Leu Asp Glu Ser Phe Lys Gly Asp Lys Ile Lys Thr Gln Glu Phe
                820                 825                 830
    Pro Gln Ile Leu Thr Leu Ile Gly Arg Asn Pro Val Gly Tyr Pro Leu
                835                 840                 845
    Ala Trp Gln Phe Leu Arg Lys Asn Trp Asn Lys Leu Val Gln Lys Phe
            850                 855                 860
    Glu Leu Gly Ser Ser Ile Ala His Met Val Met Gly Thr Thr Asn
    865                 870                 875                 880
    Gln Phe Ser Thr Arg Thr Arg Leu Glu Glu Val Lys Gly Phe Phe Ser
                    885                 890                 895
    Ser Leu Lys Glu Asn Gly Ser Gln Leu Arg Cys Val Gln Gln Thr Ile
                900                 905                 910
    Glu Thr Ile Glu Glu Asn Ile Gly Trp Met Asp Lys Asn Phe Asp Lys
                915                 920                 925
    Ile Arg Val Trp Leu Gln Ser Glu Lys Leu Glu Arg Met
                930                 935                 940

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ataaccatca cagtgagggg gagg                                                24

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
tagttgactc cgcagcattc gctc                                                24

<210> SEQ ID NO 5
<211> LENGTH: 26
<212> TYPE: DNA
<213> ORGANISM: Artificial Sequence
<220> FEATURE:
<223> OTHER INFORMATION: Synthetic

<400> SEQUENCE: 5
gcaagaagat ggtgtttctg cccctc                                              26

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
ttacatacgt tcaagctttt cact                                                24

<210> SEQ ID NO 7
```

```
<211> LENGTH: 17
<212> TYPE: PRT
<213> ORGANISM: Artificial Sequence
<220> FEATURE:
<223> OTHER INFORMATION: Synthetic

<400> SEQUENCE: 7

Arg Gly Arg Asn Val His Met Lys Gln Glu His Tyr Met Lys Gly Ser
1               5                   10                  15

Asp

<210> SEQ ID NO 8
<211> LENGTH: 12
<212> TYPE: PRT
<213> ORGANISM: Artificial Sequence
<220> FEATURE:
<223> OTHER INFORMATION: Synthetic

<400> SEQUENCE: 8

Thr Val Ala His Glu Leu Ala His Gln Trp Phe Gly
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Leu Trp Leu Asn Glu Gly Phe Ala
1               5

<210> SEQ ID NO 10
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(4)
<223> OTHER INFORMATION: XAA at these positions can be any amino acid.

<400> SEQUENCE: 10

His Glu Xaa Xaa His Tyr Tyr Tyr Tyr Tyr Tyr Tyr Tyr Tyr Tyr Tyr
1               5                   10                  15

Tyr Tyr Tyr Tyr Tyr Tyr Tyr Glu
            20

<210> SEQ ID NO 11
<211> LENGTH: 24
<212> TYPE: PRT
<213> ORGANISM: Artificial Sequence
<220> FEATURE:
<223> OTHER INFORMATION: Artificial/Unknown

<400> SEQUENCE: 11

His Glu Leu Ala His Tyr Tyr Tyr Tyr Tyr Tyr Tyr Tyr Tyr Tyr Tyr
1               5                   10                  15

Tyr Tyr Tyr Tyr Tyr Tyr Tyr Glu
            20
```

REGULATORS OF TYPE-1 TUMOR NECROSIS FACTOR RECEPTOR AND OTHER CYTOKINE RECEPTOR SHEDDING

This application is the national stage entry of PCT/US01/06464, filed Feb. 28, 2001, which claims priority benefit to U.S. Provisional Patent Application No. 60/185,586, filed Feb. 28, 2000.

This invention was made during the course of work supported by the United States Government under the National Institutes of Health. As such, the United States Government may have certain rights to this invention.

FIELD OF THE INVENTION

The present invention provides compositions and methods related to regulation of cytokine signaling through the Tumor Necrosis Factor (TNF) pathway. Specifically, the invention provides novel genes, polypeptides and related compositions and methods for the regulation of TNF Type-1 Receptor ectodomain shedding. It is contemplated that the compositions and methods of the present invention will also find use in the regulation of ectodomain shedding of other cytokine receptors. It is further contemplated that these compositions and methods will find use in therapeutics for the treatment of diseases and disorders of the immune system.

BACKGROUND OF THE INVENTION

Aberrant regulation of cytokine signaling results in a wide variety of hyper-inflammatory, autoimmune and immune-deficiency pathological conditions. Cytokines are a large and diverse group of molecules which mediate interactions between cells, ultimately regulating the wide variety of cells of the immune repertoire. Cytokine signaling mediates numerous facets of normal immune system physiology, including development, response, activation, maintenance, memory and apoptosis (Roitt et al. (Eds.), *Immunology*, Fifth Edition, Mosby International Publishers [1998]).

Tumor Necrosis Factor

Tumor necrosis factor-α (commonly written as TNF, but also written as tumor necrosis factor or TNFα) is a multi-functional cytokine mediating pleiotropic biological functions in both health and disease states. TNF is secreted primarily by monocytes and macrophages, but can also be secreted by other cell types. The list of processes regulated by TNF is extensive, and includes inflammation, immunoregulation, cyytotoxicity and antiviral effects (See e.g., Vilcek et al, *J. Biol. Chem.*, 266:7313–7316 [1991]). TNF plays an integral role in destroying tumors, mediating responses to tissue injury, and protecting hosts from infections by various microorganisms (Vassali, *Ann. Rev. Immunol.*, 10:411–452 [1992]). TNF also induces the transcriptional activation of numerous genes, including NF-κB and AP-1, with the consequent expression of pro-inflammatory and immunoregulatory genes (Rothe et al., *Cell* 83:1243–124 [1995]; Varfolomeev et al., *J. Exp. Med.*, 183:1271–1275 [1996]; Chinnaiyan et al., *J. Biol. Chem.*, 271:4961–4965 [1996]; Hsu et al., *Immunity* 4:387–396 [1996]; and Hsu et al., *Cell* 84:299–308 [1996]). TNF-mediated NF-κB activation is also an important negative feedback mechanism regulating apoptosis (Beg and Baltimore, *Science* 274:782–784 [1996]; Van Antwerp et al., *Science* 274:787–789 [1996]; and Wang et al., *Science* 274:784–787 [1996]).

TNF in Disease

TNF has also been implicated in the pathogenesis of a variety of diseases and disorders. It is theorized that these pathologies result from the aberrant regulation of TNF activity, in which the pathologies manifest as a result of excessive or insufficient TNF activity. Among the activities for which TNF is most noted are its pro-inflammatory actions, sometimes termed the "acute phase immune response." Unfortunately, if not properly regulated, these proinflammatory responses can result in tissue injury and chronic inflammatory diseases, such as rheumatoid arthritis, inflammatory bowel disease, septic shock, cachexia, autoimmune disorders, graft-versus-host disease and insulin resistance (Piguet et al., *J. Exp. Med.*, 166:1280 [1987]; Pujol-Borrell et al., *Nature* 326:304–306 [1987]; Tracey et al., *Nature* 330:662–664 [1987]; Oliff, *Cell* 54:141–142 [1988]; Vilcek et al., *J. Biol. Chem.*, 266:7313–7316 [1991]; and Eigler et al., *Immunol. Today* 18:487–92 [1997]). Excessive TNF activity results in the detrimental effects of an exaggerated immune response demonstrated in some of these diseases, exemplified by overstimulation of interleukin-6 and granulocyte/macrophage-colony stimulating factor (GM-CSF) secretion, enhanced cytotoxicity of polymorphonuclear neutrophils, prolonged expression of cellular adhesion molecules, induction of procoagulant activity on vascular endothelial cells, increased adherence of neutrophils and lymphocytes, and stimulation of the release of platelet activating factor from macrophages, neutrophils and vascular endothelial cells (Vassali, *Ann. Rev. Immunol.*, 10:411–452 [1992]; Vilcek et al., *J. Biol. Chem.*, 266:7313–7316 [1992]; and Barbara et al., *Immunol. and Cell Biol.*, 74:434–443 [1996]).

Recent evidence also implicates TNF activity in the pathogenesis of many infections. TNF is thought to play a central role in the pathophysiological consequences of Gram-negative sepsis and endotoxic shock, including fever, malaise, anorexia, and cachexia (Beutler et al., *Nature* 316:552–554 [1985]; Bauss et al, *Infect. Immun.*, 55:1622–1625 [1987]; Tracey et al., *Nature* 330:662–664 [1987]; and Vassali, *Ann. Rev. Immunol.*, 10:411–452 [1992]). Because TNF can mimic many of the biological effects of endotoxin, it is theorized that TNF is a central mediator responsible for the clinical manifestations of endotoxin-related and other critical illnesses (Waage et al., *Lancet* 1:355–357 [1987]; Cerami et al., *Immunol. Today* 9:28 [1988]; Mitchie et al., *N. Eng. J. Med.*, 318:1481–1486 [1988]; Revhaug et al., *Arch. Surg.*, 123:162–170 [1988]; and Michie et al., *Ann. Surg.*, 209:19–24 [1989]).

Tumor Necrosis Factor Receptor

The numerous biological effects of TNF are now known to be mediated by two transmembrane receptors, the 55 kilodalton Type I receptor (also written as "CD120a," and referred to herein as "TNFR1") and the 75 kilodalton Type II receptor (also written as "CD120b," and referred to herein as TNFR2). Although both TNFR1 and TNFR2 demonstrate strong affinity for TNFα, these two receptors demonstrate no apparent homology in their cytoplasmic (i.e., intracellular) domains. This fact is consistent with the observation that these two receptors transduce different signals to the nucleus via distinct signaling intermediates (Lewis et al., *Proc. Natl. Acad. Sci. USA* 88:2830–2834 [1991]; Tartaglia and Goeddel, *Immunol. Today* 13:151–153 [1992]; and Barbara et al., *Imunol. Cell Biol.*, 74:434–443 [1996]).

Soluble TNF inhibitors have been identified in normal human urine, as well as in sera and other body fluids of patients with infectious, neoplastic and immunologic disorders. This observation ultimately led to the revelation that these soluble TNF inhibitors were actually the extracellular domains of TNF receptors derived by proteolytic cleavage of the transmembrane forms (Engelmann et al., *J. Biol. Chem.*, 264:11974–11980 [1989]; Olsson et al., *Eur. J. Haematol.*, 42:270–275 [1989]; Seckinger et al., *J Biol. Chem.*, 264:11966–11973 [1989]; Engelmann et al., *J. Biol. Chem.*, 265:1531–1536 [1990]; and Aderka et al., *J. Exp. Med.*, 175:323–329 [1992]). In the case of the TNFR1, this proteolytic activity results in the cleavage and shedding of the extracellular N-terminal domain (also called the ectodomain). These free, soluble TNFR1 ectodomains ("sTNFR1s") have an affinity for TNF that is similar to that of intact membrane receptors. Due to this affinity, the free receptors are able to bind and sequester TNF, thereby inhibiting the biological action of TNF. Furthermore, the generation of sTNFR1 is also likely to suppress TNF signaling by reducing the number of functional TNF receptors acting at the cell membrane. The sTNFR1 ectodomains are also theorized to serve a more complex buffering function in the regulation of TNF activity (Aderka et al., *J. Exp. Med.*, 175:323–329 [1992]; and Werb and Yan, *Science* 282: 1279–1280 [1998]). The complexity of TNF signaling is fuirther illustrated by the observation that many of the stimuli that result in TNF release also result in the release of the soluble TNF receptor, suggesting that these soluble TNF inhibitors may serve as part of a regulated feedback mechanism to control TNF activity (Adreke et al., *J. Exp. Med.*, 175:323–329 [1992]; and Porteu and Nathan, *J. Exp. Med.*, 172:599–607 [1990]).

The importance of TNFR1 in the regulation of TNF activity in host defense, immunoregulation and development has been fuirther demonstrated in studies utilizing TNFR1 knockout mice. Mice deficient in TNFR1 show a variety of phenotypes, including phenotypes which mimic human immune disorders (Pfeffer et al., *Cell* 73:457–467 [1993]; Rothe, *Nature* 364:798–802 [1993]; Le Hir et al., *J. Exp. Med.*, 183:2367–2372 [1996]; Matsumoto et al., *Science* 271:1289–1291[1996]; Mori et al. *J. Immunol.* 157:3178–3182 [1996]; Speiser et al., *J. Immunol.*, 158: 5185–5190 [1997]; Tkachuk et al., *J. Exp. Med.*, 187: 469–477 [1998]; and Kagi et al., *J. Immunol.*, 162:4598–4605 [1999]).

The key role of TNFR1 shedding in the regulation of TNF bioactivity is highlighted by the association of germline mutations in TNFR1 extracellular domains with impaired TNFR1 shedding and autoinflammatory disease characterized by autosomal dominant periodic fever syndromes (McDermott et al., *Cell* 97:133–144 [1999]).

Other Mediators of Acute Phase Response

In addition to TNF, other cytokines have been implicated in the induction of the pro-inflammatory response (i.e., the acute phase immune response). These cytokines which demonstrate overlapping activities with TNF include the interleukins (e.g., IL-1 and IL-6) (Suffredini et al., *J. Clin. Immunol.*, 19:203–214 [1999]).

IL-1 (consisting of both α and β forms) is an important proinflammatory cytokine which regulates the expression of a wide variety of target genes and proteins in nearly every cell type (Dinarello, *Blood* 77:1627–1652 [1991]; and Dinarello, *The Cytokine Handbook* (ed. Angus W. Thomson), $3^{rd}$ edition, Academic Press, San Diego, p. 35–72 [1998]). The spectrum of IL-1-mediated biologic effects includes inflammatory, metabolic, physiologic, hematopoietic, and immunologic functions. IL-1 is thought to play a role in the pathogenesis of several disease states, including septic shock, rheumatoid arthritis, inflammatory bowel disease, myelogenous leukemia, diabetes mellitus, and atherosclerosis (Dinarello et al., *N. Engl. J. Med.*, 328:106–113 [1993]).

IL-6 is also a multifunctional cytokine with pleiotropic pro-inflammatory effects (DiCosmo, et al., *J. Clin. Invest.*, 94:2028–2035 [1994]; and Kishimoto et al., *Blood* 86:1243–1254 [1995]). For example, IL-6 plays an important role in regulating B cell immunoglobulin production, T-cell activation, growth and differentiation, hematopoiesis, hepatic acute phase reactions and osteoclast development (Hirano, *The Cytokine Handbook* (ed. Angus W. Thomson), $3^{rd}$ edition, Academic Press, San Diego, p. 197–228 [1998]). Dysregulated production of IL-6 may contribute to the pathogenesis of a variety of inflammatory, neoplastic and autoimmune disorders, such as plasma cell neoplasia and Castleman's disease (Yoshizaki, et al., *Blood* 74:1360–1367 [1989]; and Hirano, *Int. J. Cell Cloning* 9:166–184 [1991]).

The signal transduction pathways utilized by TNF, IL-1 and IL-6 also show shared signaling intermediates. For example, both TNF and IL-1 can activate both NF-κB and AP-1, which are important pro-inflammatory transcription factors (Ashkenazi et al., *Science* 281:1305–1308 [1998]; and Dinarello, *The Cytokine Handbook* (ed. Angus W. Thomson), $3^{rd}$ edition, Academic Press, San Diego, p. 35–72 [1998]). Similarly, IL-6 signaling uses components of the JAK-STAT pathway, which has also been reported to be induced by TNF (Guo et al., *J. Immunol.*, 160:2742–2750 [1998]; and Hirano, *The Cytokine Handbook* (ed. Angus W. Thomson), $3^{rd}$ edition, Academic Press, San Diego, p. 197–228 [1998]).

The cognate receptors for the IL-1 and IL-6 cytokines are known. There are two IL-1 receptor forms, type I and type II. There is a single IL-6 receptor, consisting of gp80 alpha chain and gp130 beta chain subunits, where ligand binding is mediated by the alpha subunit. The IL-1 and IL-6 receptors are also present as soluble forms analogous to the soluble form of TNFR1. Furthermore, it has been suggested that these receptors play a role in the regulation of IL-1 and IL-6 activity and pro-inflammatory response (Dower et al., *J. Immunol.*, 142:4314 [1989]; Novick et al., *J. Exp. Med.*, 170:1409 [1989]; Eastgate et al., *FEBS Lett.*, 260:213 [1990]; Giri et al., *J. Biol. Chem.*, 265:17416 [1990]; Symons et al., *Cytokine* 2:190 [1990]; Symons et al., *FEBS Lett.*, 272:133 [1990]; Symons et al., *J. Exp. Med.*, 174: 1251–1254 [1991]; Mullberg et al., *Biochem. Biophys. Res. Commun.*, 189:794 [1992]; Mullberg et al., *Eur. J. Immunol.*, 23:473 [1993]; Svenson et al., *Cytokine* 5:427 [1993]; and Arend et al., *J. Immunol.*, 153:4766–4774 [1994]).

Analogy between regulation of TNF and other cytokines is further illustrated by studies utilizing peptide-hydroxamate metalloprotease inhibitors. Specifically, the protease inhibitors TAPI (TNF-α protease inhibitor) and RU36156 have been reported to inhibit the proteolytic cleavage and shedding of both TNFR1 and IL-6R (Mullberg et al., *J. Immunol.*, 155:5198–5205 [1995]; and Gallea-Robache et al., *Cytokine* 9:340–346 [1997]).

As discussed above, in view of the importance of TNF, IL-1 and IL-6 in both health and disease states, there exists a need for methods and compositions for the regulation of TNF, IL-1 and IL-6 cytokine activity. These methods and compositions will find use as therapeutic agents for the treatment of disease states.

SUMMARY OF THE INVENTION

The present invention provides compositions and methods related to regulation of cytokine signaling through the Tumor Necrosis Factor (TNF) pathway, as well as other signaling pathways controlled by other cytokines, including IL-1 and IL-6. It is contemplated that these compositions and methods will find use in therapeutics for the treatment of diseases and disorders of the immune system.

The present invention also provides novel polypeptides and a nucleic acid sequences. In particular, the present invention provides isolated nucleic acids comprising the nucleotide sequence set forth in SEQ ID NO:1, which encodes a polypeptide referred to as "ARTS-"1 (i.e., aminopeptidase regulator of type I, 55 kDa tumor necrosis factor receptor ectodomain shedding) which has the ability to promote the shedding of the extracellular domain of Type I Tumor Necrosis Factor Receptor (TNFR1). Thus, the present invention also provides the isolated polypeptides comprising the amino acid sequence set forth in SEQ ID NO:2, as well as isolated nucleic acids encoding the polypeptide set forth in SEQ ID NO:2.

The present invention further provides recombinant vectors comprising the ARTS-1 gene and host cells comprising these vectors. In one embodiment, the host cell is eukaryotic, while in an alternative embodiment, the host cell is prokaryotic. The present invention also provides antibodies raised against at least a portion of the ARTS-1 polypeptide of SEQ ID NO:2. In some embodiments, the antibodies are monoclonal, while in alternative embodiments, the antibodies are polyclonal.

In other embodiments, the present invention provides isolated nucleic acids that are substantially homologous to the nucleic acid of SEQ ID NO:1, wherein the nucleic acid is capable of hybridizing under high stringency conditions to the nucleic acid of SEQ ID NO:1. In a preferred embodiment, the nucleic acid substantially homologous to the ARTS-1 gene encodes a polypeptide having the ability to regulate the shedding of the extracellular domain of at least one cytokine receptor. In particularly preferred embodiments, the cytokine receptor is selected from the group consisting of type-1 tumor necrosis factor receptor, type I interleukin-1 cytokine receptor, type II interleukin-1 cytokine receptor, and interleukin-6 cytokine receptor alpha-chain gp80. In some embodiments, the nucleic acid substantially homologous to the nucleic acid of the ARTS-1 gene is identified using PCR methods. In alternative embodiments, the nucleic acid substantially homologous to the ARTS-1 gene is identified using hybridization screening methods.

The present invention further provides methods for the isolation of amplifiable nucleic acid substantially homologous to the nucleic acid of SEQ ID NO:1 comprising: providing a sample comprising template nucleic acid suspected of encoding a gene substantially homologous to the nucleic acid of SEQ ID NO:1; and at least two primers; annealing the primers to the template nucleic acid; extending the primers (e.g., with reiterated DNA synthesis) under conditions such that the template nucleic acid is amplified, to produce an amplified product; and visualizing the amplified product. In some preferred embodiments, the amplified product is isolated. The present invention further provides the product of these amplification methods. In preferred embodiments, the amplified product encodes a polypeptide having the ability to regulate the shedding of the extracellular domain of at least one cytokine receptor. In particularly preferred embodiments, the cytokine receptor is selected from the group consisting of type-1 tumor necrosis factor receptor, type I interleukin-1 cytokine receptor, type II interleukin-1 cytokine receptor, and interleukin-6 cytokine receptor alpha-chain gp80.

The present invention also provides methods for the use of these compositions to regulate the shedding of sTNFR1. It is contemplated that methods which regulate the shedding of the sTNFR1 also regulate the activity of TNF. In a most preferred embodiment, the invention provides methods for use of these compositions in therapeutic applications in the treatment of immune system diseases and disorders resulting from aberrant cytokine activity.

The present invention provides methods for regulating the shedding of the extracellular domain of at least one cytokine receptor, comprising the steps of: providing a recombinant vector comprising SEQ ID NO:1 in the sense orientation, a first tissue containing one or more cells expressing at least one cytokine receptor, and a second tissue comprising one or more cells capable of expressing the polypeptide encoded by the recombinant vector; delivering the vector to the cells of the second tissue in the presence of the first tissue, under conditions which result in regulation of shedding of the cytokine receptor(s) from cells of the first tissue. In some preferred embodiments, the cytokine receptor is selected from the group consisting of type-1 tumor necrosis factor receptor, type I interleukin-1 cytokine receptor, type II interleukin-1 cytokine receptor, and interleukin-6 cytokine receptor alpha-chain gp80. In alternative preferred embodiments, the delivery of the vector to the second tissue comprises a means of intracellular delivery selected from the group consisting of direct nucleic acid administration, liposome administration, viral vector delivery, and ex vivo gene delivery followed by transplantation.

In other embodiments, the present invention provides compositions and methods suitable for regulating TNFR1 ectodomain shedding by overexpressing or suppressing the activity of the ARTS-1 polypeptide. In some of these embodiments, TNFR1 ectodomain shedding is regulated by the intracellular delivery of a vector which results in overexpression of the ARTS-1 polypeptide (e.g., SEQ ID NO:2). In another embodiment, TNFR1 ectodomain shedding is regulated by delivering purified ARTS-1 polypeptide (e.g., SEQ ID NO:2) to tissues.

The present invention also provides methods for regulating the shedding of the extracellular domain of at least one cytokine receptor, comprising the steps of: providing a recombinant vector comprising at least a transcribeable portion of the nucleic acid of SEQ ID NO:1 in an antisense orientation, a first tissue comprising one or more cells expressing at least one cytokine receptor, and a second tissue comprising one or more cells expressing the endogenous polypeptide of SEQ ID NO:2, and one or more cells capable of transcribing the antisense nucleic acid; and delivering the vector to the second tissue in the presence of the first tissue, under conditions that result in regulation of shedding of the cytokine receptor(s) from the cells of the first tissue. In preferred embodiments, the cytokine receptor is selected from the group consisting of type-1 tumor necrosis factor receptor, type I interleukin-1 cytokine receptor, type II interleukin-1 cytokine receptor, and interleukin-6 cytokine receptor alpha-chain gp80. In alternative preferred embodiments, the delivery of the vector to the second tissue comprises a means of intracellular delivery selected from the group consisting of direct nucleic acid administration, liposome administration, viral vector delivery, and ex vivo gene delivery followed by transplantation.

The present invention further provides methods for regulating the shedding of the extracellular domain of at least one cytokine receptor, comprising the steps of: providing a polypeptide having the amino acid sequence set forth in SEQ ID NO:2, and a tissue comprising one or more cells expressing at least one cytokine receptor on their plasma membrane extracellular surface; and delivering the polypeptide to the tissue under conditions such that the polypeptide regulates the shedding of the cytokine receptor(s) from the surface of the cells of the tissue. In some preferred embodiments, the cytokine receptor is selected from the group consisting of type-1 tumor necrosis factor receptor, type I interleukin-1 cytokine receptor, type II interleukin-1 cytokine receptor, and interleukin-6 cytokine receptor alpha-chain gp80. In alternative preferred embodiments, the delivery of the polypeptide to the tissue comprises a means of delivery selected from the group consisting of oral administration, intra-arterial injection, intravenous injection, intramuscular injection, intraperitoneal injection, subcutaneous injection, suppository, local surgical administration, systemic surgical administration, catheter, and any combination of these means of delivery.

The present invention further provides methods for regulating the shedding of the extracellular domain of at least one cytokine receptor, providing an antibody raised against the ARTS-1 polypeptide, and a tissue comprising one or more cells expressing at least one cytokine receptor and the endogenous polypeptide of SEQ ID NO:2; and delivering the antibody to the tissue under conditions such that the antibody regulates the shedding of the cytokine receptor(s) from the surface of the cells of the tissue. In some preferred embodiments, the cytokine receptor is selected from the group consisting of type-1 tumor necrosis factor receptor, type I interleukin-1 cytokine receptor, type II interleukin-1 cytokine receptor, and interleukin-6 cytokine receptor alpha-chain gp80. In alternative preferred embodiments, the means of delivery is selected from the group consisting of oral administration, intra-arterial injection, intravenous injection, intramuscular injection, intraperitoneal injection, subcutaneous injection, suppository, local surgical administration, systemic surgical administration, catheter, and any combination of these means of delivery.

In view of the overlapping activities between TNF and other proinflammatory cytokines, the present invention also provides compositions and methods suitable for regulating the shedding of other cytokine receptors in addition to TNFR1, including, but not limited to IL-1 and IL-6 cytokine receptors.

In some particularly preferred embodiments, the present invention provides compositions and methods to treat subjects displaying pathology, as well as subjects suspected of displaying or at risk of displaying pathology resulting from abnormal cytokine activity. The compositions provided for use in the most preferred embodiment include vectors capable of expressing the ARTS-1 polypeptide, vectors capable of transcribing at least a portion of the ARTS-1 gene in an antisense orientation, the ARTS-1 polypeptide set forth in SEQ ID NO:2, and antibodies raised against at least a portion of the ARTS-1 polypeptide.

The present invention also provides methods for treating a subject, comprising the steps of: providing a composition selected from the group consisting of a recombinant vector comprising at least a portion of SEQ ID NO:1 in the sense orientation, a recombinant vector comprising at least a portion of SEQ ID NO:1 in the antisense orientation, at least a portion of the ARTS-1 polypeptide, at least a portion of SEQ ID NO:2, and antibody directed against at least a portion of the ARTS-1 polypeptide, as well as a subject, and a means of delivery of the composition to at least one tissue of the subject; and delivering the composition to the subject using the means of delivery. In preferred embodiments, the subject is selected from the group consisting of a subject displaying pathology resulting from abnormal cytokine activity, a subject suspected of displaying pathology resulting from abnormal cytokine activity, and a subject at risk of displaying pathology resulting from abnormal cytokine activity. In some preferred embodiments, the cytokine activity is mediated by a cytokine selected from the group consisting of tumor necrosis factor α, interleukin-1 alpha, interleukin-1 beta, and interleukin-6. In some particularly preferred embodiments, the subject is a human. In alternative preferred embodiments, the means of delivery is selected from the group consisting of oral administration, intra-arterial injection, intravenous injection, intramuscular injection, intraperitoneal injection, subcutaneous injection, suppository, local surgical administration, systemic surgical administration, catheter, and any combination of these means of delivery. In further preferred embodiments, the means of delivery is further selected from the group consisting of direct nucleic acid administration, liposome administration, viral vector delivery, and ex vivo gene delivery followed by transplantation.

In other embodiments, the present invention provides ARTS-1 markers, including those selected from the group consisting of the ARTS-1 mRNA transcript and the ARTS-1 polypeptide. Furthermore, the invention also provides compositions and means for detecting the ARTS-1 mRNA and polypeptide markers. In preferred embodiments, these compositions are selected from the group consisting of nucleic acid complementary to the ARTS-1 mRNA, and antibodies specific for at least a portion of the ARTS-1 polypeptide.

The present invention also provides means for detecting an ARTS-1 mRNA in a sample, wherein the means comprises at least a portion of the nucleic acid of SEQ ID NO:1 complementary to at least a portion of ARTS-1 mRNA, and further wherein the nucleic acid is a probe. In alternative embodiments, the means comprises Northern blotting. In preferred embodiments, the sample is a tissue sample from a subject. In additional preferred embodiments, the methods provide means for detecting an ARTS-1 polypeptide in a sample, wherein the means comprises an antibody directed against at least a portion of the ARTS-1 polypeptide. In some preferred embodiments, the means comprises Western immunoblotting, while in alternative preferred embodiments, the means comprises an enzyme-linked immunosorbent assay. In alternative preferred embodiments, the sample is a tissue sample from a subject.

The present invention also provides diagnostic kits comprising a means to measure ARTS-1 expression, wherein the means comprises at least a portion of SEQ ID NO:1 that is complementary to at least a portion of ARTS-1 mRNA, and further wherein the nucleic acid is a probe. In alternative embodiments, the diagnostic kits of the present invention provides means for detecting an ARTS-1 polypeptide in a sample, wherein the means comprises antibody directed against at least a portion of the ARTS-1 polypeptide. In some preferred embodiments, the means comprises Western immunoblotting, while in alternative preferred embodiments, the means comprises an enzyme-linked immunosorbent assay.

The present invention further provides compositions and methods for the screening for drugs with the ability to regulate ARTS-1 peptidase activity and cytokine receptor shedding regulatory activity. In some embodiments, the present invention provides methods for drug screening to identify drugs having the ability to regulate ARTS-1 expression comprising the steps of: providing a drug, cultured cells, and a means to measure ARTS-1 expression, wherein the means comprises at least a portion of SEQ ID NO:1 that is complementary to at least a portion of ARTS-1 mRNA, and further wherein the nucleic acid is a probe; exposing the cells to the drug; and using the means to measure ARTS-1 expression. In alternative embodiments, the diagnostic kits of the present invention provide means for detecting an ARTS-1 polypeptide in a sample, wherein the means comprises an antibody directed against at least a portion of the ARTS-1 polypeptide. In some preferred embodiments, the cultured cells are human NCI-H292 pulmonary mucoepidermoid carcinoma cells.

The present invention further provides methods for drug screening to identify drugs capable of regulating the peptidase activity of ARTS-1, comprising the steps of: providing purified ARTS-1 polypeptide, an amino acid p-nitroaniline, a means to measure amino acid p-nitroaniline cleavage, and a drug; exposing the purified ARTS-1 polypeptide to the amino acid p-nitroaniline in the absence and presence of the drug; and measuring amino acid p-nitroaniline cleavage in the absence and presence of the drug. In some preferred embodiments, the purified ARTS-1 polypeptide comprises glutathione-S-transferase. In alternative preferred embodiments, the amino acid p-nitroaniline is selected from the group consisting of isoleucine p-nitroanilide, phenylalanine p-nitroanilide and glycine p-nitroanilide. In still further preferred embodiments, the means to measure amino acid p-nitroaniline cleavage comprises measuring absorbance at 380 nm.

The present invention also provides methods for drug screening to identify drugs capable of regulating the shedding of a cytokine receptor, comprising the steps of: providing cultured cells expressing at least one cytokine receptor, a means to quantitate the concentration of the soluble form of the cytokine receptor(s) in the supernatants of the cultured cells, and a drug; culturing the cells in the absence and presence of the drug; quantitating the concentration of the soluble form of the cytokine receptor(s) in the supernatants of the cultured cells; and comparing the concentrations of the soluble cytokine receptor(s) in the supernatants of the cell cultures in the absence and presence of drug. In some preferred embodiments, the cytokine receptor is selected from the group consisting of type-1 tumor necrosis factor receptor, type II interleukin-1 cytokine receptor, and interleukin-6 cytokine receptor alpha-chain gp80. In alternative preferred embodiments, the means to quantitate the concentration of the soluble form of a cytokine receptor comprises an enzyme-linked immunosorbent assay. In further embodiments, the cultured cells are cultured human NCI-H292 pulmonary mucoepidermoid carcinoma cells.

DESCRIPTION OF THE FIGURES

FIG. 1 presents the ARTS-1 transcription unit and open reading frame translation.

DEFINITIONS

Figure 2:
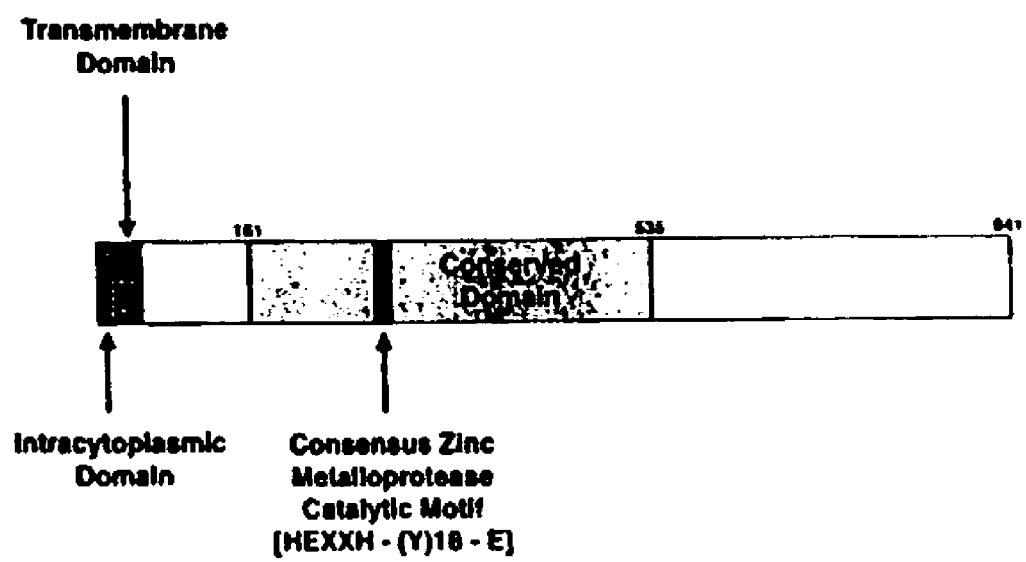
FIG. 2 provides a schematic representation of the ARTS-1 protein, indicating domains of homology with the aminopeptidase family of gluzincin zinc metalloproteases.

To facilitate an understanding of the present invention, a number of terms and phrases are defined or clarified below:

The terms "peptide," "polypeptide" and "protein" all refer to a primary sequence of amino acids that are joined by covalent "peptide linkages." In general, a peptide consists of a few amino acids, typically from 2–25 amino acids, and is shorter than a protein. Polypeptides may encompass either peptides or proteins. Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the term "nucleic acid" refers to any sequence of the bases adenine, thymine, cytosine and guanine, and various analogs of these bases. A nucleic acid is characterized by a specific nucleotide sequence (i.e., the sequence of the bases and base analogs in the molecule). A "nucleic acid" is not limited to DNA or RNA, and is not limited in any way by the size of the molecule. A nucleic acid may be double stranded or single stranded. The term "nucleic acid" encompasses sequences that include any of the bases adenine, thymine, guanine and cytosine, as well as known analogs of these bases, including but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 24 residue oligonucleotide is referred to as a "24-mer." Oligonucleotides can form secondary and tertiary structures by self-hybridizing or by hybridizing to other polynucleotides. Such structures can include, but are not limited to, duplexes, hairpins, cruciforms, bends, and triplexes.

As used herein, "recombinant nucleic acid," "recombinant gene" or "recombinant DNA molecule" indicate that the nucleotide sequence or arrangement of its parts is not a native configuration, and has been manipulated by molecular biological techniques. The term implies that the DNA molecule is comprised of segments of DNA that have been artificially joined together. Protocols and reagents to manipulate nucleic acids are common and routine in the art (See e.g., Maniatis et al.(eds.), *Molecular Cloning: A Laboratory Manual*, Cold Spring Harbor Laboratory Press, NY, [1982]; Sambrook et al. (eds.), *Molecular Cloning: A Laboratory Manual*, Second Edition, Volumes 1–3, Cold Spring Harbor Laboratory Press, NY, [1989]; and Ausubel et al. (eds.), *Current Protocols in Molecular Biology*, Vol. 1–4, John Wiley & Sons, Inc., New York [1994]).

Similarly, a "recombinant protein" or "recombinant polypeptide" refers to a protein molecule that is expressed from a recombinant DNA molecule. Use of these terms indicates that the primary amino acid sequence, arrangement of its domains or nucleic acid elements which control its expression are not native, and have been manipulated by molecular biology techniques. As indicated above, techniques to manipulate recombinant proteins are also common and routine in the art.

The terms "exogenous" and "heterologous" are sometimes used interchangeably with "recombinant." An "exogenous nucleic acid," "exogenous gene" and "exogenous protein" indicate a nucleic acid, gene or protein, respectively, that has come from a source other than its native source, and has been artificially supplied to the biological system. In contrast, the terms "endogenous protein," "native protein," "endogenous gene," and "native gene" refer to a protein or gene that is native to the biological system, species or chromosome under study. A "native" or "endogenous" polypeptide does not contain amino acid residues encoded by recombinant vector sequences; that is, the native protein contains only those amino acids found in the polypeptide or protein as it occurs in nature. A "native" polypeptide may be produced by recombinant means or may be isolated from a naturally occurring source. Similarly, a "native" or "endogenous" gene is a gene that does not contain nucleic acid elements encoded by sources other than the chromosome on which it is normally found in nature.

As used herein, the term "portion" when in reference to a protein (as in "a portion of a given protein") refers to fragments of that protein. The fragments may range in size from four amino acid residues to the entire amino acid sequence minus one amino acid.

Nucleic acid molecules (e.g., DNA or RNA) are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element or the coding region. Transcription termination and polyadenylation signals are located 3' or downstream of the coding region.

The term "gene" refers to a nucleic acid (e.g., DNA) sequence comprised of parts, that when appropriately combined in either a native or recombinant manner, provide some product or function. Genes may or may not comprise coding sequences necessary for the production of a polypeptide. Examples of genes which do not encode polypeptide sequences include ribosomal RNA genes (rRNA) and transfer RNA (tRNA) genes. Genes can encode a polypeptide or any portion of a polypeptide within the gene's "coding region" or "open reading frame." The polypeptide produced by the open reading frame of a gene may or may not display functional activity or properties of the full-length polypeptide (e.g., enzymatic activity, ligand binding, signal transduction, etc.).

In addition to the coding region of the nucleic acid, the term "gene" also encompasses the transcribed nucleotide sequences of the full-length mRNA adjacent to the 5' and 3' ends of the coding region. These noncoding regions are variable in size, and typically extend for distances up to or exceeding 1 kb on both the 5' and 3' ends of the coding region. The sequences that are located 5' and 3' of the coding region and are contained on the mRNA are referred to as 5' and 3' untranslated sequences (5' UT and 3' UT). Both the 5' and 3' UT may serve regulatory roles, including translation initiation, post-transcriptional cleavage and polyadenylation. The term "gene" encompasses mRNA, cDNA and genomic forms of a gene.

It is contemplated that the genomic form or genomic clone of a gene may contain the sequences of the transcribed mRNA, as well as other non-coding sequences which lie outside of the mRNA. The regulatory regions which lie outside the mRNA transcription unit are sometimes called "5' or 3' flanking sequences." A functional genomic form of a gene must contain regulatory elements necessary for the regulation of transcription. The term "promoter/enhancer region" is usually used to describe this DNA region, typically but not necessarily 5' of the site of transcription initiation, sufficient to confer appropriate transcriptional regulation. The word "promoter" alone is sometimes used synonymously with "promoter/enhancer." A promoter may be constitutively active, or alternatively, conditionally active, where transcription is initiated only under certain physiological conditions or in the presence of certain drugs. The 3' flanking region may contain additional sequences which regulate transcription, especially the termination of transcription. "Introns" or "intervening regions" or "intervening sequences" are segments of a gene which are contained in the primary transcript (i.e., hetero-nuclear RNA, or hnRNA), but are spliced out to yield the processed mRNA form. Introns may contain transcriptional regulatory elements such as enhancers. The mRNA produced from the genomic copy of a gene is translated in the presence of ribosomes to yield the primary amino acid sequence of the polypeptide.

As used herein, the term "regulatory element" refers to a genetic element which controls some aspect of the expression of nucleic acid sequences. For example, a promoter is a regulatory element that enables the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis et al., *Science* 236:1237 [1987]). Promoter and enhancer elements have been isolated from a variety of eukaryotic sources including genes in yeast, insect and mammalian cells, as well as viruses. Analogous control elements (i.e., promoters and enhancers) are also found in prokaryotes. The selection of a particular promoter and enhancer to be operably linked in a recombinant gene depends on what cell type is to be used to express the protein of interest. Some eukaryotic promoters and enhancers have a broad host range while others are functional only in a limited subset of cell types (for review see, Voss et al., *Trends Biochem. Sci.*, 11:287 [1986] and Maniatis et al., *Science* 236:1237 [1987]). For example, the SV40 early gene enhancer is very active in a wide variety of mammalian cell types (Dijkema et al., *EMBO J.*, 4:761 [1985]). Two other examples of promoter/enhancer elements active in a broad range of mammalian cell types are those from the human elongation factor 1α gene (Uetsuki et al., *J. Biol. Chem.*, 264:5791 [1989]; Kim et al., *Gene* 91:217 [1990]; Mizushima and Nagata, *Nuc. Acids. Res.*, 18:5322 [1990]), the long terminal repeats of the Rous sarcoma virus (Gorman et al., *Proc. Natl. Acad. Sci. USA* 79:6777 [1982]), and human cytomegalovirus (Boshart et al., *Cell* 41:521 [1985]). Some promoter elements serve to direct gene expression in a tissue-specific manner.

As used herein, the term "promoter/enhancer" denotes a segment of DNA which contains sequences capable of providing both promoter and enhancer functions (i.e., the functions provided by a promoter element and an enhancer element). For example, the long terminal repeats of retroviruses contain both promoter and enhancer functions. The promoter/enhancer may be "endogenous," or "exogenous," or "heterologous." An "endogenous" promoter/enhancer is one which is naturally linked with a given gene in the genome. An "exogenous" or "heterologous" promoter/enhancer is one placed in juxtaposition to a gene by means of genetic manipulation (i.e., molecular biological techniques such as cloning and recombination) such that transcription of the gene is controlled by the linked promoter/enhancer.

The presence of "splicing signals" on an expression vector often results in higher levels of expression of the recombinant transcript. Splicing signals mediate the removal of introns from the primary RNA transcript and consist of a splice donor and acceptor site (See e.g., Sambrook et al., *Molecular Cloning: A Laboratory Manual*, Second Edition, Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires the presence of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a nucleic acid sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (See e.g., Sambrook et al., *Molecular Cloning: A Laboratory Manual*, Second Edition, Cold Spring Harbor Laboratory Press, New York [1989], pp. 16.6–16.7).

The terms "in operable combination," "in operable order," "operably linked" and similar phrases when used in reference to nucleic acid herein are used to refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the terms "an oligonucleotide having a nucleotide sequence encoding a gene," "polynucleotide having a nucleotide sequence encoding a gene," and similar phrases are meant to indicate a nucleic acid sequence comprising the coding region of a gene (i.e., the nucleic acid sequence which encodes a gene product). The coding region may be present in either a cDNA, genomic DNA or RNA form. When present in a DNA form, the oligonucleotide, polynucleotide or nucleic acid may be single-stranded (i.e., the sense strand or the antisense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the terms "nucleic acid molecule encoding," "DNA sequence encoding," and "DNA encoding" and similar phrases refer to the order or sequence of deoxyribonucleotides along a strand of deoxyribonucleic acid. The order of these deoxyribonucleotides determines the order of amino acids along the polypeptide (e.g., protein) chain. The DNA sequence thus codes for the amino acid sequence.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of the mRNA. Gene expression can be regulated at many stages. "Up-regulation" or "activation" refers to regulation that increases the production of gene expression products (i.e., RNA or protein), while "down-regulation" or "repression" refers to regulation that decreases mRNA or protein production. Molecules (e.g., transcription factors) that are involved in up-regulation or down-regulation are often called "activators" and "repressors," respectively.

As used herein, the terms "complementary" or "complementarity" are used in reference to polynucleotides (i.e., a sequence of nucleotides) related by the rules of antiparallel base-pairing. For example, the sequence 5'-C-T-A-G-T-3' is complementary to the sequence 5'-A-C-T-A-G-3'. Complementarity may be "partial," in which only some of the nucleic acids' bases are matched according to antiparallel base pairing rules. Also, there may be "complete" or "total" complementarity between two nucleic acids. The degree of complementarity between nucleic acid strands has significant effects on the efficiency and strength of hybridization between nucleic acid strands. This is of particular importance in polymerase chain reaction (PCR) amplification reactions, as well as detection methods that depend upon binding between nucleic acids. As used herein, the terms "antiparallel complementarity" and "complementarity" are synonymous.

As used herein, the term "antisense" is used in reference to any nucleic acid which is antiparallel to and complementary to another nucleic acid. Antisense DNA or RNA may be produced by any method. For example, a cDNA or a portion of a cDNA may be subcloned into an expression vector containing a promoter which permits transcription either in vitro or in vivo. The cDNA or a portion of the cDNA is subcloned in such a way that it is in the reverse orientation relative to the direction of transcription of the cDNA in its native chromosome. Transcription of this antisense cDNA produces an RNA transcript that is complementary and antiparallel to the native mRNA. The mechanism by which an antisense nucleic acid produces effects in a biological system is unclear, however, likely involves the formation of a duplex with its complementary nucleic acid within either the nucleus or cytoplasm of a cell. These duplexes are theorized to block transcription of the native mRNA or prevent its translation. Using antisense techniques, an "artificial knockout" mutant may be reproduced in an animal or animal cell line. The term "antisense strand" is used in reference to a nucleic acid strand that is complementary to the "sense" strand. The designation (−) (i.e., "negative") is sometimes used in reference to the antisense strand, with the designation (+) (i.e., "positive") sometimes used in reference to the sense strand.

The following definitions are the commonly accepted definitions of the terms "identity," "similarity" and "homology." Percent identity is a measure of strict amino acid conservation. Percent similarity is a measure of amino acid conservation which incorporates both strictly conserved amino acids, as well as "conservative" amino acid substitutions, where one amino acid is substituted for a different amino acid having similar chemical properties (i.e. a "conservative" substitution). The term "homology" can pertain to either proteins or nucleic acids. Two proteins can be described as "homologous" or "non-homologous," but the degree of amino acid conservation is quantitated by percent identity and percent similarity. Nucleic acid conservation is measured by the strict conservation of the bases adenine, thymine, guanine and cytosine in the primary nucleotide sequence. When describing nucleic acid conservation, conservation of the nucleic acid primary sequence is sometimes expressed as percent homology. In the same nucleic acid, one region may show a high percentage of nucleotide sequence conservation, while a different region can show no or poor conservation. Nucleotide sequence conservation can not be inferred from an amino acid similarity score. Two proteins may show domains that in one region are homologous, while other regions of the same protein are clearly non-homologous.

As used herein, the term "hybridization" is used in reference to the pairing of complementary nucleic acids. Hybridization can be demonstrated using a variety of hybridization assays (Southern blot, Northern Blot, slot blot, phage plaque hybridization, and other techniques). These protocols are common in the art (See e.g., Sambrook et al. (eds.), *Molecular Cloning: A Laboratory Manual*, Second Edition, Volumes 1–3, Cold Spring Harbor Laboratory Press, NY, [1989]; Ausubel et al. (eds.), *Current Protocols in Molecular Biology*, Vol. 1–4, John Wiley & Sons, Inc., New York [1994]). Hybridization is the process of one nucleic acid pairing with an antiparallel counterpart which may or may not have 100% complementarity. Two nucleic acids which contain 100% antiparallel complementarity will show strong hybridization. Two antiparallel nucleic acids which contain no antiparallel complementarity (generally considered to be less than 30%) will not hybridize. Two nucleic acids which contain between 31–99% complementarity will show an intermediate level of hybridization. A single molecule that contains pairing of complementary nucleic acids within its structure is said to be "self-hybridized."

As used herein, the term "stringency" is used in reference to the conditions of temperature, ionic strength, and the presence of other compounds such as organic solvents, under which nucleic acids hybridize. "Low or weak stringency" conditions are reaction conditions which favor the complementary base pairing and annealing of two nucleic acids. "High stringency" conditions are those conditions which are less optimal for complementary base pairing and annealing. The art knows well that numerous variables affect the strength of hybridization, including the length and nature of the probe and target (DNA, RNA, base composition, present in solution or immobilized, the degree of complementary between the nucleic acids, the $T_m$ of the formed hybrid, and the G:C ratio within the nucleic acids). Conditions may be manipulated to define low or high stringency conditions: factors such as the concentration of salts and other components in the hybridization solution (e.g., the presence or absence of formamide, dextran sulfate, polyethylene glycol) as well as temperature of the hybridization and/or wash steps. Conditions of "low" or "high" stringency are specific for the particular hybridization technique used.

During hybridization of two nucleic acids under high stringency conditions, complementary base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less. As used herein, two nucleic acids which are able to hybridize under high stringency conditions are considered "substantially homologous."

Whether sequences are "substantially homologous" may be verified using hybridization competition assays. For example, a "substantially homologous" nucleotide sequence is one that at least partially inhibits a completely complementary probe sequence from hybridizing to a target nucleic acid under conditions of low stringency. This is not to say that conditions of low stringency are such that non-specific binding is permitted; low stringency conditions require that the binding of two sequences to one another be a specific (i.e., selective) interaction. The absence of non-specific binding may be verified by the use of a second target that lacks even a partial degree of complementarity (e.g., less than about 30% identity); in the absence of non-specific binding the probe will not hybridize to the second non-complementary target. When used in reference to a double-stranded nucleic acid sequence such as a cDNA or genomic clone, the term "substantially homologous" refers to any probe that can hybridize to either or both strands of the double-stranded nucleic acid sequence under conditions of high stringency.

A gene may produce multiple RNA species that are generated by differential splicing of the primary RNA transcript. cDNAs that are splice variants of the same gene contain regions of nucleotide sequence identity (100% homology), representing the presence of the same exon or portion of the same exon on both cDNAs, as well as regions of complete non-identity. Because the two cDNAs contain regions of sequence identity they will both hybridize to a probe derived from the entire gene or portions of the gene containing sequences found on both cDNAs. As used herein, the two splice variants are therefore substantially homologous to such a probe and to each other.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein, the term "amplifiable nucleic acid" is used in reference to nucleic acids which may be amplified by any amplification method. It is contemplated that "amplifiable nucleic acid" will usually comprise "template." As used herein, the term "template" refers to nucleic acid originating from a sample that is to be used as a substrate for the generation of the amplified nucleic acid.

As used herein, the term "primer" refers to an oligonucleotide, typically but not necessarily produced synthetically, that is capable of acting as a point of initiation of nucleic acid synthesis when placed under conditions in which synthesis of a primer extension product that is complementary to a nucleic acid strand is induced, (i.e., in the presence of nucleotides, an inducing agent such as DNA polymerase, and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether produced as a purified restriction digest or produced by synthetic means, recombinantly or by amplification, that is capable of hybridizing to another oligonucleotide of interest. A probe may be single-stranded or double-stranded. Probes are useful in the detection, identification and isolation of particular gene sequences. It is contemplated that in preferred embodiments, any probe used in the present invention will be labelled with any "reporter molecule," so that it is detectable in any detection system, including, but not limited to enzyme (e.g., ELISA, as well as immunohistochemical assays), fluorescent, radioactive, and luminescent systems. It is not intended that the present invention be limited to any particular detection system or label.

As used herein, the term "polymerase chain reaction" ("PCR") refers to the method of K. B. Mullis U.S. Pat. Nos. 4,683,195, 4,683,202 and 4,965,188, each of which is hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a thermostable DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labelled probe; incorporation of biotinylated primers followed by avidin-enzyme conjugate detection; incorporation of $^{32}$P-labelled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (e.g., deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The term "isolated" when used in relation to a nucleic acid, as in "an isolated nucleic acid," "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from the form or setting of that nucleic acid found in nature. In contrast, non-isolated nucleic acids are found in the state in which they exist in nature. For example, a given DNA sequence (e.g., a gene) is found on the host cell chromosome in proximity to neighboring genes; RNA sequences, such as a specific mRNA sequence encoding a specific protein, are found in the cell in a mixture with numerous other mRNAs that encode a multitude of proteins. However, isolated nucleic acid encoding a given polypeptide includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of contaminants from a sample. For example, antibodies are purified by removal of contaminating non-immunoglobulin proteins; they are also purified by the removal of immunoglobulin that does not bind to the target molecule. The removal of non-immnunoglobulin proteins and/or the removal of immunoglobulins that do not bind to the target molecule results in an increase in the percent of target-reactive inmmunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "vector" is used in reference to nucleic acid molecules that transfer DNA segment(s) from one cell to another. The term "vehicle" is sometimes used interchangeably with "vector." A vector "backbone" comprises those parts of the vector which mediate its maintenance and enable its intended use (e.g., the vector backbone may contain sequences necessary for replication, genes imparting drug or antibiotic resistance, a multiple cloning site, and possibly operably linked promoter/enhancer elements which enable the expression of a cloned nucleic acid). The cloned nucleic acid (e.g., such as a cDNA coding sequence, or an amplified PCR product) is inserted into the vector backbone using common molecular biology techniques. Vectors are often derived from plasmids, bacteriophages, or plant or animal viruses. A "cloning vector" or "shuttle vector" or "subcloning vector" contain operably linked parts which facilitate subcloning steps (e.g., a multiple cloning site containing multiple restriction endonuclease sites). A "recombinant vector" indicates that the nucleotide sequence or arrangement of its parts is not a native configuration, and has been manipulated by molecular biological techniques. The term implies that the vector is comprised of segments of DNA that have been artificially joined.

The term "expression vector" as used herein refers to a recombinant DNA molecule containing a desired coding sequence and operably linked nucleic acid sequences necessary for the expression of the operably linked coding sequence in a particular host organism (e.g., a bacterial expression vector, a yeast expression vector or a mammalian expression vector). Nucleic acid sequences necessary for expression in prokaryotes typically include a promoter, an operator (optional), and a ribosome binding site, often along with other sequences. Eukaryotic cells utilize promoters, enhancers, and termination and polyadenylation signals and other sequences which are different from those used by prokaryotes.

Eukaryotic expression vectors may also contain "viral replicons" or "viral origins of replication." Viral replicons are viral DNA sequences that allow for the extrachromosomal replication of a vector in a host cell expressing the appropriate replication factors. Some vectors replicate their nucleic acid to high copy numbers (e.g., vectors that contain either the SV40 or polyoma virus origin of replication replicate to high "copy number" (up to $10^4$ copies/cell) in cells that express the appropriate viral T antigen). Other vectors replicate their nucleic acid in low copy numbers (e.g., vectors that contain the replicons from bovine papillomavirus or Epstein-Barr virus replicate extrachromosomally at "low copy number" (~100 copies/cell)). The viral origins of replication listed above are not limiting, as the art is aware of other origins of replication that are commonly used in eukaryotic expression vectors.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

Embryonal cells at various developmental stages can be used to introduce transgenes for the production of transgenic, non-human animals. Different methods are used depending on the stage of development of the embryonic cell. The zygote is the best target for micro-injection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage (Brinster et al., *Proc. Natl. Acad. Sci. USA* 82:4438–4442 [1985]). As a consequence, all cells of the transgenic non-human animal will carry the incorporated transgene. This will, in general, also be reflected in the efficient transmission of the transgene to offspring of the founder since 50% of the germ cells will harbor the transgene. Micro-injection of zygotes is the preferred method for incorporating transgenes in practicing the invention. U.S. Pat. No. 4,873,191, herein incorporated by reference, describes a method for the micro-injection of zygotes.

Retroviral infection can also be used to introduce transgenes into a non-human animal. The developing embryo can be cultured in vitro to the blastocyst stage. During this time, the blastomeres can be targets for retroviral infection (Jaenisch, *Proc. Natl. Acad. Sci. USA* 73:1260–1264 [1976]). Efficient infection of the blastomeres is obtained by enzymatic treatment to remove the zona pellucida (See e.g., Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., *Proc. Natl. Acad Sci. USA* 82:6927–693 [1985]). Transfection is easily and efficiently obtained by culturing the blastomeres on a monolayer of virus-producing cells (van der Putten, *Proc. Natl. Acad. Sci. USA* 82(18):6148–52 [1985]; and Stewart, et al., *EMBO J.* 6:383–388 [1987]). Alternatively, infection can be performed at a later stage. Virus or virus-producing cells can be injected into the blastocoele (Jahner et al., *Nature* 298: 623–628 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jauner et al., *Nature* 298:623–628 [1982]). Additional means of using retroviruses or retroviral vectors to create transgenic animals known to the art include, but are not limited to, the micro-injection of retroviral particles or mitomycin C-treated cells producing retrovirus into the perivitelline space of fertilized eggs or early embryos (PCT International Application WO 90/08832 [1990], and Haskell and Bowen, *Mol. Reprod. Dev.*, 40:386 [1995]).

A third type of target cell for transgene introduction is the embryonal stem (ES) cell. ES cells are obtained by culturing pre-implantation embryos in vitro under appropriate conditions (Evans et al., *Nature* 292:154–156 [1981]; Bradley et al., *Nature* 309:255–258 [1984]; Gossler et al., *Proc. Acad. Sci. USA* 83:9065–9069 [1986]; and Robertson et al., *Nature* 322:445–448 [1986]). Transgenes can be efficiently introduced into the ES cells by DNA transfection using a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, see Jaenisch, *Science* 240:1468–1474 [1988]). Prior to the introduction of transfected ES cells into the blastocoel, the transfected ES cells may be subjected to various selection protocols to enrich for ES cells that have integrated the transgene, assuming that the transgene provides a means for such selection. Alternatively, PCR may be used to screen for ES cells that have integrated the transgene. This technique obviates the need for growth of the transfected ES cells under appropriate selective conditions prior to transfer into the blastocoel.

The terms "overexpression" and "overexpressing" and grammatical equivalents are used in reference to levels of mRNA or protein where the level of expression of the mRNA or protein is higher than that typically observed in a given tissue in a control or non-transgenic animal. Levels of mRNA or protein are measured using any of a number of techniques known to those skilled in the art. For example, mRNA levels may be assayed using (but not limited to) a Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quatntification of the expression of the transgenic mRNA.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Mammalian cell transfection-techniques are common in the art, and are described in many sources (See, e.g., Ausubel et al. (eds.), *Current Protocols in Molecular Biology*, Vol. 1–4, John Wiley & Son, Inc., New YorK [1994]).

The term "stable transfection" or "stably transfected" refers to the introduction and integration of foreign DNA into the genome of the transfected cell. The term "stable transfectant" refers to a cell which contains stably integrated foreign DNA within its own genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a eukaryotic cell, and most typically mammalian cells. The uptake of nucleic acids by cells is enhanced when the nucleic acid is presented as a calcium phosphate-nucleic acid co-precipitate. Various modifications of the original technique of Graham and van der Eb (Graham and van der Eb, *Virol.*, 52:456 [1973]) are known in which the conditions for the transfection of a particular cell type has been optimized. The art is well aware of these various methods.

The term "transformation" has multiple meanings, depending on its usage. In one sense, the term "transformation" is used to describe the process of introduction of foreign DNA into prokaryotic cells (i.e., bacterial cells), and most frequently *E. coli* strains. Bacterial cell transformation may be accomplished by a variety of means well known to the art, including the preparation of "competent" bacteria by the use of calcium chloride, magnesium chloride or rubidium chloride, and electroporation. When a plasmid is used as the transformation vector, the plasmid typically contains a gene conferring drug resistance, such as the genes encoding ampicillin, tetracycline or kanamycin resistance. Bacterial transformation techniques are common in the art, and are described in many sources (e.g., Cohen et al., *Proc. Natl. Acad. Sci. USA* 69: 2110–2114 [1972]; Hanahan, *J. Mol. Biol.*, 166:557–580 [1983]; Sambrook et al. (eds.), *Molecular Cloning: A Laboratory Manual*, Second Edition, Volumes 1–3, Cold Spring Harbor Laboratory Press, NY, [1989]; Ausubel et al. (eds.), *Current Protocols in Molecular Biology*, Vol. 1–4, John Wiley & Sons, Inc., New York [1994]).

"Transformation" also describes the physiological process by which a normal eukaryotic cell acquires the phenotypic qualities of a malignant cell. Such properties can include the ability to grow in soft agar, the ability to grow in nutrient poor conditions, rapid proliferation, and the loss of contact inhibition. A eukaryotic cell which is "transformed" displays the properties of malignant cells. A eukaryotic cell may acquire its transformed phenotype in vivo, or be artificially transformed in culture.

As used herein, the term "selectable marker" refers to the use of a gene that encodes an enzymatic activity that confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed. Furthermore, selectable markers may be "dominant." Dominant selectable markers encode an enzymatic activity that can be detected in any eukaryotic cell line. Examples of dominant selectable markers include the bacterial aminoglycoside 3' phosphotransferase gene (i.e., the neo gene) that confers resistance to the drug G-418 in mammalian cells, as well as the bacterial hygromycin G phosphotransferase (hyg) gene that confers resistance to the antibiotic hygromycin, and the bacterial xanthine-guanine phosphoribosyl transferase gene (i.e., the gpt gene) that confers the ability to grow in the presence of mycophenolic acid. The use of non-dominant selectable markers must be in conjunction with a cell line that lacks the relevant enzyme activity. Examples of non-dominant selectable markers include the thymidine kinase (tk) gene (used in conjunction with tk$^-$ cell lines), the CAD gene (used in conjunction with CAD-deficient cells) and the mammalian hypoxanthine-guanine phosphoribosyl transferase (hprt) gene (used in conjunction with hprt$^-$ cell lines). A review of the use of selectable markers in mammalian cell lines is provided in Sambrook et al., *Molecular Cloning: A Laboratory Manual*, Second Edition, Cold Spring Harbor Laboratory Press, New York (1989), at pp. 16.9–16.15.

As used herein in the context of protein purification, the terms "source culture," "starting culture," "starting material" or "culture" or the like can include any of the following materials: culture supernatant, cultured eukaryotic or prokaryotic cells (e.g., animal cells or bacteria), crushed eukaryotic or prokaryotic cells, tissue removed from an organism, or the product of an in vitro translation or in vitro coupled transcription/translation reaction. The cells of such a culture may or may not contain recombinant nucleic acid.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The term "test compound" refers to any chemical entity, pharmaceutical, drug, composition, and the like that can be used to treat or prevent a disease, illness, sickness, or disorder of bodily function. Test compounds comprise both known and potential therapeutic compounds. A "known therapeutic compound" refers to a therapeutic compound that has been previously described. Particularly preferred known therapeutics are those that have been shown (e.g., through animal trials or prior experience with administration to humans) to be effective in treatment or prevention of pathology.

As used herein, a "drug" can be any molecule of any composition, including protein, peptide, nucleic acid, organic molecule, inorganic molecule, or combinations of molecules, biological or non-biological, which are capable of producing a physiological response. As used herein, a "drug" provides at least one beneficial response in the cure, mitigation, treatment or prevention of a disease or disorder. A compound is considered a "drug candidate" if it is not yet known if that compound will provide at least one beneficial response in the cure, mitigation, treatment or prevention of a disease, disorder or condition. A "drug library" is a collection of molecules, where it may or may not be known if one or multiple drugs in the library have therapeutic value.

As used herein, the terms "host," "expression host," and "transformant" refer to organisms and/or cells which harbor an exogenous DNA sequence (e.g., via transfection), an expression vector or vehicle, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host.

As used herein, the term "subject" refers to any animal being examined, studied or treated. It is not intended that the present invention be limited to any particular type of subject. It is contemplated that multiple organisms will find use in the present invention as subjects. In some embodiments, humans are the preferred subject.

A subject displaying pathology resulting from abnormal cytokine activity may display symptoms that include, but are not limited to, inflammation, cachexia, insulin resistance, overstimulation of interleukin-6 and granulocyte/macrophage-colony stimulating factor (GM-CSF) secretion, enhanced cytotoxicity of polymorphonuclear neutrophils, prolonged expression of cellular adhesion molecules, induction of procoagulant activity on vascular endothelial cells, increased adherence of neutrophils and lymphocytes, stimulation of the release of platelet activating factor from macrophages, neutrophils and vascular endothelial cells, fever, malaise, and anorexia.

As used herein, a "disease" is a disruption of normal body function, generally where two of three criteria are met: 1) the etiological agent is known, 2) an identifiable group of symptoms appears, and 3) there are consistent anatomical or physiological alterations. Examples include, but are not limited to rheumatoid arthritis, inflammatory bowel disease and graft-versus-host disease. A disorder is, in general, a disruption of some aspect of normal body function (e.g., rheumatoid arthritis and inflammatory bowel disease are immune disorders).

As used herein, the term "antigen" refers to any agent (e.g., any substance, compound, molecule [including macromolecules], or other moiety), that is recognized by an antibody, while the term "immunogen" refers to any agent (e.g., any substance, compound, molecule [including macromolecules], or other moiety) that can elicit an immunological response in an individual. These terms may be used to refer to an individual macromolecule or to a homogeneous or heterogeneous population of antigenic macromolecules. It is intended that the terms antigen and immunogen encompass protein molecules or at least one portion of a protein molecule, which contains one or more epitopes. In many cases, antigens are also immunogens, thus the term "antigen" is often used interchangeably with the term "immunogen." The substance may then be used as an antigen in an assay to detect the presence of appropriate antibodies in the serum of the immunized animal.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general.

As used herein, the term "adjuvant" is defined as a substance known to increase the immune response to other antigens when administered with other antigens. If adjuvant is used, it is not intended that the present invention be limited to any particular type of adjuvant—or that the same adjuvant, once used, be used all the time. It is contemplated that adjuvants may be used either separately or in combination. The present invention contemplates all types of adjuvant, including but not limited to agar beads, aluminum hydroxide or phosphate (alum), Incomplete Freund's adjuvant (incomplete or complete), as well as Quil A adjuvant and Gerbu adjuvant (Accurate Chemical and Scientific Corporation), and bacterins (i.e., killed preparations of bacterial cells). It is further contemplated that the vaccine comprise at least one "excipient" (i.e., a pharmaceutically acceptable carrier or substance) suitable for administration to a human or other animal subject. It is intended that the term "excipient" encompass liquids, as well as solids, and colloidal suspensions.

As used herein the term "immunogenically-effective amount" refers to that amount of an immunogen required to invoke the production of protective levels of antibodies in a host upon vaccination.

The term "protective level," when used in reference to the level of antibodies induced upon immunization of the host with an immunogen means a level of circulating antibodies sufficient to protect the host from challenge with a lethal dose of an organism or other material (e.g., toxins, etc.).

The terms "self antigen" or "autoantigen" refer to an antigen or a molecule normally expressed by an individual, but which solicits an immune response. Under normal conditions, these autoantigens are recognized during an immune response as self (i.e., an antigen that is normally part of the individual), and do not solicit an immune response. This is in contrast to antigens which are foreign, or exogenous, and are thus not normally part of the individual's antigenic makeup. "Self antigen" or "autoantigen" is recognized as foreign, although the antigen is native to the individual's physiology.

As used herein, the term "autoimmune disease" means a set of sustained organ-specific or systemic clinical symptoms and signs associated with altered immune homeostasis that is manifested by qualitative and/or quantitative defects of expressed autoimmune repertoires. Autoimmune diseases are characterized by antibody or cytotoxic immune responses to epitopes on self antigens. The immune system of the individual then activates an inflammatory cascade aimed at cells and tissues presenting those specific self antigens. The destruction of the antigen, tissue, cell type, or organ attacked by the individual's own immune system gives rise to the signs and symptoms of the disease. Clinically significant autoimmune diseases include, for example, rheumatoid arthritis, multiple sclerosis, juvenile-onset diabetes, systemic lupus erythematosus (SLE), autoimmune uveoretinitis, autoimmune vasculitis, bullous pemphigus, myasthenia gravis, autoimmune thyroiditis or Hashimoto's disease, Sjogren's syndrome, granulomatous orchitis, autoimmune oophoritis, Crohn's disease, sarcoidosis, rheumatic carditis, ankylosing spondylitis, glomerulonephritis, Grave's disease, and autoimmune thrombocytopenic purpura.

The ability of a particular antigen to stimulate a cell-mediated immunological response may be determined by a number of assays, including but not limited to lymphoproliferation (ie., lymphocyte activation) assays, CTL cytotoxic cell assays such as chromium-release assays, or by assaying for T lymphocytes specific for the antigen in a sensitized subject. Such assays are well known in the art (See e.g., Erickson et al., *J. Immunol.*, 151:4189–4199 [1993] and Doe et al., *Eur. J. Immunol.*, 24:2369–2376 [1994]).

The term "modulate," as used herein, refers to a change in the biological activity of a biologically active molecule. Modulation can be an increase or a decrease in activity, a change in binding characteristics, or any other change in the biological, functional, or immunological properties of biologically active molecules.

The term "agonist," as used herein, refers to a molecule which, when interacting with an biologically active molecule, causes a change (e.g., enhancement) in the biologically active molecule, which modulates the activity of the biologically active molecule. Agonists may include proteins, nucleic acids, carbohydrates, or any other molecules which bind or interact with biologically active molecules. For example, agonists can alter the activity of gene transcription by interacting with RNA polymerase directly or through a transcription factor.

The terms "antagonist" or "inhibitor," as used herein, refer to a molecule which, when interacting with a biologically active molecule, blocks or modulates the biological activity of the biologically active molecule. Antagonists and inhibitors may include proteins, nucleic acids, carbohydrates, or any other molecules that bind or interact with biologically active molecules. Inhibitors and antagonists can effect the biology of cells, tissues, organs or entire organisms.

The terms "Western blot," "Western immunoblot" "immunoblot" and "Western" refer to the immunological analysis of protein(s), polypeptides or peptides that have been immobilized onto a membrane support. The proteins are first resolved by polyacrylamide gel electrophoresis (i.e., SDS-PAGE) to separate the proteins, followed by transfer of the protein from the gel to a solid support, such as nitrocellulose or a nylon membrane. The immobilized proteins are then exposed to an antibody having reactivity towards an antigen of interest. In preferred embodiments, the binding of the antibody (i.e., the primary antibody) is detected by use of a secondary antibody which specifically binds the primary antibody. The secondary antibody is typically conjugated to an enzyme which permits visualization of the antigen-antibody complex by the production of a colored reaction product or catalyzes a luminescent enzymatic reaction (e.g., the ECL reagent, Amersham).

As used herein, the term "ELISA" refers to enzyme-linked immunosorbent assay (or EIA). Numerous ELISA methods and applications are known in the art, and are described in many references (See e.g., Crowther, "Enzyme-Linked Immunosorbent Assay (ELISA)," in *Molecular Biomethods Handbook*, Rapley et al. [eds.], pp. 595–617, Humana Press, Inc., Totowa, N.J. [1998]; See also, Harlow and Lane (eds.), *Antibodies: A Laboratory Manual*, Cold Spring Harbor Laboratory Press [1988]; and Ausubel et al. (eds.), *Current Protocols in Molecular Biology*, Ch. 11, John Wiley & Sons, Inc., New York [1994], for general descriptions of ELISA methodology). In addition, there are numerous commercially available ELISA test systems, equipment and individual reagents.

One ELISA method is a "direct ELISA," where an antigen (e.g., sTNFR1 or ARTS-1) in a sample is detected. In one embodiment of the direct ELISA, a sample containing antigen is exposed to a solid (i.e., stationary or immobilized) support (e.g., a microtiter plate well). The antigen within the sample becomes immobilized to the stationary phase, and is detected directly using an enzyme-conjugated antibody specific for the antigen.

In an alternative embodiment, an antibody specific for an antigen is detected in a sample. In this embodiment, a sample containing an antibody (e.g., anti-ARTS-1 antiserum) is immobilized to a solid support (e.g., a microtiter plate well). The antigen-specific antibody is subsequently detected using purified antigen and an enzyme-conjugated antibody specific for the antigen.

In further alternative embodiments, an "indirect ELISA" is used to detect antibody or antigen in samples. In one embodiment, an antigen (or antibody) is immobilized to a solid support (e.g., a microtiter plate well) as in the direct ELISA, but is detected indirectly by first adding an antigen-specific antibody (or antigen), then followed by the addition of a detection antibody specific for the antibody that specifically binds the antigen, also known as "species-specific" antibodies (e.g., a goat anti-rabbit antibody), which are available from various manufacturers known to those in the art (e.g., Santa Cruz Biotechnology; Zymed and Pharmingen/Transduction Laboratories).

In other embodiments, a "sandwich ELISA" is used, where the antigen is immobilized on a solid support (e.g., a microtiter plate) via an antibody (i.e., a capture antibody) that is immobilized on the solid support and is able to bind the antigen of interest. Following the affixing of a suitable capture antibody to the immobilized phase, a sample is then added to the microtiter plate well, followed by washing. If the antigen of interest is present in the sample, it is bound to the capture antibody present on the support. In some embodiments, a sandwich ELISA is a "direct sandwich" ELISA, where the captured antigen is detected directly by using an enzyme-conjugated antibody directed against the antigen. Alternatively, in other embodiments, a sandwich ELISA is an "indirect sandwich" ELISA, where the captured antigen is detected indirectly by using an antibody directed against the antigen, which is then detected by another enzyme-conjugated antibody which binds the antigen-specific antibody, thus forming an antibody-antigen-antibody-antibody complex. Suitable reporter reagents are then added to detect the third antibody. Alternatively, in some embodiments, any number of additional antibodies are added as necessary, in order to detect the antigen-antibody complex. In some preferred embodiments, these additional antibodies are labelled or tagged, so as to permit their visualization and/or quantitation.

As used herein, the term "capture antibody" refers to an antibody that is used in a sandwich ELISA to bind (i.e., capture) an antigen in a sample prior to detection of the antigen. In one embodiment of the present invention, biotinylated capture antibodies are used in the present invention in conjunction with avidin-coated solid support. Another antibody (i.e., the detection antibody) is then used to bind and detect the antigen-antibody complex, in effect forming a "sandwich" comprised of antibody-antigen-antibody (i.e., a sandwich ELISA).

As used herein, a "detection antibody" is an antibody which carries a means for visualization or quantitation.

Typically, detection antibodies are conjugated enzyme moieties that yield a colored, fluorescent, or luminescent reaction product following the addition of a suitable substrate. Conjugated enzymes commonly used with detection antibodies in the ELISA include, but are not limited to horseradish peroxidase, urease, alkaline phosphatase, glucoamylase and β-galactosidase. In some embodiments, the detection antibody is directed against the antigen of interest, while in other embodiments, the detection antibody is not directed against the antigen of interest. Thus, in some embodiments, the detection antibody is directed against another antibody. In some embodiments, the detection antibody is an anti-species antibody. Alternatively, the detection antibody is prepared with a label (e.g., biotin, a fluorescent marker, or a radioisotope), and is detected and/or quantitated using this label.

As used herein, the terms "reporter reagent," "reporter molecule," "detection substrate" and "detection reagent" are used in reference to reagents which permit the detection and/or quantitation of an antibody bound to an antigen. For example, in some embodiments, the reporter reagent is a colorimetric substrate for an enzyme that has been conjugated to an antibody. Addition of a suitable substrate to the antibody-enzyme conjugate results in the production of a colorimetric, flubrimetric, or luminescent signal (e.g., following the binding of the conjugated antibody to the antigen of interest). Other reporter reagents include, but are not limited to, radioactive compounds. This definition also encompasses the use of biotin and avidin-based compounds (e.g., including but not limited to neutravidin and streptavidin) as part of the detection system.

As used herein, the term "signal" is used generally in reference to any detectable process that indicates that a reaction has occurred, for example, binding of antibody to antigen. It is contemplated that signals in the form of radioactivity, fluorimetric or colorimetric products/reagents will all find use with the present invention. In various embodiments of the present invention, the signal is assessed qualitatively, while in alternative embodiments, the signal is assessed quantitatively.

As used herein, the term "amplifier" is used in reference to a system which enhances the signal in a detection method, such as an ELISA (e.g., an alkaline phosphatase amplifier system used in an ELISA).

As used herein, the term "solid support" is used in reference to any solid or stationary material to which reagents such as antibodies, antigens, and other test components are attached. For example, in preferred ELISA methods, the wells of microtiter plates provide solid supports. Other examples of solid supports include microscope slides, coverslips, beads, particles, cell culture flasks, as well as any other suitable items.

As used herein, the term "kit" is used in reference to a combination of reagents and other materials which facilitate sample analysis. In various embodiments of the present invention, a kit can include antibodies (e.g., a suitable capture antibody, reporter antibody, primary antibody, secondary antibody, detection antibody) purified control antigen, detection reagents, amplifier system, and nucleic acid probes. Furthermore, in other embodiments, the kit includes, but is not limited to, components such as apparatus for sample collection, sample tubes, holders, trays, racks, dishes, plates, instructions on the use of the kit, solutions or other chemical reagents, and samples to be used for standardization, normalization, and/or control samples. It is contemplated that kits of the present invention can also include apparatus and reagents for electrophoresis and blotting.

As used herein, the term "in vitro" refers to an artificial environment and to processes or reactions that occur within an artificial environment. In vitro environments consist of, but are not limited to, controlled laboratory conditions. The term "in vivo" refers to the natural environment (e.g., an animal or a cell) and to processes or reactions that occur within that natural environment.

As used herein, the terms "local" or "localized" and the like refer to confinement to a small area, a single tissue, a single organ (e.g., a lung) or other defined structure.

As used herein, the term "localized delivery" is delivery of an agent (e.g. a gene therapy agent or a drug) to a small area, a single tissue, a single organ or other specific structure. For example, localized delivery of a gene therapy agent to a single site (e.g., the liver) in a subject is typically achieved by injection into that site.

As used herein, the term "systemic" refers to multiple sites, tissues or organs in an organism, or to the entire organism. Use of the word "systemic" generally indicates involvement of the circulatory or lymphatic systems.

As used herein, the term "systemic delivery" (in contrast to localized delivery) is delivery of an agent (e.g., a drug) to multiple sites, tissues or organs in an organism, or to the entire organism via the circulatory system following an intravenous injection, or via gastrointestinal absorption of an orally administered agent.

As used herein, the term "surgical delivery" refers to the delivery of an agent (e.g., a gene therapy agent) by surgical means (i.e., by operation or some other invasive manipulation). Thus, in some embodiments, surgical techniques provide means for localized delivery of an agent.

DESCRIPTION OF THE INVENTION

Figure 1:
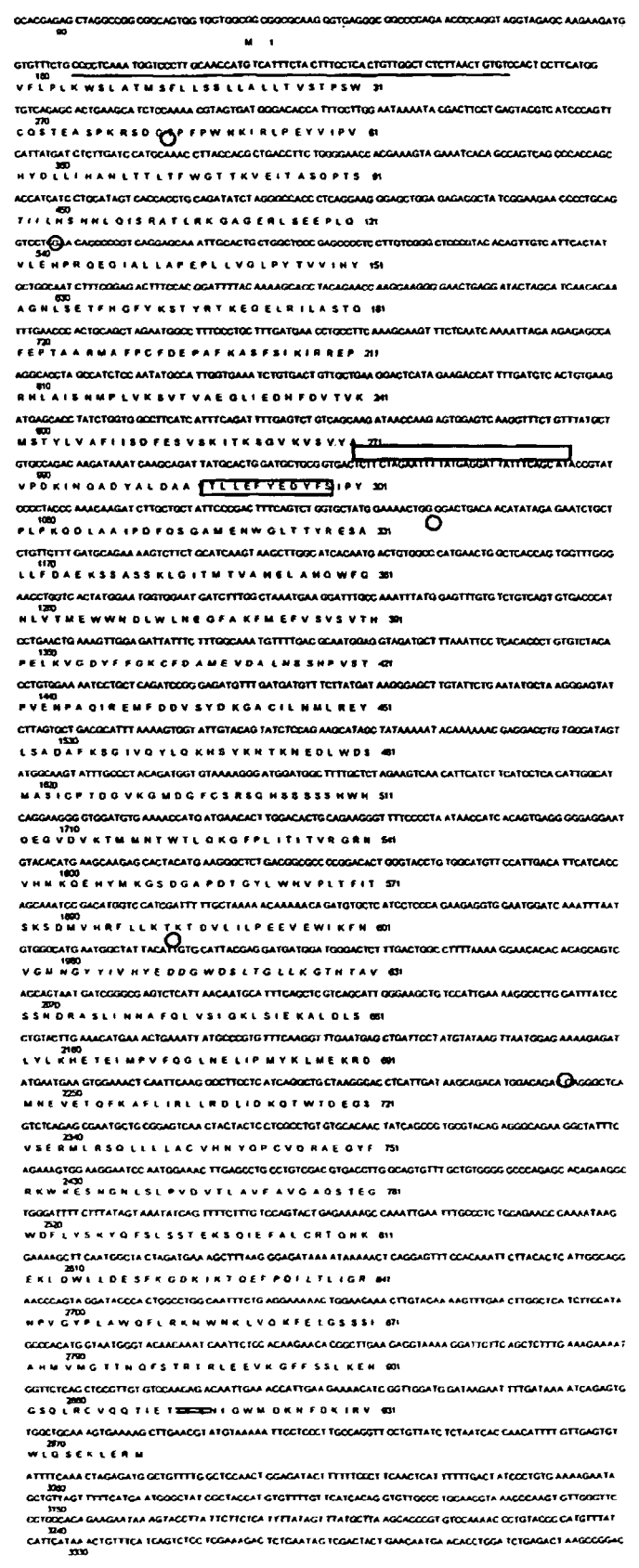

The present invention provides compositions and methods related to regulation of cytokine signaling through the Tumor Necrosis Factor (TNF) pathway. Specifically, the present invention provides a novel polypeptide, and a gene which encodes the polypeptide, as set forth in FIG. 1 and SEQ ID NOS:1 and 2, which has the ability to promote the shedding of the extracellular domain of Type I Tumor Necrosis Factor Receptor (TNFR1). This polypeptide and gene are called ARTS-1, for aminopeptidase regulator of type I, 55 kDa tumor necrosis factor receptor ectodomain shedding. It is contemplated that methods which regulate the shedding of the sTNFR1 also regulate the activity of TNF. It is further contemplated that the ARTS-1 gene, as well as genes substantially homologous to the ARTS-1 gene (and the gene product) regulate ectodomain shedding of other cytokine receptors, including IL-1 and IL-6. It is also contemplated that the compositions and methods provided by the present invention will find use in therapeutics for the treatment of diseases and disorders resulting from aberrant TNF activity.

TNFR1 Shedding

The complete mechanisms underlying TNFR1 ectodomain shedding are unknown, but are thought to be mediated via proteolytic cleavage of the spacer region located between the transmembrane and TNF-ligand binding domain (Brakebusch et al., *J. Biol. Chem.*, 269(51): 32488–96 [1994]). Based upon amino acid sequencing of sTNFR1 isolated from urine, the major cleavage site has been identified as occurring between Asn-180 and Val-181, with a minor site located between Lys-182 and Gly-183 (Nophar et al., *EMBO J.*, 9:3269–3278 [1990]; Wallach et al., In *Tumor Necrosis Factor: Structure-Function Relationship and Clinical Application* (Osawa and Baonavida, eds.) Vol III, 47–57, S. Karger, Basel, Switzerland [1991]; and Brakebusch et al., *J. Biol. Chem.*, 269(51):32488–96 [1994]). However, an understanding of the mechanism(s) is not necessary in order to use the present invention.

Again, although an understanding of the mechanism(s) is not necessary in order to use the present invention, a complete understanding of the mechanism regulating TNFR1 shedding requires the identification and characterization of the interactions between regulatory proteins, such as ARTS-1, TNFR1, and TNFR1 receptor sheddases, which appear to belong to the metalloprotease-disintegrin (ADAM) family of zinc metalloproteases (Blobel et al, *Cell* 90:589–592 [1997]). For example, TNF-α converting enzyme (TACE, ADAM17) has been reported to mediate the ectodomain shedding of TNF-α, tranforming growth factor-α, L-selectin and TNFR2 (Black et al., *Nature* 385:729–733 [1997]; Moss et al., *Nature* 385:733–736 [1997]; and Peschon et al., *Science* 282:1281–1284 [1998]). Similarly, TACE has been implicated in the regulated α-secretase cleavage of the amyloid precursor protein and ectodomain shedding of erbB4/HER4 (Buxbaum et al, *J. Biol. Chem.*, 273:27765–27767 [1998]; Rio et al., *J. Biol. Chem.*, 275: 10379–10387 [2000]). Recent data suggest that TACE may also mediate TNFR1 ectodomain shedding based upon the demonstration of increased TNFR1 shedding in reconstituted TACE-deficient cell lines (Reddy et al., J. Biol. Chem., 275:14608–14614 [2000]). Indeed, TACE has been implicated as having sheddase activity toward both TNFR1 and IL-1R type II (Reddy et al., supra).

Studies have also been undertaken to identify enzymes capable of cleaving (i.e., shedding) the leucocyte selectin (L-selectin) receptor, a peripheral lymph node homing receptor. The enzymes which shed the L-selectin receptor have been theorized to be metalloproteases (Preece et al., *J. Biol. Chem.*, 271:11634–11640 [1996]; Peschon et al., *Science* 282:1281–1284 [1998]; and Borland et al., *J. Biol. Chem.*, 274:2810–2815 [1999]).

Neither the sheddase nor the mechanism regulating the shedding of sTNFR1 are known, although attempts have been made to identify sTNFR1 shedding activities in crude preparations. However, the results indicate metal requirements for these activities, thereby tentatively categorizing the enzymes as metalloproteases (Bjonberg et al., *Scand. J. Immunol.*, 42:418–424 [1995]; Mullberg et al., *J. Immunol.*, 155:5198–5205 [1995]; Katsura et al., *Biochem. Biophys. Res. Comm.*, 222:298–302 [1996]; Williams et al., *J. Clin. Invest.*, 97(12):2833–2841 [1996]; and Gallea-Robache et al., *Cytokine* 9:340–346 [1997]). However, the molecular identities of these metalloprotease enzymes remain unknown.

Björnberg et al. (Björnberg et al., *Scand. J. Immunol.*, 42:418–424 [1995]) indicate that in assays to identify and characterize enzymes involved in TNFR1 processing, inhibitors of aminopeptidases had negligible effects on release of sTNFR1. These authors indicate that aminopeptidases are not involved in release of sTNFR1.

The mechanisms which regulate TNF activity, TNFR activation, TNFR1 signaling, sTNFR1 activity and sTNFR1 shedding are poorly understood. However, an understanding of these mechanisms is not necessary to practice the present invention. Indeed, the present invention is not limited to any particular mechanism or mechanisms.

IL-1RII and IL-6R Shedding

As discussed above, the cognate receptors for the cytokines IL-1 and IL-6 also exhibit soluble forms akin to the soluble form of TNFR1. Furthermore, it has been suggested that these soluble receptor forms play a role in the regulation of IL-1 and IL-6 activity and pro-inflammatory response. However, the proteins responsible for the shedding of ectodomains of the receptors for IL-1 and IL-6 remain unidentified. Nonetheless, it is contemplated that a protein which regulates the shedding of TNFR1 ectodomain (e.g., a protein of the present invention) will also regulate the shedding of ectodomains of other cytokine receptors, including IL-1RII and IL-6R. ARTS-1 binds to the soluble form of the IL-6 receptor and promotes the shedding of the IL-6 receptor. ARTS-1 also binds to the soluble form of the type II IL-1 receptors and promotes the shedding of the type II IL-1 receptors.

Anti-TNF Therapeutic Strategies

The recognition of TNF as an important inflammatory mediator in both health and disease has fostered the development of a variety of therapeutic strategies directed at inhibiting TNF bioactivity.

The benefits of inhibiting TNF activity during inflammatory reactions have been demonstrated using neutralizing monoclonal antibodies to TNF (Tracey et al., *Nature* 330: 662–664 [1987]; Hinshaw et al., *Circ. Shock* 30:279–292 [1990]; Opal et al., *J. Infect. Dis.*, 161:1148–1152 [1990]; Silva et al., *J. Infect. Sis.*, 162:421–427 [1990]; Emerson et al., *Circ. Shock* 38:75–84 [1992]; Fieldler et al., *J. Lab. Clin. Med.*, 120:574–588 [1992]; Jesmok et al., *Am. J. Pathol.*, 141:1197–1207 [1992]; Walsh et al., *Arch. Surg.*, 127: 138–144 [1992]; and Williams et al., *Proc. Natl. Acad. Sci. USA* 89:9784–9788 [1992]). Unfortunately, the development of widespread clinical application of neutralizing monoclonal antibodies directed against human TNF is hampered by the potential for immune rejection of the mouse anti-TNF antibodies in human hosts. The development of an immune response to non-human anti-TNF antibodies administered to human subjects may decrease the duration of therapeutic efficacy and also result in adverse events related to the formation of immune complexes or the development of hypersensitivity (Kempeni, *Ann. Rheum. Dis.*, 58(S1): I73–I81 [1999]).

A chimeric monoclonal antibody consisting of the variable region of a murine anti-TNF monoclonal antibody fused to the constant region of IgG1k has also been studied in clinical trials for the treatment of Crohn's disease (i.e., inflammatory bowel disease) (Knight et al., *Mol. Immunol.*, 30(16):1443–53 [1993]; Targan et al., *N. Engl. J. Med.*, 337:1029–1035 [1997]; and U.S. Pat. No. 5,656,272 to Le et al., hereby incorporated by reference). However, this anti-TNF antibody is not optimal, due to the likely development of human anti-chimeric antibodies directed against the non-human elements or the artificially fused sequences within the chimeric anti-TNF antibody. These deleterious antibodies are likely to reduce the half-life and therapeutic efficacy of the chimeric antibody, and possibly result in the formation of unwanted immune complexes or the development of hypersensitivity (Targan et al., *N. Engl. J. Med.*, 337: 1029–1035 [1997]; Harriman et al., *Ann. Rheum. Dis.*, 58:I61–164 [1999]; and Kempeni, *J. Ann. Rheum. Dis.*, 58:I73–I81 [1999]).

Anti-TNF therapies utilizing TNF receptor fragments and chimeric, soluble fusion proteins consisting of TNF receptor and IgG Fc, have been reported to be efficacious for patients with rheumatoid arthritis and inflammatory bowel disease (Moreland et al., *New Engl. J. Med.*, 337:141–147 [1997]; and U.S. Pat. No. 5,605,690 to Jacobs et al. (hereby incorporated by reference)). However, the therapeutic efficacy of these anti-TNF therapeutic strategies utilizing soluble forms of the TNF receptor or chimeric antibodies are also likely to be limited by the development of an immune response to the artificially fused human sequences (Kempeni, *Ann. Rheum. Dis.*, 58(S1):I73–I81 [1999]).

Current methods of controlling TNF activity in patients also include the use of non-specific inhibitors of cytokine gene transcription such as corticosteroids (e.g., dexamethasone and cyclosporin-A). These methods have significant and well known toxic side effects which result in significant discomfort and potentially life-threatening susceptibility to infection, as well as tissue and organ damage. Toxicities associated with cyclosporin-A include nephrotoxicity, hypertension, hepatic toxicity, neurotoxicity, hirsutism, gingival hyperplasia and gastrointestinal toxicity (Goodman & Gilman's *The Pharmacological Basis of Therapeutics*, 9$^{th}$ edition, McGraw-Hill, NY, [1996], p. 1299). Toxicity associated with corticosteroids include adrenal suppression, hyperglycemia, hypertension, edema, hypokalemic alkalosis, myopathy, peptic ulcer disease, osteoporosis, aseptic (ischemic or avascular) bone necrosis, mental status changes, glaucoma, cataracts and hyperlipidemia (Goodman & Gilman's *The Pharmacological Basis of Therapeutics*, 9$^{th}$ edition, McGraw-Hill, NY, 1996, p. 1475).

Induction of sTNFR1 shedding from cell culture systems can be induced by a variety of physiological and non-physiological mediators, such as, IFN-γ, IL-1β, IL-6, formyl-Met-Leu-Phe (fMLP), lipopolysaccharide, 4b-phorbol 12-myristate 13-acetate (PMA), calcium ionophore, staurosporine, and sodium salicylate (Porteu et al., *J. Biol. Chem.*, 266:18846–18853 [1991]; Nicod et al., *Ann. NY Acad. Sci.*, 28:323–333 [1994]; Tilg et al., *Blood* 83:113–118 [1994]; Zhang et al., *J. Biol. Chem.*, 269:10270–10279 [1994]; Mullberg et al., *J. Immunol.*, 155:5198–5205 [1995]; Levine et al., *Am. J. Respir. Cell Mol. Biol.*, 14:254–261 [1996]; and Madge et al., *J. Biol. Chem.*, 274:13643–13649 [1999]). However, these agents are poor candidates for development as drugs to regulate TNF activity in humans for a variety of reasons, most notably for the fact that most of these agents are toxic and not suitable for human therapeutic use. In addition, most of these agents are known to have or are likely to have detrimental or unwanted side effects resulting from their disruption of normal body processes in addition to their effects on TNF signaling.

Other strategies for the regulation of TNF activity have also been attempted or proposed. For example, U.S. Pat. Nos. 5,519,000 and 5,641,751 to Heavner et al. (hereby incorporated by reference) describe short (4–25 amino acid) peptides which bind TNF and inhibit TNF activity. U.S. Pat. Nos. 5,665,859 and 5,766,917 to Wallach et al. (hereby incorporated by reference) describe methods to isolate a TNFR1 protease or other polypeptides which influence TNFR1 shedding. U.S. Pat. No. 5,945,397 to Smith et al. (hereby incorporated by reference) describes human and mouse soluble TNF receptors and mutant variations of these receptors. U.S. Pat. No. 5,919,452 to Le et al. (hereby incorporated by reference) describes the use of anti-TNF antibodies, anti-TNF peptides, and soluble TNFR to treat TNF mediated pathologies.

However, until the development of the present invention, a nucleic acid in the form of a cDNA and a polypeptide encoded by the cDNA which has the ability to regulate the shedding of the TNFR1 ectodomain from the extracellular surface of a cell plasma membrane to yield a free, soluble form of the receptor, sTNFR1 had not been described. Indeed, database searches revealed that this gene and polypeptide had not heretofore been identified. These searches also revealed amino acid sequence motifs indicative of peptidase activity. Specifically, this gene has been named aminopeptidase regulator of type I, 55 kDa tumor necrosis factor receptor shedding, or "ARTS-1." Methods for the use of the ARTS-1 gene, polypeptide and other related compositions are provided by the present invention. In addition, methods for the identification of genes and polypeptides substantially homologous to ARTS-1 gene and polypeptide are also provided by the present invention. However, an understanding of the mechanisms of ARTS-1 activity is not necessary to practice the present invention.

It is contemplated that the protein (or proteins), and their corresponding genes, which regulate the cleavage of TNFR1 from the cell surface are likely to have important roles in regulating TNF activity in vivo in health and disease states. It is contemplated that cleavage of the TNFR1 ectodomain from the cell surface limits TNF activity by providing a pool of free receptors capable of binding and sequestering TNF, as well as by removing functional TNFR1 from the cell surface. It is further contemplated that occupation of the TNF bindings site on the free sTNFR1 ectodomain does not activate the intracellular components involved in TNF signaling. It is further contemplated that the genes and proteins which regulate the shedding of soluble TNFR1 ectodomain will find significant use in diagnostics and therapeutic regimens, as well as in the research setting. Furthermore, it is contemplated that genes and proteins which regulate the shedding of TNFR1 also regulate the shedding of other cytokine receptors important in inflammatory diseases and disorders (e.g., IL-1 and IL-6 receptors).

The present invention provides compositions and methods to identify genes and proteins which regulate the cleavage and shedding of the TNFR1 ectodomain. In addition, the present invention provides compositions suitable for the production of monoclonal and/or polyclonal antibodies directed against the proteins involved in the shedding of cytokine receptors (e.g., TNFR1). The present invention also provides compositions and methods suitable for the development of diagnostic tools and assay systems for the assessment of the factors involved in regulation of soluble TNFR1 as an indicator of health and/or disease.

The present invention also provides compositions and methods suitable for the development of more effective therapies for treating diseases and disorders resulting from aberrant TNF activity (e.g., for downregulation or upregulation of TNF activity), and consequently provide therapeutic advantages for treatment of diseases or disorders resulting from inflammatory response or immune-deficiency.

In addition, the present invention provides compositions and methods to develop additional means for suppressing damaging TNF-mediated proinflammatory diseases or disorders without the toxic side effects associated with existing techniques for immune suppression. The compositions and methods provided by the present invention address the need to identify genes and proteins which regulate TNF activity, and consequently, have therapeutic value in the treatment of immune disorders.

The remainder of the Description of the Invention is divided into the following sections:

I) Cloning of Genes Encoding TNFR1Ectodomain Binding Polypeptides

II) Preparation of Recombinant Vectors and Transformants

III) Analysis of ARTS-1 mRNA Expression

IV) Antibodies Directed Against ARTS-1 Polypeptide

V) Detection of ARTS-1 Polypeptide in Cultured and Primary Cells

VI) GST-ARTS-1 Polypeptide Expression and Purification

VII) Analysis of ARTS-1 Polypeptide Aminopeptidase Activity

VIII) Analysis of ARTS-1 TNFR1 Ectodomain Sheddase Regulatory Activity

IX) Analysis of TNFR1 Ectodomain Sheddase Regulatory Activity of ARTS-1 Catalytic Mutants X) Demonstration of ARTS-1/TNFR1 Protein Interaction XI) Therapeutic Agents for Immune Diseases and Disorders XII) Diagnostic Agents for Immune Disease and Disorders XIII) Identification of Genes Substantially Homologous to ARTS-1

XIV) Methods of Drug Screening

I. Cloning of Genes Encoding TNFR1 Ectodomain Binding Polypeptides

A) Yeast Two-Hybrid Screening

It was contemplated that polypeptides which form a physical interaction with the ectodomain of TNFR1 would be potential candidates for polypeptides which regulate the cleavage and shedding of the TNFR1 ectodomain. A yeast two-hybrid screen was performed in order to identify such TNFR1 interacting polypeptides using a TNFR1 bait and human lung cDNA two-hybrid prey library. Yeast two-hybrid screening is a common technique in the molecular biology arts (Ausubel et al. (eds.), *Current Protocols in Molecular Biology*, p. 20.0.1–20.1.40, John Wiley & Sons, Inc., New York [1994]). In the development of the present invention, the protocols, yeast strains and reagents used in these experiments were those supplied or recommended by the manufacturer (Matchmaker System 2; Yeastmaker Transformation System; Clontech), except where explicitly stated otherwise. The methods and compositions provided and used during the development of the present invention are provided in more detail below and in the Examples.

Conventional methods known to one of skill in the art may be used to prepare mRNA to construct a yeast-two hybrid library. In general, the source of the mRNA (e.g., tissue or cultured cells) are treated with a guanidine reagent, phenol reagent or the like to obtain the total RNA. Subsequently, poly(A+)RNA (i.e., mRNA) is obtained therefrom by an affinity column method using oligo dT-cellulose or poly U-Sepharose carried on Sepharose 2B. Further, the resultant poly(A+) RNA can be further fractionated by sucrose gradient centrifugation or the like.

Single-stranded cDNA is synthesized using the thus obtained mRNA as a template, an oligo(dT) primer and a reverse transcriptase. Then, a double-stranded cDNA is synthesized from the resultant single-stranded cDNA. The resultant double-stranded cDNA is integrated (i.e., ligated) into an appropriate cloning vector. In the case of this yeast two-hybrid library, the resulting double-stranded cDNAs are cloned into the pGAD10 plasmid (Clontech), a recombinant vector which contains operably linked parts which enable the transcription and translation of a chimeric gene consisting of the transcriptional activation domain of the yeast GAL4 transcription factor and the subcloned cDNA. The pGAD10 vector contains additional operably linked parts which enable its selection, replication and propagation in yeast strains as well as *E. coli*.

As indicated above, the yeast two-hybrid screen was conducted using the manufacturer's recommended protocols. A bait vector was constructed using the pAS2-1 plasmid (Clontech), to produce a chimeric fusion gene containing nucleic acid sequences encoding the DNA binding domain of GAL4 and the extracellular domain of the human TNFR1 receptor, corresponding to amino acids 26–216. Following sequential transformation of the chimeric pAS2-1 bait and pGAD10 prey vector library into yeast strain Y190, the library was screened for clones positive for growth on histidine (HIS) deficient media, followed by identification of those HIS+ clones which were also positive in a β-galactosidase filter lift assay. Thirty three clones positive for the ability to grow on HIS deficient substrate and β-galactosidase activity were identified, and each of those clones was sequenced. It is noted that numerous protocols and reagents for DNA sequencing are commercially available. It is contemplated that any suitable method known in the art may readily be used in place of the protocol described here as well as other aspects of the production of the compositions of the present invention.

One positive clone, L26C-53A, was selected for further study. This clone contained a 2355 bp insert containing a 631 amino acid open reading frame with a consensus zinc metalloprotease catalytic motif. The nucleotide sequence of this clone corresponds to bases 1044 to 3082 of the nucleic acid of FIG. 1 (SEQ ID NO:1). This gene was named aminopeptidase regulator of type I, 55 kDa tumor necrosis factor receptor ectodomain shedding, or "ARTS-1."

The yeast two-hybrid screening described herein is not meant to limit the present invention to the particular reagents and methods described. Indeed, numerous other vectors and reagents may be used to produce the ARTS-1 gene provided by the present invention. For example, a different two-hybrid prey library may be substituted for the human lung cDNA library to yield the ARTS-1 gene. Similarly, pAS2-1 and pGAD10 vector variants may be used, for example those which have different multiple cloning sites to facilitate subcloning of the cDNA insert. Vector variants which use the LexA operator components in place of the GAL4 system may also be used in place of those described here. Also, variants of these vectors with or without an operably joined HA antigenic tag may be used in order to facilitate immunodetection of the fusion protein. Similarly, *Saccharomyces cerevisiae* strains other than Y190 may be used as the doubly transformed host strain for the library screening (e.g., *S. cerevisiae* strain CG-1945). In addition, selection conditions may be varied, for example, by changing the concentration of 3-AT (3-amino-1,2,4-triazole) to counterselect leaky HIS+ clones. Many of these alternative variables and reagents are described and are commercially available (e.g., from companies such as Stratagene and Clontech). Thus, it is intended that the compositions of the present invention may be produced using any suitable method known in the art.

B) Phage Plaque Hybridization/cDNA Cloning

The DNA sequence identified in the yeast interaction screen appeared not to be a full length cDNA. This, the complete ARTS-1 cDNA was isolated by screening a phage library using a $^{32}$P-labelled DNA probe derived from clone L26C-53A. The library used in this cDNA screening was constructed using poly (A+) mRNA from the human NCI-H292 pulmonary mucoepidermoid carcinoma cell line (ATCC, CRL 1848) which had been stimulated with 1 μM PMA (phorbol 12-myristate, 13-acetate, Sigma). This cell line has been demonstrated to shed sTNFR1 in response to PMA stimulation (Levine et al., *Am. J. Respir. Cell. Mol.*

Biol., 14:254–261 [1996]). The library was constructed using the uni-ZAP XR phage vector (Stratagene).

Bacteriophage from the library were plated in a lawn of XL1-Blue E. coli (Stratagene) at a density of 50,000 pfu per 150 mm plate and incubated overnight at 37° C. Plaques were transferred to Hybond N+ filters (Amersham/Pharmacia) and denatured. Filters were then neutralized and UV cross-linked. Filters were washed in pre-hybridization solution, then hybridized overnight at 42° C. with a $^{32}$P-labelled L26C-53A insert generated by random primed labelling. Filters were washed, and were then exposed to x-ray film overnight and positive plaques were selected. Positive plaques were subjected to two additional rounds of plaque hybridization prior to sequencing. Positive plaques were recovered via in vivo excision utilizing the ExAssist helper phage (Stratagene).

It is not intended that the present invention be limited to any particular cDNA library, reagent or method for the production of the nucleic acid encoding the ARTS-1 polypeptide of the present invention. Thus, it is contemplated that any suitable library will find use in isolating the ARTS-1 cDNA. For example, such libraries may include libraries made from mRNA derived from human chronic myelogenous leukemia cell line K-562, lymphoblastic leukemia cell line MOLT-4 or lung carcinoma A549 cell line. Similarly, multiple techniques for the radiolabelling and purification of nucleic acid probes as well as phage plaque hybridization protocols are well known in the art (Ausubel et al. (eds.), Current Protocols in Molecular Biology, Vol. 1–4, John Wiley & Sons, Inc., New York [1994]). The probe synthesis and hybridization methods and conditions described here are not meant to limit the scope of the present invention. Variations on these protocols include alternative labelling methods (e.g., 5' end labelling, overhang fill-in labelling and random primed synthesis labelling). Alternative detection systems can also be used, including $^{33}$P probe labelling and non-radioactive probe visualization methods such as chemiluminescence.

Following three rounds of screening, four hybridizing phage clones were identified from the library, amplified, then sequenced. These four clones all overlapped the L26C-53A sequence, as expected. However, none encoded a full-length cDNA, nor did they collectively span the entire gene. One phage clone (bp 1–1777) contained the putative 5' UTR and three phage clones contained the putative 3' UTR and the poly(A) tail (bp 2181–4845). cDNA sequence encoding the portion of the gene lying between the 5' and 3' terminal clones was amplified via PCR from the same human lung cDNA library using primers corresponding to 5' and 3' sequence obtained from the phage screening. The cDNA segment amplified with these primers was subcloned and both strands were sequenced to verify PCR fidelity.

As discussed in Section A above, it is not intended that the present invention be limited to any particular reagents, methods, and/or compositions for the production of the nucleic acids and polypeptides of the present invention. Thus, it is contemplated that any suitable methods for cDNA cloning and/or phage plaque hybridization will find use in the production of the compositions of the present invention. For example, one of numerous commercially available DNA polymerases may be used in the PCR reaction, including Taq (Stratagene, Promega), Pfu (Promega) or Sequenase (Amersham). Furthermore, it is contemplated that alternative PCR reaction conditions (i.e., temperatures and time intervals) will also be successful in amplifying the ARTS-1 nucleic acid of the present invention. Similarly, numerous vectors and reagents are equally suitable for subcloning and sequencing reactions.

C) Analysis of the ARTS-1 cDNA and Predicted Polypeptide

Inspection of the full length cDNA obtained as described above revealed a 4845 nucleotide transcript, containing a 2823 bp open reading frame and 5' and 3' untranslated regions as shown in FIG. 1. In this Figure, a consensus polyadenylation site located at nucleotides 4795 to 4800 is indicated with a double underline and lies 18 nucleotides upstream of a 27 nucleotide poly(A) tail. Two mRNA destabilization motifs are also identified at nucleotides 3929 and 4457 using bold and underline.

The open reading frame (ORF) encodes a 941 amino acid polypeptide. The first ATG codon lying in-frame relative to the largest open reading frame is located at nucleotide 88, and a TAA stop codon in the same reading frame is located at nucleotide 2911. Asparagine residues comprising five potential N-glycosylation sites are indicated with circles. A putative transmembrane domain, extending from amino acids 5 to 28, is also indicated in the Figure with a single underline. In order to determine this sequence, sequence analysis, including Kyte-Doolittle hydropathy prediction (Kyte and Doolittle, J. Mol. Biol., 157:105–132 [1982]) was performed using MacVector 7.0 software (Oxford Molecular). The location of the putative hydrophobic transmembrane α-helical domain was predicted utilizing several web-based analysis programs (MEMSAT2 (McGuffin et al., Bioinform., 16:404–405 [2000]; Sosui (Hirokawa et al., Bioinform., 14:378–379 [1998]; TMAP (Persson and Argos, J. Mol. Biol., 237:182–192 [1994]); TMpred (Hofmann and Stoffel, Biol. Chem. Hoppe-Seyler 374:166 [1993]; and TopPred2 (von Heijne, J. Mol. Biol., 225:487–494 [1992]). In sum, ARTS-1 is predicted to be a type II integral membrane protein with a single hydrophobic transmembrane α-helical domain, located between amino acids 5 and 28 (See, FIGS. 1 and 2), and a very short hydrophobic intracellular amino-terminal domain (See, McGuffin et al., Bioinform., 16:404–405 [2000]; Hirokawa et al., Bioinform., 14:378–379 [1998]; Persson and Argos, J. Mol. Biol., 237:182–192 [1994]); Hofinann and Stoffel, Biol. Chem. Hoppe-Seyler 374:166 [1993]; and von Heijne, J. Mol. Biol., 225:487–494 [1992]).

Subdomains of homology indicate that ARTS-1 is a member of the aminopeptidase family of gluzincin zinc metalloproteases. This family of proteins share motifs indicating similar biochemical activity, although the family members are extremely diverse in overall structure in biological function (Zinc Metalloproteases in Health and Disease, Taylor & Francis, London, England [1996], Hooper, p. 1–21, and Wang and Cooper, p. 131–151). FIG. 1 also indicates the ARTS-1 sequences which adhere to the consensus zinc metalloprotease catalytic motif for the aminopeptidase family, HEXXH(Y)$_{18}$E (SEQ ID NO:10). Within this motif, it is theorized that the two histidine residues (H) and the second glutamic acid residue (E) represent the zinc binding domain while the first glutamic acid mediates the catalytic activity. In the ARTS-1 polypeptide, this consensus motif is observed at T$^{350}$VAHELAHQWFG (SEQ ID NO:8) and L$^{372}$WLNEGFA (SEQ ID NO:9) (boxed in FIG. 1).

Furthermore, a schematic representation of the ARTS-1 protein, indicating domains of homology with the aminopeptidase family of gluzincin zinc metalloproteases is provided in FIG. 2. A zinc metalloprotease consensus catalytic motif HEXXH(Y)$_{18}$E (SEQ ID NO:10), a short intracytoplasmic tail, a transmembrane domain and a large 375 amino acid domain of homology are also depicted in this Figure.

Quantitative comparisons between ARTS-1 protein and other members of the aminopeptidase-gluzincin zinc metalloprotease family are shown in Tables 1 and 2 below. Table 1 provides quantitation of percent identity and percent similarity between the full length amino acid sequence of the ARTS-1 protein and other aminopeptidase family members. Percent identities are shown above the shaded diagonal and percent similarities are shown below the shaded diagonal. Table 2 shows a similar comparison between the conserved 375 amino acid domain in the ARTS-1 protein containing the consensus zinc binding motif HEXXH(Y)$_{18}$E (SEQ ID NO:10) and other members of the aminopeptidase family of gluzincin zinc metalloproteases. The aminopeptidase family members included in these Tables are human placental leucine aminopeptidase (PLAP) (Rogi et al., *J. Biol. Chem.*, 271:56–61 [1996]), rat insulin-regulated aminopeptidase (IRAP) (Keller et al., *J. Biol. Chem.*, 270:23612–23618 [1995]), human aminopeptidase A (AMP A) (Nanus et al., *Proc. Natl. Acad. Sci. USA* 90:7069–7073 [1993]; and Li et al., *Genomics* 17:657–664 [1993]), human aminopeptidase N (AMP N) (Olsen et al., *FEBS Lett.*, 238:307–314 [1988]), human puromycin sensitive aminopeptidase (Tobler et al., *J. Neurochem.*, 68:889–897 [1997]), rat thyrotropin-releasing hormone degrading enzyme (TRH DE) (Schauder et al., *Proc. Natl. Acad. Sci. USA* 91:9534–9538 [1994]), S. cerevisiae aminopeptidase YSCII (Garcia-Alvarez et al, *Eur. J. Biochem.*, 202:993–1002 [1991]), C. elegans cosmid F49E8.3 gene product (Wilson et al., *Nature* 368:32–38 [1994]), and *Lactococcus lactis* aminopeptidase N (Tan et al., *FEBS Lett.*, 306:9–16 [1992]).

As mentioned above, and as indicated in these Tables, although members of this aminopeptidase family share a similar biochemical motif, there is significant sequence divergence among family members, likely indicating distinct and specialized biological functions.

TABLE 1

Percentage Identity and Similarity Between Full Length ARTS-1 Protein and Other Members of the Aminopeptidase-Gluzincin Zinc Metalloprotease Family

| Protein | Human ARTS-1 | Human PLAP | Rat IRAP | Human AMP A | Human AMP N | Rat TRH DE | Human PSA | C. elegans F49E8.3 | L. Lactis AMP N | S. cerevisiae YSC II |
|---|---|---|---|---|---|---|---|---|---|---|
| Human ARTS-1 |  | 44 | 41 | 31 | 29 | 27 | 30 | 26 | 24 | 27 |
| Human PLAP | 17 |  | 79 | 30 | 29 | 27 | 28 | 25 | 23 | 26 |
| Rat IRAP | 15 | 5 |  | 28 | 28 | 28 | 26 | 24 | 21 | 24 |
| Human AMP A | 20 | 19 | 18 |  | 34 | 29 | 30 | 25 | 22 | 28 |
| Human AMP N | 18 | 18 | 18 | 18 |  | 22 | 29 | 27 | 24 | 26 |
| Rat TRH DE | 17 | 16 | 17 | 17 | 14 |  | 26 | 23 | 22 | 22 |
| Human PSA | 17 | 19 | 17 | 16 | 17 | 16 |  | 36 | 28 | 32 |
| C. elegans F49E8.3 | 18 | 17 | 15 | 18 | 17 | 17 | 16 |  | 28 | 31 |
| L. lactis AMP N | 16 | 16 | 15 | 17 | 15 | 14 | 16 | 18 |  | 27 |
| S. cerevisiae YSC II | 16 | 18 | 16 | 15 | 16 | 16 | 16 | 19 | 18 |  |

TABLE 2

Percentage Identity and Similarity Between the Conserved Domains Containing the Zinc Binding Motif of ARTS-1 Protein and Other Members of the Aminopeptidase-Gluzincin Zinc Metalloprotease Family

| Protein | Amino Acid Position | Human ARTS-1 | Human PLAP | Rat IRAP | Human AMP A | Human AMP N | Rat TRH DE | Human PSA | C. elegans F49E8.3 | L. lactis AMP N | S. cerevisiae YSC II |
|---|---|---|---|---|---|---|---|---|---|---|---|
| Human ARTS-1 | 161–535 |  | 51 | 53 | 39 | 43 | 41 | 44 | 42 | 36 | 41 |
| Human PLAP | 192–540 | 15 |  | 90 | 42 | 43 | 39 | 44 | 44 | 36 | 44 |
| Rat IRAP | 273–621 | 12 | 6 |  | 41 | 42 | 39 | 44 | 45 | 37 | 43 |
| Human AMF A | 202–549 | 21 | 18 | 18 |  | 44 | 41 | 48 | 44 | 36 | 45 |
| Human AMP N | 192–554 | 15 | 15 | 16 | 19 |  | 42 | 47 | 44 | 37 | 45 |
| Rat TRH DE | 248–603 | 14 | 17 | 17 | 17 | 16 |  | 41 | 40 | 37 | 38 |
| Human PSA | 158–508 | 16 | 18 | 17 | 14 | 14 | 18 |  | 52 | 41 | 52 |
| C. elgens F49E8.3 | 120–469 | 16 | 17 | 16 | 17 | 17 | 20 | 16 |  | 41 | 49 |

TABLE 2-continued

Percentage Identity and Similarity Between the Conserved Domains Containing the
Zinc Binding Motif of ARTS-1 Protein and Other Members of the
Aminopeptidase-Gluzincin Zinc Metalloprotease Family

| Protein | Amino Acid Position | Human ARTS-1 | Human PLAP | Rat IRAP | Human AMP A | Human AMP N | Rat TRH DE | Human PSA | C. elegans F49E8.3 | L. lactis AMP N | S. cerevisiae YSC II |
|---|---|---|---|---|---|---|---|---|---|---|---|
| L. Lactis AMP N | 99–445 | 16 | 20 | 18 | 18 | 17 | 15 | 18 | 17 | | 40 |
| S. cerevisiae YSC II | 114–461 | 15 | 16 | 15 | 16 | 16 | 19 | 15 | 18 | 20 | |

II. Preparation of Recombinant Vectors and Transformants

Preparation of Recombinant Vectors

Numerous recombinant vectors relevant to the present invention are contemplated. Such vectors, containing the gene or portions of the gene of the present invention (i.e., the ARTS-1 gene) may be of any type, with the only limitation being that the vector into which the gene of the invention has been inserted has the capacity for replication in a host. As used in the present invention, a host may be a bacteria (e.g., *E. coli* BL21 strain), a yeast (e.g., *S. cerevisiae* Y190 strain), or an animal cell (e.g., the NCI-H292 human pulmonary mucoepidermoid carcinoma cell line). Furthermore, the host cell may exist in an in vitro tissue culture system, or exist within an intact organism (e.g., a mouse or a human). Indeed, it is not intended that the host be limited to any particular cell type, nor is it intended that the cell host be maintained in any particular setting.

Protocols for the construction of recombinant vectors are commonplace in the molecular biology arts, and reagents for the manipulation of recombinant nucleic acids are readily available from commercial sources. Routine procedures in the construction of a recombinant vector encompassed by the present invention may include restriction endonuclease digestion, ligation, phosphorylation, dephosphorylation, blunt-ending, size separation, annealing, eluting, staining, desalting, transformation, inoculating, incubating, cesium banding and purification by a variety of commercially available products. In the most simple of embodiments, a recombinant vector of the invention may be made by digesting the gene of the invention with an appropriate restriction enzyme, ligating into an appropriately digested vector, transforming the ligated vector into bacteria, selection using an antibiotic resistance marker contained on the vector and purifying the vector using a kit designed for rapid, small scale plasmid purification.

A vector may be in the form of a DNA plasmid. Such plasmids contain multiple parts operably arranged to permit replication in a minimum of one specific host species. A plasmid (e.g., the pGEX-6P-1 plasmid) may be restricted to replication in bacteria, or may also contain operably linked sequences which permit the plasmid to propagate or function in a second species in addition to its usual bacterial host. For example, the pAS2-1 and pGAD10 vectors contain operably linked nucleic acid sequences which permit their propagation in both bacteria and yeast (e.g., the *S. cerevisiae* Y190 strain), while the pTarget vector contains operably linked sequences which permit its propagation in a bacterial host, but also contains sequences which allow it to direct the transcription of a cloned gene in a mammalian cell.

A vector may also be in the form of a DNA or RNA bacteriophage or other virus, which further may be in the form of a DNA or RNA containing virus. Such phage or other virus may be replication competent or replication defective. The phage or viral nucleic acid may also be engineered to permit propagation in an organism as a plasmid in addition to its viral life cycle. For example, the bacteriophage Lambda (λ) uni-ZAP II vector (Stratagene) is capable of bacterial infection as a bacteriophage, but also contains sequences which enable the excision and propagation of a plasmid form of the vector. Such a vector is often called a "phagemid." Further, recombinant viral vectors (e.g., retrovirus, adenovirus, adeno-associated virus or vaccinia virus) or an insect virus vector (e.g., baculovirus) may also be used to infect cells.

In particularly preferred embodiments, the gene of the present invention is operably linked to other components of the vector. For this purpose, the vector of the invention may contain, if desired, cis elements (e.g., an enhancer, splicing signal, poly(A) addition signal, selection marker, ribosome binding sequence (i.e., Shine-Dalgarno or Kozak sequences) or the like) in addition to a promoter/enhancer and the gene of the present invention. As the selection marker, genes encoding resistance to dihydrofolate reductase, ampicillin, kanamycin, neomycin, or the like may be used.

Preparation of Transformants

In some embodiments of the present invention, a transformant was obtained by introducing the recombinant vector containing the gene of the invention into a host. The host is not particularly limited as long as it can harbor the vector of the invention. Specific examples of host include Escherichia bacteria such as *E. coli*; yeast such as *S. cerevisiae* and *Schizosaccharomyces pombe*; animal cells such as COS cells, CHO cells, NCI-H292 cells or non-specified cells of an intact organism; or insect cells such as S*f*9 and S*f*21 cells. In some embodiments of the present invention, the vector is introduced into the host under conditions such that the polypeptide encoded by the gene of the invention is expressed.

In some cases, when a bacterium such as *E. coli* is used as the host, the recombinant vector of the invention is capable of replication in the host and, at the same time, is capable of expressing the gene of the invention within the bacterial host (e.g. the pGEX-ARTS-1 vectors). Such vectors in general preferably consist of a promoter, a ribosome binding sequence, the gene of the present invention and a transcription termination sequence. The vector may also contain a gene to control the promoter.

Any promoter may be used as long as it can appropriately direct the expression of the gene of interest in the host cells, such as a mammalian cell or *E. coli*. For example, an *E. coli* or phage-derived promoter such as trp promoter, lac promoter, $P_L$ promoter or $P_R$ promoter may be used. An artificially designed and altered promoter such as tac promoter may also be used.

Any method for bacterial transformation may be used for introducing a recombinant vector into a bacterium. Many methods are commonly known in the art, including electroporation and the use of bacteria made competent by calcium chloride (See e.g., Ausubel et al. (eds.), *Current Protocols in Molecular Biology*, p. 1.8.1–1.8.10, John Wiley & Sons, Inc., New York [1994]).

Likewise, any method for introducing DNA into yeast may be used to introduce a recombinant vector into a yeast. For example, electroporation (Becker et al., *Methods Enzymol.*, 194:182–187 [1991]), the spheroplast method (Hinnen et al., *Proc. Natl. Acad. Sci. USA* 75:1929–1933 [1978]), the lithium acetate method (Ito, *J. Bacteriol.*, 153:163–168 [1983]) or the like may be used.

It is contemplated that any suitable animal cells will find use as hosts in the present invention (e.g., simian COS-7 or Vero cells, Chinese hamster ovary cells (CHO cells), mouse L cells, rat GH3 cells, human FL cells, human lymphoid cell lines, or the like). A promoter/enhancer may be used to express the ARTS-1 gene where the promoter is active in all or most cell types (e.g., the SRα promoter, SV40 promoter, HSV-LTR promoter, CMV promoter or the like). Alternatively, promoter/enhancer elements may be used which direct expression of the ARTS-1 gene in only a subset of cells (e.g., cells of the lymphoid system).

As with other host cells, any suitable method for introducing the recombinant vector into animal or insect cells (e.g., electroporation, the calcium phosphate method, lipofection or the like) may be used.

III. Analysis of ARTS-1 mRNA Expression

Following the identification and isolation of the ARTS-1 gene, an experiment was undertaken to determine the pattern of tissue expression of the endogenous ARTS-1 mRNA. This was accomplished using a multi-tissue Northern blot and an ARTS-1 derived probe as shown in FIG. 3 and described in greater detail in Example 3.

The blot used in this experiment was a commercially available human multiple tissue poly(A+) Northern blot (Clontech). This blot was probed according to the manufacturer's suggested protocol using a full length $^{32}$P-labelled ARTS-1 cDNA probe.

Figure 3:
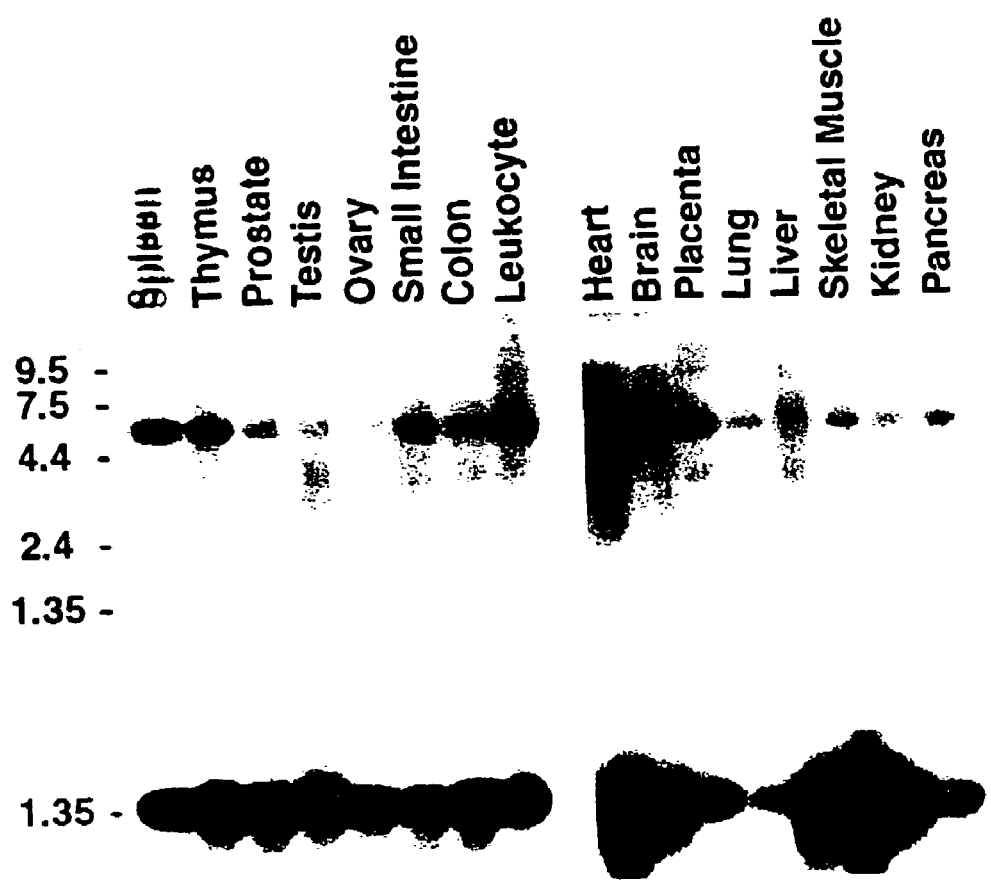
FIG. 3 provides a Northern blot analysis of multiple human tissues using a $^{32}$p-labelled ARTS-1 cDNA probe. The upper panel shows the blot probed with the ARTS-1 cDNA probe. The lower panel shows the same blot following stripping and rehybridization to a probe specific for the human glyceraldehyde-3-phosphate dehydrogenase (GAPDH) gene as a reference for RNA loading normalization.

The Northern blot analysis shown in FIG. 3, Panel A, indicates that the human ARTS-1 transcript was expressed in multiple tissues, including spleen, thymus, small and large intestine, peripheral blood leukocyte, heart, placenta, lung, skeletal muscle, kidney and pancreas. In these tissues, a single predominant mRNA species of approximately 5.7 kB was detected. FIG. 3, Panel B, shows the same blot following stripping and rehybridization to a probe specific for the human GAPDH transcript as a reference for RNA loading normalization.

Furthermore, in view of numerous alternative protocols known in the art for Northern blotting, it is not intended that the present invention be limited to the Northern blotting protocol provided in Example 3 or any other particular Northern blotting method. For example, in some embodiments, RNA is isolated from tissue samples using alternative methods (e.g., a commercial RNA isolation kit such as Qiagen RNeasy Total RNA Mini Kit, Catalog No. 74103).

Similarly, alternative probe synthesis and labelling techniques also find use with the present invention. For example, any probe having a minimum complementarity of 25 base pairs to the ARTS-1 cDNA will find use in the Northern blot methods of the present invention. Furthermore, it is contemplated that the nucleic acid comprising the probe will be generated by PCR, by restriction digest, or by synthetic oligonucleotide synthesis. Alternative nucleic acid probe labelling methods also find use with the present invention (e.g., labelling with $^{33}$P radioisotope or non-radioactive labelling methods). In addition, alternative Northern blotting protocols, reagents and equipment suitable for use in the present invention are known in the art (See, e.g., Ausubel et al. (eds.), *Current Protocols in Molecular Biology*, Vol. 1, pages 4.9.1–4.9.16, John Wiley & Sons, Inc., New York [1994]).

IV. Antibodies Directed against the ARTS-1 Polypeptide

In the present invention, polyclonal antiserum directed against the ARTS-1 polypeptide is provided. However, the antibody of the invention may be prepared by various methods, as numerous methods for the production of monoclonal and polyclonal antibodies are well known in the art (See e.g., Sambrook, J. et al. (eds.), Molecular Cloning, Cold Spring Harbor Laboratory Press [1989]; Harlow and Lane (eds.), *Antibodies: A Laboratory Manual*, Cold Spring Harbor Laboratory Press [1988]; Ausubel et al. (eds.), *Current Protocols in Molecular Biology*, p. 11.4.2–11.15.4, John Wiley & Sons, Inc., New York [1994]). As used herein, the term "antibody" means an antibody molecule as a whole or a fragment of an antibody (e.g., Fab or F(ab')$_2$ fragment) which can bind specifically to an antigen. The antibody provided by the invention is described in more detail below and in Example 4. The present invention also contemplates that these same methods will find use in the production of antibodies specific for polypeptides encoded by genes which are substantially homologous to the ARTS-1 gene.

In order to conduct additional studies on the ARTS-1 polypeptide, polyclonal antiserum was generated against an ARTS-1 polypeptide. A commercial service (Research Genetics) was used in these studies. Specifically, a 17 amino acid ARTS-1 synthetic peptide was used to immunize New Zealand white rabbits. This peptide corresponded to amino acids 538 to 554 of the ARTS-1 polypeptide and had the sequence:

R$^{538}$GRNVHMKQEHYMKGSD (SEQ ID NO:7)

This particular peptide was chosen based upon its antigenic potential and its lack of homology with other protein sequences as determined by a BLAST homology search.

Rabbits were immunized with this peptide using standard techniques. The ARTS-1 peptide was conjugated to KLH and mixed with an equal volume of Freund's complete adjuvant. The amount of antigen utilized per immunization was 0.1 mg, which was injected into three subcutaneous dorsal sites. The animals received boosts at weeks 2, 6 and 8. Bleeds were obtained at weeks 4, 8 and 10, and tested for the presence of anti-ARTS-1 antibody. In subsequent experiments, the antiserum obtained from the 10 week bleed was used.

In view of numerous alternative protocols known in the art for the production of polyclonal antibodies, the present invention is not meant to be limited to any particular method. For example, the entire 941 amino acid ARTS-1 polypeptide, or any portion or fragment thereof, may potentially be used as the immunogen, and the immunogen may be either synthetic or native. It is not intended that the present invention be limited to any particular ARTS-1 derived immunogen, method of immunization, immunization schedule, animal species, test protocol for determining antibody production or antibody purification method.

Although the antibody provided by the invention is polyclonal, the invention also contemplates monoclonal antibodies directed against the ARTS-1 polypeptide. It is also contemplated that any suitable method for the production of monoclonal antibodies will find equal use in the present invention. In one embodiment, the immunogen used to produce these monoclonal antibodies comprises full-length ARTS-1 polypeptide, although it is contemplated that any portion or fragment of the ARTS-1 polypeptide may also find use in the present invention as an imnmunogen.

In these monoclonal antibody protocols, any suitable method for recovery of antibody producing cells, cell fusion, selection and cloning of hybridomas, recovery of the monoclonal antibodies, and purification of the monoclonal antibodies of interest may be used. Thus, it is not intended that the present invention be limited to any particular monoclonal antibody production system or method.

If desired, the polyclonal or monoclonal antibody preparation of the invention can be purified from crude antiserum or culture supernatant using a conventional method (e.g., Protein A affinity, ammonium sulfate precipitation, ion exchange chromatography, gel filtration, affinity chromatography, or any of these methods in combination).

Once the polyclonal or monoclonal antibody is thus obtained, in some embodiments of the present invention, the antigen is bound to a solid support, so as to thereby prepare an affinity chromatography column. Using this column, the antibody of the present invention can be highly purified. Conversely, in an alternative embodiment of the present invention, the antibody is bound to a solid support as to thereby prepare an affinity chromatography column. Using this column, the ARTS-1 polypeptide, or fragments thereof, either native or recombinant, can be highly purified from variable sources. These monoclonal and polyclonal antibodies find numerous uses, including Western blotting, immunoprecipitation, immunohistochemistry and clinical applications using methods known in the art (See e.g., Harlow and Lane (eds.), *Antibodies: A Laboratory Manual*, Cold Spring Harbor Laboratory Press [1988]; Ausubel et al. (eds.), *Current Protocols in Molecular Biology*, Vol. 1–4, John Wiley & Sons, Inc., New York [1994]; and Laurino et al., *Ann. Clin. Lab Sci.*, 29(3):158–166 [19991]).

V. Detection of ARTS-1 Polypeptide in Cultured Cell Lines and Primary Cells

Following the production of ARTS-1 polyclonal antiserum, the expression of endogenous ARTS-1 polypeptide in cultured and primary cells was investigated using standard Western immunoblotting techniques well known in the art, as discussed below and described in further detail in Example 5. Protein concentrations of the samples were assayed and 20 micrograms of total protein were prepared for analysis in Laemmli buffer. Samples were resolved via 6% polyacrylamide SDS-PAGE and electroblotted onto nitrocellulose. Blots were incubated overnight in blocking buffer, then incubated for 2 hours with ARTS-1 antiserum at a 1:20,000 dilution in blocking buffer. Membranes were washed, then incubated with horseradish peroxidase conjugated goat anti-rabbit IgG (Life Technologies) diluted to 1:5,000 in blocking buffer, then washed again. Membranes were then incubated in chemiluminescent detection substrate and the signal detected on X-ray film.

Figure 4:
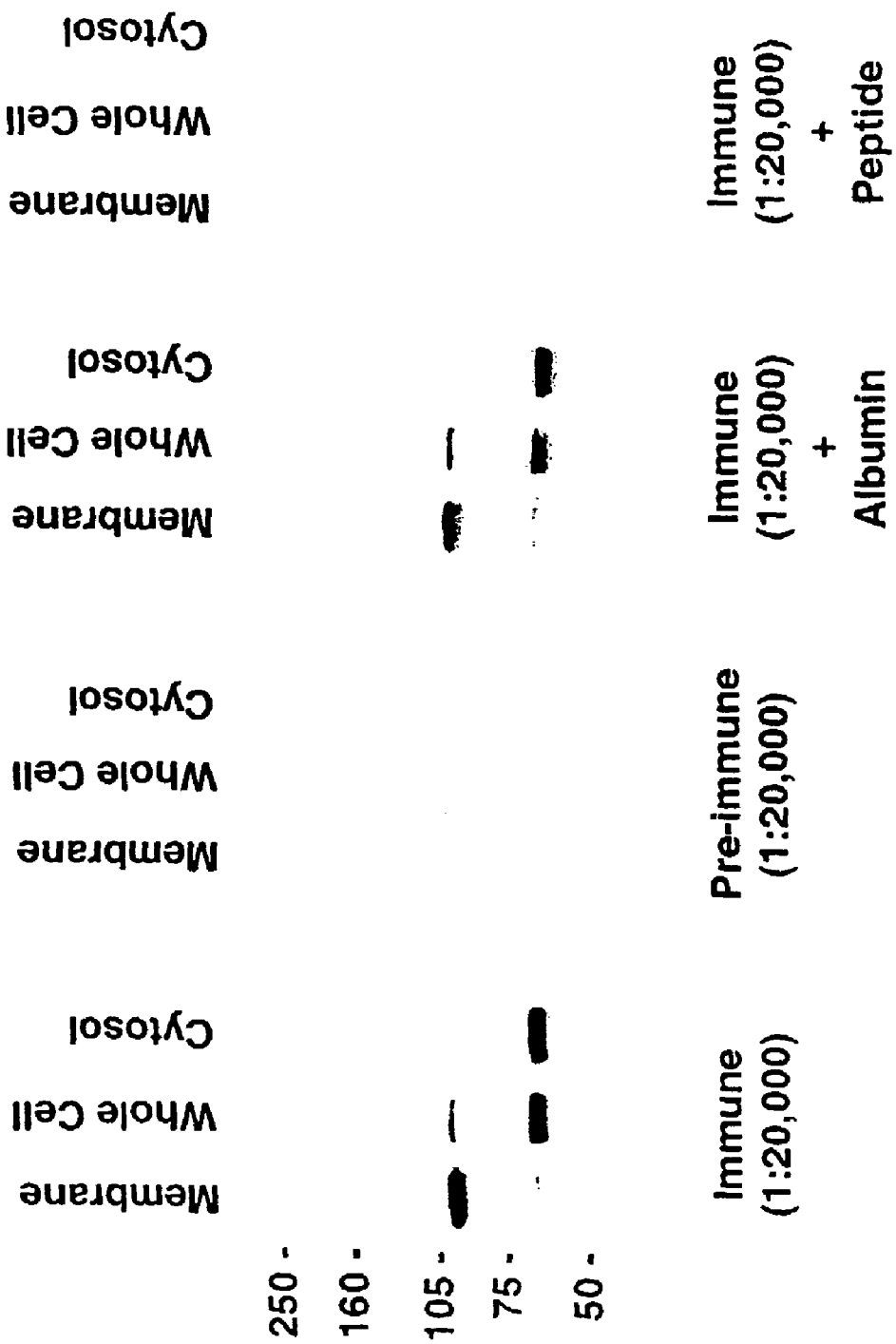
FIG. 4 provides Western immunoblots using pre-immune and polyclonal anti-ARTS-1 antisera in conjunction with crude whole cell homogenates, and membrane and cytosolic fractions made from cultured NCI-H292 cells. The top panel provides a Western immunoblot using the immune sera. The next panel provides a Western immunoblot using the pre-immune sera. The bottom two panel provide results from Western immunoblot competition experiments using bovine serum albumin or ARTS-1 cognate peptide, respectively.

The specificity of the resulting polyclonal antiserum was first determined as shown in FIG. 4. Extracts analyzed in this experiment were crude whole cell homogenates, and membrane and cytosolic fractions all prepared from cultured NCI-H292 cells. As shown in FIG. 4, Panel A, the anti-ARTS-1 antiserum detected a predominant 100 kDa membrane form and a predominant 68 kDa cytosolic form from the NCI-H292 cells, while the whole cell extracts predictably revealed a mixture of these two forms. As shown in the second panel FIG. 4, the preimmune serum showed no reactivity towards the same samples when used at the same concentration.

Specificity of the immune serum was further demonstrated in competition experiments in the third and fourth panels of FIG. 4. Preincubation of the immune serum with the RGRNVHMKQEHYMKGSD peptide (SEQ ID NO:7) against which the polyclonal antiserum was raised resulted in almost complete attenuation of the immune signal (Bottom panel). In contrast, preincubation of the immune serum with bovine serum albumin resulted in minimal attenuation of immune signal (Third panel).

Figure 5:
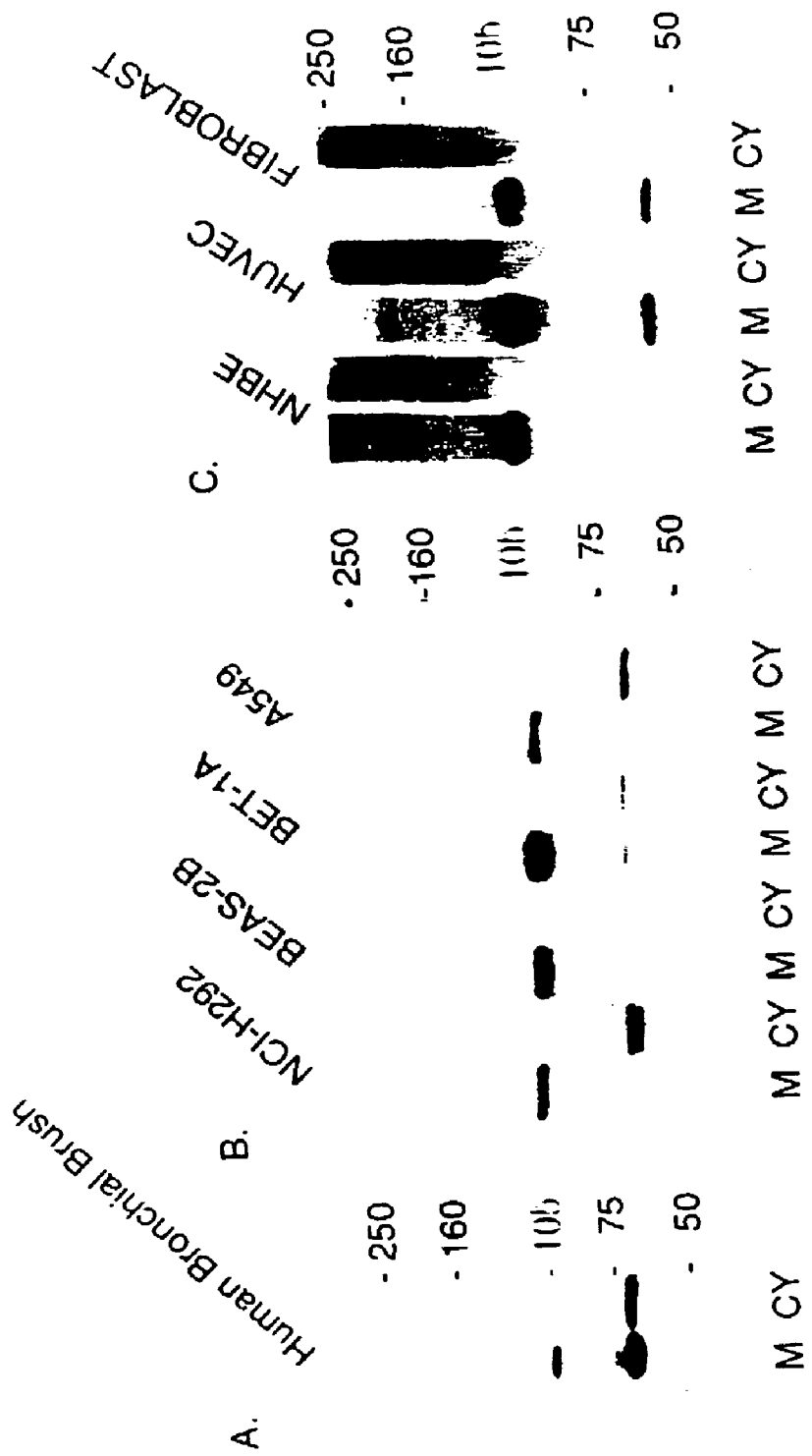
FIG. 5 provides Western immunoblots using polyclonal anti-ARTS-1 antisera and membrane and cytosolic fractions made from primary cells and cell lines. Panel A provides a Western immunoblot using human bronchial brush cells collected from human subjects. Panel B provides a Western immunoblot using the NCI-H292, BEAS-2B, BET-1A and A549 cultured cell lines. Panel C provides a Western immunoblot using primary cultures of normal human bronchial epithelial cells (NHBE), human umbilical vein endothelial cells (HUVEC) and human fibroblasts.

The expression of endogenous ARTS-1 polypeptide in primary cells and other cell lines was further investigated using the identical antiserum and Western immunoblot technique (See, FIG. 5). These experiments were conducted to determine if there were differences in the ARTS-1 polypeptide forms expressed in different cell lines. These experiments analyzed membrane and cytosolic fractions made from human bronchial brushing specimens, airway epithelial cell lines BEAS-2B and BET-1A, human lung carcinoma cell line A549, cultured NCI-H292 cells, primary cultures of normal human bronchial epithelial cells (NHBE), human umbilical vein endothelial cells (HUVEC) and human fibroblasts.

Similar to the NCI-H292 cell line, the BEAS-2B, BET-1A, NHBE and A549 cell lines all revealed a 100 kDa band localized predominantly in the membrane fraction, and a 68 kDa form expressed to varying degrees in the cytosolic fraction. The protein samples obtained from human bronchial brushings, as well as the HUVEC and fibroblast primary cells revealed similar patterns, with the exception that both the 100 and 68 kDa forms appear in the membrane fraction. The human bronchial brush cells and occasionally the NCI-H292 cell line also showed a larger 132 kDa form.

These multiple sized forms may be due to regulated processing of the ARTS-1 polypeptide. Furthermore, the distinction between the different sized ARTS-1 forms seen in the membrane versus the cytosolic fractions may also indicate regulated processing between the membrane and cytosol. However, it is not necessary to understand the mechanism of ARTS-1 processing or localization in order to practice the present invention, nor is it intended that the present invention be so limited.

Furthermore, in view of numerous alternative protocols known in the art for Western blotting, it is not intended that the present invention be limited to the Western blotting protocol provided in Example 5 or any other Western blotting method. For example, in some embodiments, alternative secondary (i.e., detection) antibodies can be used. Alternative Western irmnunoblotting protocols, reagents and equipment suitable for use in the present invention are known in the art (See, e.g., Ausubel et al. (eds.), *Current Protocols in Molecular Biology*, Section 10.8, "Immunoblotting and Inmmunodetection," John Wiley & Sons, Inc., New York [1994]).

VI. GST-ARTS-1 Polypeptide Expression and Purification

In order to facilitate the analysis of ARTS-1 biochemical activity, a highly purified form of the ARTS-1 polypeptide was produced using a GST fusion protein protocol commonly used in the art. The specifics of this protocol are provided in detail in Exarnple 6. It is not intended that the present invention be limited to any particular method for GST-ARTS-1 polypeptide expression, either with or without subsequent GST-ARTS-1 polypeptide purification.

The use of GST fusion proteins to produce purified polypeptides is common in the art. In these protocols, a transcriptional and translational fusion is made between the genes encoding glutathione-S-transferase (GST) and the gene of interest (e.g. the ARTS-1 gene). Production of the fusion protein containing a GST "tag" enables the effective and rapid purification of the fusion protein by use of an affinity column comprising immobilized glutathione. In order to produce a GST-ARTS-1 polypeptide, the cDNA sequence encoding ARTS-1 was first PCR amplified and subcloned into the pGEX plasmid backbone (Amersham Pharmacia) and used to transform the BL21 $E.\ coli$ host strain. The pGEX plasmid contains a multiple cloning site and expresses a fusion protein consisting of the GST polypeptide and a subcloned coding sequence (e.g., the ARTS-1 coding sequence) cloned into the multiple cloning site of the plasmid. Transcription of the fusion gene is controlled by the conditional tac promoter. In accordance with the manufacturer's protocol, clones were cultured in the presence of 0.6 mM isopropyl β-D-thiogalactoside (IPTG) and subsequently lysed with a protein extraction buffer. Transformed clones expressing GST-ARTS-1 fusion protein were selected by Western immunoblotting utilizing an anti-GST antibody (Amersham Pharmacia). Cells with confirmed expression of GST-ARTS-1 polypeptide were lysed and centrifuged to separate the soluble from the insoluble fractions. The GST-ARTS-1 fusion protein was isolated from the insoluble fraction by denaturation with 6M urea, then desalted and renatured. The GST-ARTS-1 fusion protein was purified utilizing a glutathione sepharose 4B affinity column using techniques well known in the art.

Figure 6:
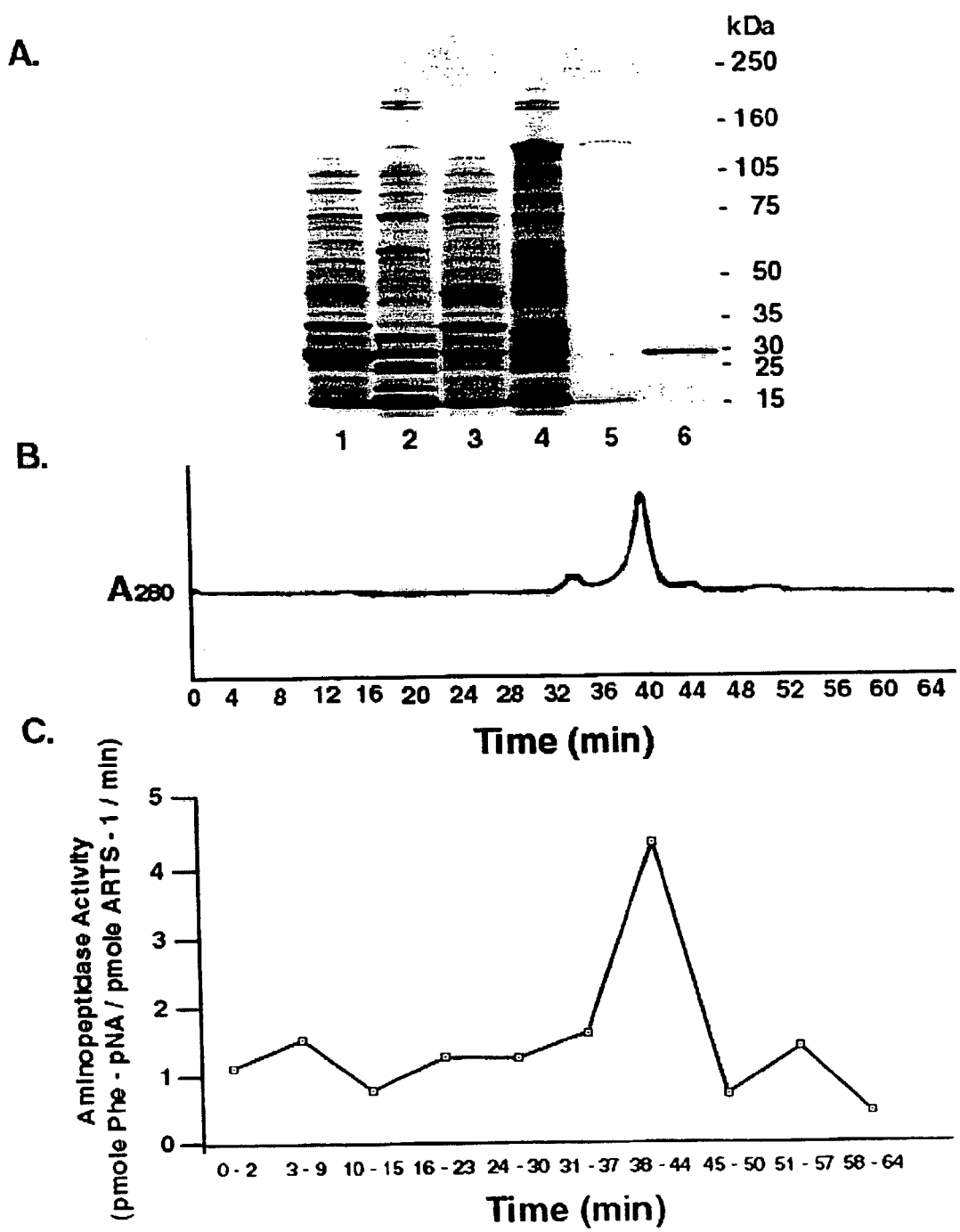
FIG. 6 provides results of an analysis of recombinant GST-ARTS-1 fusion protein purification and analysis of the aminopeptidase activity of this protein following purification. Panel A provides a Coomassie stained gel of protein samples obtained during the production and purification of the GST-ARTS-1 fusion protein. Panel B provides an FPLC elution profile of the purified GST-ARTS-1 fusion protein. Panel C provides the results of an assay of phenylalanine p-nitroaniline substrate aminopeptidase activity of the FPLC eluted fractions.

To assess the purity of the eluted recombinant GST-ARTS-1 fusion protein, samples were subjected to SDS-PAGE and stained with Coomassie brilliant blue, as shown in FIG. 6A. In this Figure, soluble and insoluble protein fractions from BL21 $E.\ coli$ transformed with empty pGEX vector are shown in lanes 1–2, and analogous samples from bacteria containing the pGEX-ARTS-1 vector are shown in lanes 3–4. The GST-ARTS-1 fusion protein following elution is shown in lane 5, as a predominant 132 kDa band, corresponding to the predicted molecular weight of a GST-ARTS-1 fusion protein (104 kDa ARTS-1 extracellular domain plus 26 kDa GST tag). The control purified GST tag was revealed as a predicted 26 kDa band in lane 6.

The recombinant purified GST-ARTS-1 fusion protein samples were further subjected to FPLC analysis to assess their purity, the results of which are shown in FIG. 6B. Elution from the FPLC column was monitored by absorbance at a wavelength of 280 nm. This analysis of the purified GST-ARTS-1 revealed a single major protein elution peak at approximately 40 minutes.

Using the aminopeptidase activity assay described below, FPLC fractions were assessed for aminopeptidase activity utilizing a phenylalanine p-nitroaniline substrate. The results of these experiments are shown in FIG. 6C. As indicated in this Figure, the single major protein peak revealed by FPLC analysis coeluted with a peak of aminopeptidase activity against a phenylalanine-pNA substrate in pooled fractions from 38–44 minutes.

As those of skill in the art know, numerous protocols for the purification of polypeptides are available. The use of numerous alternative protocols for the production of isolated ARTS-1 polypeptide are easily envisioned. These alternative protocols may be used to purify ARTS-1 polypeptides other than the GST-ARTS-1 polypeptide described by the present example. Indeed, it is not intended that the present invention be limited to any particular protocol.

Numerous reagents and variables may be manipulated or substituted for those used in Example 6 to yield a substantially similar purified ARTS-1 polypeptide. Such variables include the choice of ARTS-1 polypeptide (e.g., either with or without a fusion protein tag), the cells used for the production of the starting materials, the promoters/enhancers used to drive expression of the recombinant protein to be purified, the cellular culture and growth conditions, harvesting methods, mode of purification, and methods to assess polypeptide purity following purification. The detailed protocol provided in Example 6 is not meant to limit the scope of the present invention. Indeed, it is contemplated that any protocol which will produce a substantially similar purified product will find use with the present invention. Such alternative embodiments are briefly discussed below.

Alternative protocols may be used to purify forms of ARTS-1 polypeptide other than the GST-ARTS-1 fusion polypeptide provided by the present invention. These alternative forms may include a maltose binding protein (MBP) ARTS-1 fusion polypeptide, a polyhistidine (i.e., 6×His) tagged ARTS-1 fusion polypeptide, a thioredoxin tagged ARTS-1 fusion polypeptide, or a full length ARTS-1 polypeptide without any fused tag to facilitate purification.

Alternative protocols may find use in the present invention. For example, protocols which use different host systems as a source for starting material (i.e., a source culture) for ARTS-1 purification may be used. Such alternative source systems include insect cells with a baculovirus overexpression system (e.g., Sf9 or Sf21 cell lines), mammalian cell lines in conjunction with vectors designed for recombinant polypeptide overexpression (expression vectors), or mammalian cells or tissues for the purification of ARTS-1 polypeptide expressed from its endogenous (i.e., native) chromosomal location. The cultivation of the transformed, transfected or infected host of the invention is carried out in a medium and under conditions most appropriate for the growth of that particular host cell. These media formulations and culture conditions are well known to those in the art. For example, culture of a mammalian cell line for the isolation of an overexpressed or endogenous polypeptide will commonly use RPMI 1640 or DMEM media, typically supplemented with 5–10% fetal or newborn calf serum, and may be further supplemented with an antibiotic such as kanamycin or penicillin. In some protocols, calf serum may be omitted to facilitate subsequent polypeptide purification. Typically, the cultivation of mammalian cells is carried out in the presence 5% $CO_2$ at 37° C.

Following the cultivation of a particular ARTS-1 polypeptide-containing host, the proteins of the culture can be extracted by disrupting (by any suitable method) the microorganisms or cells if the protein is produced within the host. If ARTS-1 polypeptide of the invention is secreted by the host cells, the culture fluid is collected. The resultant culture extract or culture supernatant is then subjected to conventional biochemical techniques used for protein purification. As known in the art, numerous techniques for polypeptide purification exist (e.g., ammonium sulfate precipitation, gel chromatography, ion exchange chromatography, and affinity chromatography). These techniques may be used independently or in an appropriate combination to isolate and purify the polypeptide(s) of the present invention from a culture.

VII. Analysis of ARTS-1 Polypeptide Aminopeptidase Activity

In light of the homology between the polypeptide predicted from ARTS-1 gene with aminopeptidase members of the gluzincin zinc metalloprotease family, it was determined if ARTS-1 polypeptide had aminopeptidase activity, and furthermore, if the terminal aminopeptidase activity was specific for a particular amino acid or group of amino acids.

To accomplish this, commercially available amino acid p-nitroanilide substrates were incubated with purified GST-ARTS-1 fusion protein for 1 hour under conditions of linear enzyme activity over time. The rate of amide bond hydrolysis was determined by measuring the absorbance of the p-nitroaniline aminopeptidase reaction product at 380 nm. Each experimental point was run in triplicate and each determination utilized six concentrations of amino acid p-nitroanilide substrate. Kinetic constants were determined by Lineweaver-Burk analysis. Correlation coefficients for each line generated were greater than 0.997. The results of this analysis are shown in Table 3 below. Each amino acid p-nitroaniline substrate tested is shown in the left column, along with its polar/non-polar/acidic/basic nature. $V_{max}$ is a measure of the theoretical enzyme maximal velocity, $K_m$ is the Michaelis-Menten constant for each ARTS-1/substrate combination, $k_{cat}$ is the first order rate constant (i.e., the turnover number) for the ARTS-1/substrate combination, and $k_{cat}/K_m$ is the second order rate constant for the ARTS-1/substrate combination (i.e., a measure of overall catalytic efficiency).

As shown in Table 3, recombinant GST-ARTS-1 protein possessed selective aminopeptidase activity against non-polar amino acid substrates with a four-fold range of enzyme activity. Isoleucine-pNA was found to be the most favorable amino acid substrate based upon $k_{cat}/K_m$ determination, followed by Phe>Gly>Cys>Leu>Met>Ala>Pro>Val. Recombinant GST-ARTS-1 had no activity against either acidic (Asp or Glu) or basic (Arg, His, or Lys) amino acid substrates.

line was stably transfected with one of three constructs, all based on the pTarget vector. The pTarget vector contains elements which enable its selection following stable integration in the NCI-H292 cell line, and also has the ability to constitutively express a cloned insert in mammalian cells. The pTarget vectors used in this experiment were:

1) an empty pTarget vector,
2) pTarget vector containing the fuill length ARTS-1 cDNA coding region in the sense orientation,
3) pTarget vector containing ARTS-1 cDNA bases 61 to 213 in the anti-sense orientation (this region overlaps the putative transcription start site and intracellular and transmembrane domains).

Figure 7:
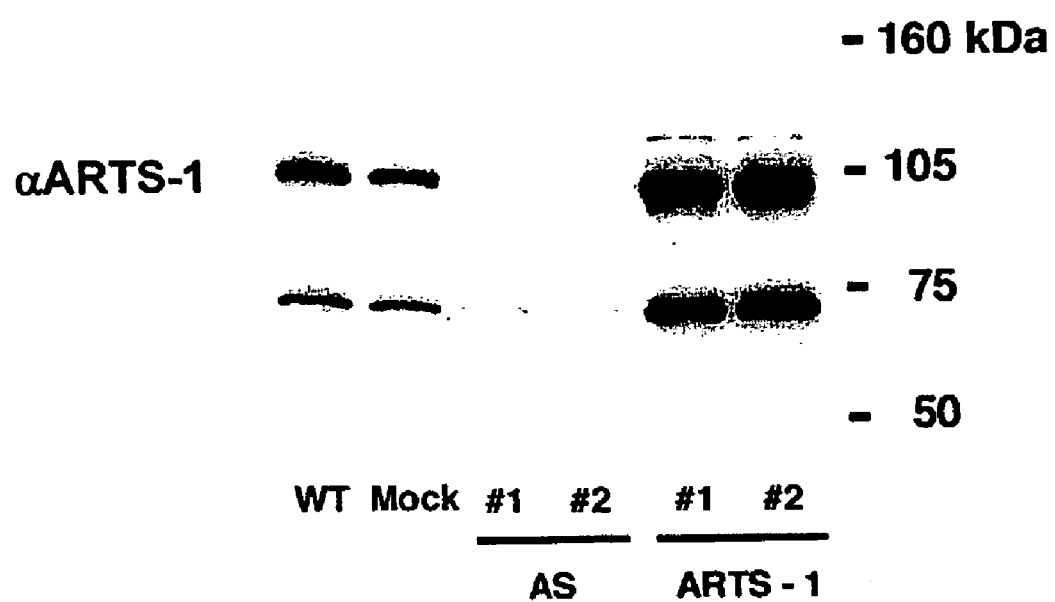
FIG. 7 provides a Western immunoblot using anti-ARTS-1 polyclonal antiserum as the primary antibody. Samples analyzed in the blot are from membrane protein fractions derived from stably transfected NCI-H292 cells which were untransfected (WT), control transfected (Mock), ARTS-1 sense-overexpressing (ARTS-1) or ARTS-1 antisense expressing (AS). Two independent clones each from the ARTS-1 and AS cell lines were analyzed.

Following the introduction and selection of these constructs in the host cell lines, membrane fractions were prepared from the lines and subject to Western immunoblotting in order to assess ARTS-1 polypeptide expression. This analysis was conducted according to the Western immunoblotting technique described in Example 5 and used the anti-ARTS-1 polyclonal antiserum produced as described in Example 4. The results of this analysis are shown in FIG. 7. In that Figure, two independent clonal lines containing ARTS-1 sense or antisense expressing vectors were analyzed. It was found that integration of the empty pTarget vector (Mock) had little effect on endogenous ARTS-1 expression compared to cells that did not contain any stably integrated plasmid (WT). The cell lines expressing the fuill length ARTS-1 cDNA in the sense orientation (ARTS-1) showed a significant increase in ARTS-1 protein expression, while the cell lines expressing the ARTS-1 antisense sequence (AS) showed significant reduction in ARTS-1 protein expression.

TABLE 3

Specificity and Rates of ARTS-1 Aminopeptidase Activity

| aa-pNA | Polarity | $V_{max}$ (pmol/pmol/min) | $K_m$ (mM) | $k_{cat}$ (s$^{-1}$) × 10$^{-2}$ | $k_{cat}/K_m$ (s$^{-1}$M$^{-1}$) |
|---|---|---|---|---|---|
| Ile | Non-polar | 5.81 ± 0.87 | 1.67 ± 0.02 | 9.68 ± 0.15 | 57.98 |
| Phe | Non-polar | 5.14 ± 0.04 | 1.66 ± 0.03 | 8.57 ± 0.06 | 51.61 |
| Gly | Non-polar | 8.67 ± 0.05 | 3.67 ± 0.03 | 14.45 ± 0.08 | 39.37 |
| Cys | Non-polar | 8.95 ± 0.31 | 4.57 ± 0.20 | 14.92 ± 0.52 | 32.64 |
| Leu | Non-polar | 9.45 ± 0.43 | 5.26 ± 0.25 | 15.75 ± 0.72 | 29.94 |
| Met | Non-polar | 13.36 ± 0.75 | 7.71 ± 0.43 | 22.27 ± 1.25 | 28.88 |
| Ala | Non-polar | 26.18 ± 0.24 | 16.84 ± 0.18 | 43.63 ± 0.40 | 25.91 |
| Pro | Non-polar | 5.29 ± 0.08 | 4.68 ± 0.06 | 8.82 ± 0.13 | 18.84 |
| Val | Non-polar | 5.31 ± 0.31 | 5.69 ± 0.26 | 8.85 ± 0.52 | 15.50 |
| Asp | Acidic | No Activity | — | No Activity | — |
| Glu | Acidic | No Activity | — | No Activity | — |
| Arg | Basic | No Activity | — | No Activity | — |
| His | Basic | No Activity | — | No Activity | — |
| Lys | Basic | No Activity | — | No Activity | — |

VIII. Analysis of ARTS-1 TNFR1 Ectodomain Sheddase Regulatory Activity

Figure 8:
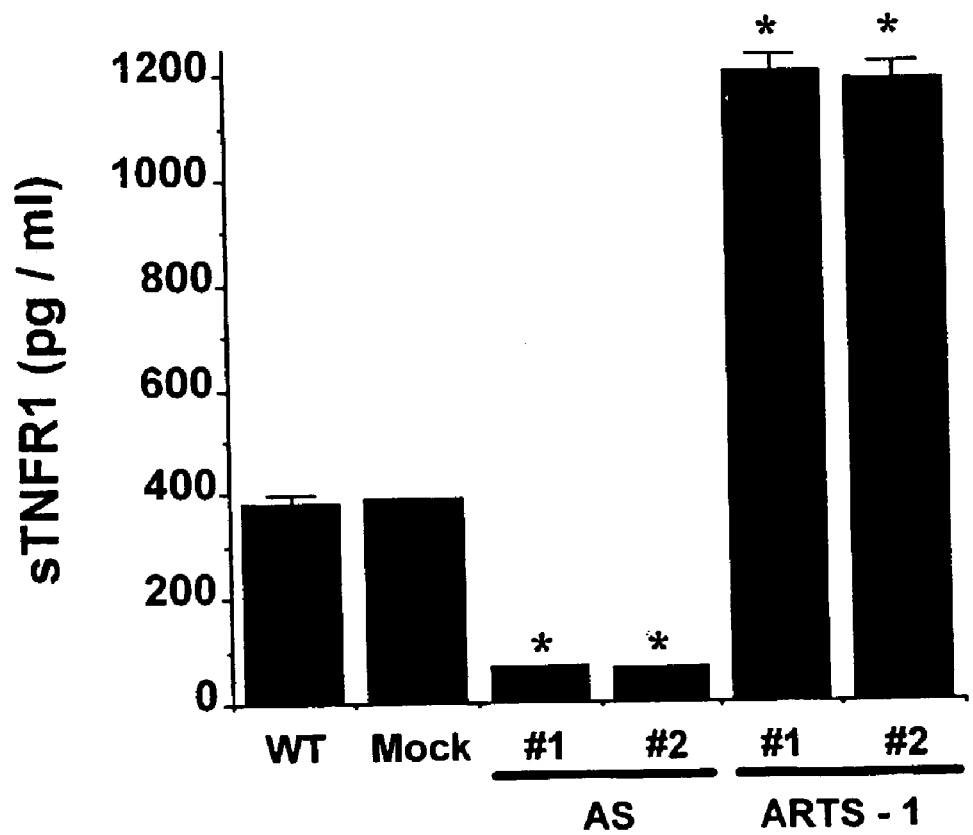
FIG. 8 provides results of an ELISA to determine the levels of sTNFR1 resulting from TNFR1 ectodomain shedding in cell culture supernatants from cultures of the same cell lines as indicated for FIG. 7.

In light of the ability of the ARTS-1 polypeptide to bind to the TNFR1 ectodomain in the yeast two-hybrid interaction assay and the peptidase/protease motif contained within the predicted polypeptide, the ability of ARTS-1 to promote the shedding of the TNFR1 ectodomain from the surface of human cells in culture was examined. The methods used in this experiment are described in detail in Examples 9 and 11. The results are depicted in FIGS. 7 and 8.

This experiment was done in two phases. The first phase involved construction of stably transfected cell lines which expressed either reduced or elevated levels of ARTS-1 polypeptide, as detailed in Example 9. The NCI-H292 cell The amount of TNFR1 ectodomain shedding occurring in each of these cell lines is depicted in FIG. 8. The levels of sTNFR1 ectodomain in cell culture supernatants from these cell lines were assayed using a commercially available sandwich-enzyme-linked immunosorbent assay (ELISA) technique (R & D Systems) with a lower limit of detection of 7.8 pg/ml. In FIG. 8, results are displayed as the mean of 5 independent experiments, with accompanying SEM (standard error of the mean). As shown in the Figure, the cell lines showing increased ARTS-1 protein expression (ARTS-1) also showed a significant increase in the amount of sTNFR1 present in cell culture supernatants as compared to cells transfected with the empty pTarget vector (Mock). Conversely, cell lines with decreased ARTS-1 protein expression (AS) showed significantly decreased levels of sTNFR1 in cell culture supernatants as compared to cells transfected with the empty pTarget vector (Mock).

Figure 11:
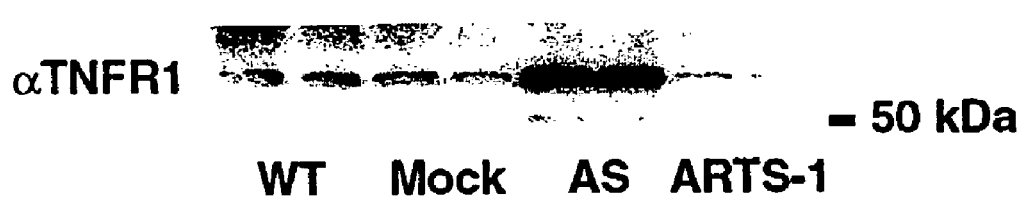
FIG. 11 provides a Western immunoblot using an anti-TNFR1 antibody as the primary antibody to detect membrane bound TNFR1. Samples analyzed in the blot include membrane protein fractions derived from stably transfected NCI-H292 cells which were untransfected (WT), control transfected (Mock), ARTS-1 sense-overexpressing (ARTS-1), or ARTS-1 anti-sense expressing (AS). Two independent clones of each cell line were analyzed.

The degree of TNFR1 ectodomain shedding as a function of ARTS-1 protein expression was also assessed indirectly by determining the relative amounts of membrane-bound TNFR1 fragment in each of the stably transfected cell lines described above using the Western immunoblotting technique described in Example 5. Crude membrane fractions from the stably transfected NCI-H292 cells described in Example 9 were prepared and resolved by SDS-PAGE and analyzed by Western immunoblotting using a murine anti-human TNFR1 monoclonal primary antibody (R & D System) which detects the membrane fragment of the TNF receptor. This Western blot is shown in FIG. 11. As shown in FIG. 11, cell lines over-expressing ARTS-1 (ARTS-1) demonstrated a decrease in membrane-associated TNFR1 relative to non-transfected (WT) or control transfected (Mock) cell lines, consistent with an increase in constitutive TNFR1 ectodomain shedding. Conversely, cell lines expressing anti-sense ARTS-1 mRNA (AS) demonstrated an increase in membrane-associated TNFR1 relative to non-transfected (WT) or control transfected (Mock) cell lines, consistent with a reduction in constitutive TNFR1 ectodomain shedding.

Figure 9:
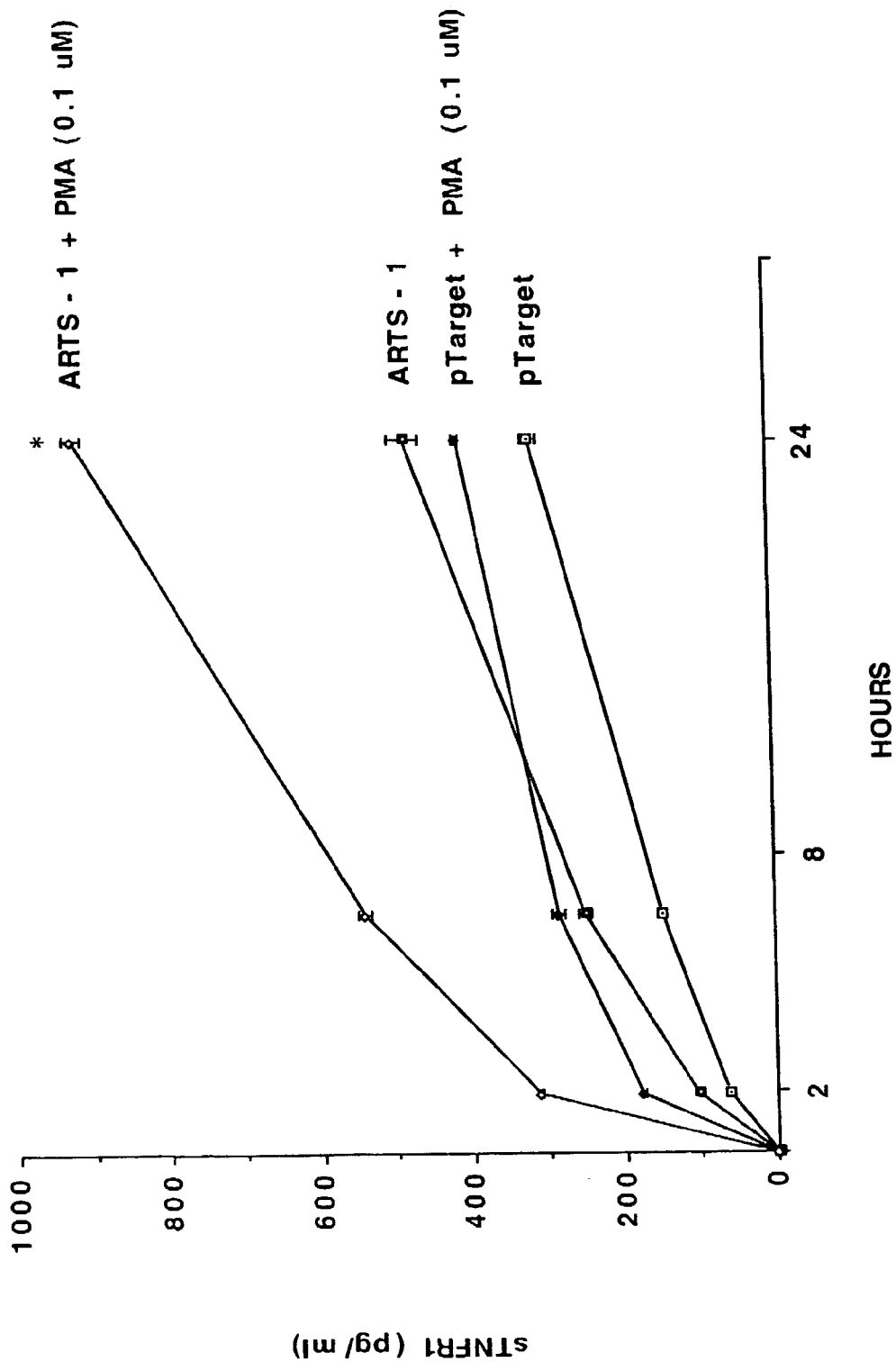
FIG. 9 provides a graph depicting the ability of ARTS-1 overexpression to potentiate the cleavage and shedding of TNFR ectodomain from the surface of NCI-H292 cells in response to PMA stimulation, as determined by an ELISA measuring sTNFR1 in the cell culture supernatants.
Figure 10:
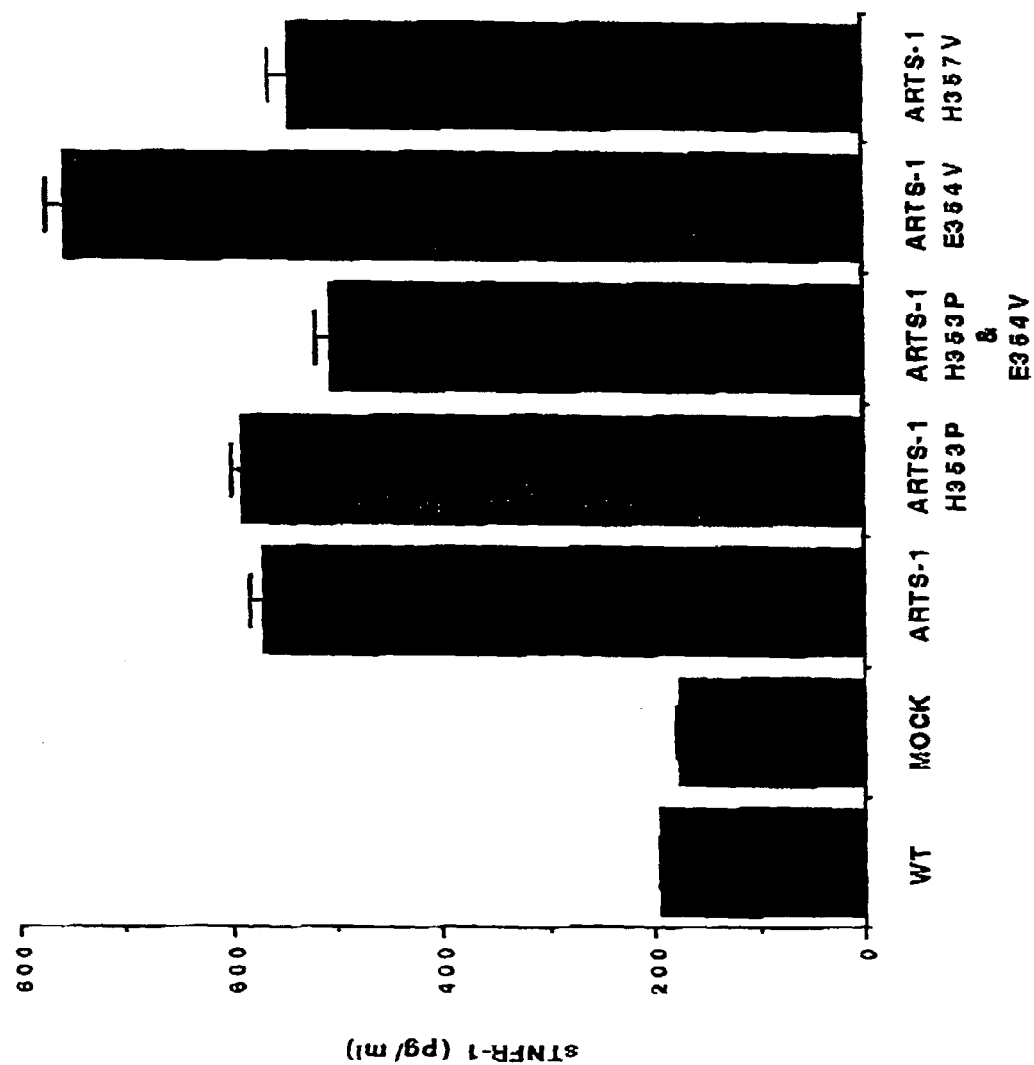
FIG. 10 provides a histogram showing the results of an ELISA analysis. The ELISA determined the levels of sTNFR1 (a measure of TNFR1 ectodomain shedding) in cell culture supernatants for stably transfected NCI-H292 cell lines expressing various ARTS-1 mutants.

Results from an experiment analyzing the ability of ARTS-1 overexpression to potentiate the shedding of TNFR ectodomain from the surface of NCI-H292 cells in response to PMA stimulation using these same cell lines are shown in FIG. 9. Cell lines overexpressing full length ARTS-1 mRNA were stimulated with 0.1 µM phorbol 12-myristate 13-acetate (PMA), which has previously been shown to upregulate sTNFR1 shedding in NCI-H292 cells (Levine et al., *Am. J. Respir. Cell Mol. Biol.*, 14:254–261 [1996]). As indicated in FIG. 9, the cell line containing only the empty pTarget vector showed only a modest increase in sTNFR1 shedding following 24 hours of PMA treatment. However, the cell line overexpressing the ARTS-1 cDNA showed a more dramatic increase in sTNFR1 shedding following 24 hours of PMA treatment, increasing from approximately 300 pg/ml to 415.3±4.5 pg/ml, increasing from 485±16.9 pg/ml to 914.2±9.5 pg/ml IX. Analysis of TNFR1 Ectodomain Sheddase Regulatory Activity of ARTS-1 Catalytic Mutants The predicted ARTS-1 polypeptide contains a peptidase/protease consensus motif found in the aminopeptidase family of gluzincin zinc metalloproteases. It was determined if this peptidase/protease catalytic motif was necessary for the ability of ARTS-1 to promote the shedding of the TNFR1 ectodomain. To conduct this experiment, a series of mutants containing point mutations predicted to abolish the ARTS-1 peptidase/protease activity were constructed. The construction of cell lines expressing these mutants was conducted as described in the section above, with experimental details provided in Examples 10 and 11. Results of this experiment are depicted in FIG. 10.

The experiment was done in two phases. The first phase involved construction of stably transfected cell lines which expressed either wild-type or mutant forms of the ARTS-1 polypeptide. The ARTS-1 mutants constructed for this experiment were designed to eliminate metalloprotease catalytic activity by disrupting the zinc metalloprotease consensus catalytic motif HEXXH(Y)$_{18}$E (SEQ ID NO:10; consisting of a zinc binding and catalytic site domains). In the ARTS-1 polypeptide, this motif is located at H$^{353}$ELAH(Y)$_{18}$E$^{376}$ (SEQ ID NO:11). Each of the mutations made lies within this domain. These mutations are H353P, E354V, H353P and E354V in combination, and H357V. These mutations have been previously shown to abolish zinc binding and/or catalytic (enzymatic) activity in proteins containing the motif (Devault et al., *FEBS Lett.*, 23154–23158 [1988]; Devault et al., *J. Biol. Chem.*, 263: 4033–4040 [1988]; Vallee and Auld, *FEBS Lett.*, 257:138–140 [1989]; Vallee and Auld, *Biochemistry* 29:5647–5659 [1990]; and Wang and Cooper, *Proc. Natl. Acad. Sci. USA* 90:1222–1226 [1993]).

Six cell lines were created by stably transfecting the NCI-H292 cells with the six constructs, all based on the pTarget expression vector. These constructs (and resulting cell lines) contained:

1) an empty pTarget vector,
2) the ARTS-1 cDNA (WT) coding region,
3) the ARTS-1 cDNA encoding a H353P mutation,
4) the ARTS-1 cDNA encoding a E354V mutation,
5) the ARTS-1 cDNA encoding a H353P and E354V double mutation, and
6) the ARTS-1 cDNA encoding a H357V mutation.

Following the introduction and selection of these constructs in the host cell lines, the amount of TNFR1 ectodomain shedding occurring in each of the lines was determined by measuring the levels of sTNFR1 ectodomain in cell culture supernatants using a commercially available sandwich-enzyme-linked immunosorbent assay (ELISA) technique (R & D Systems) with a lower limit of detection of 7.8 pg/ml. These results are depicted in FIG. 10 as the mean of five independent experiments, as well as the SEM (standard error of the mean). As shown in this Figure, the cell line containing the recombinant ARTS-1 cDNA with no mutations (ARTS-1) showed a significantly elevated level of sTNFR1 in the culture supernatant compared to cell lines containing no integrated DNA (WT) or containing the empty pTarget vector (MOCK). Unexpectedly, each of the cell lines containing mutant forms of the ARTS-1 polypeptide also showed elevated levels of sTNFR1 compared to the control lines (i.e., WT and MOCK lines). This experiment demonstrates an unexpected property of the present invention, as the peptidase/protease activity of the ARTS-1 polypeptide appears not to be required for its sTNFR1 shedding regulatory activity.

X. Analysis of ARTS-1/TNFR1 Interaction In Vivo

In light of the of the identification of the ARTS-1 gene by the yeast two-hybrid interaction screening, the physical association of ARTS-1 and TNFR1 was verified in vivo in a mammalian cell culture system using a co-immunoprecipitation assay.

Crude membrane fractions from cultured NCI-H292 cells were isolated and incubated with murine anti-human TNFR1 monoclonal antibody (R & D System) or 1 ml of anti-ARTS-1 antiserum overnight. Following the incubation, the resulting antibody complexes were immunoprecipitated using immobilized protein A/G beads (Pierce), and the precipitated proteins analyzed by Western immunoblotting.

Figure 12:
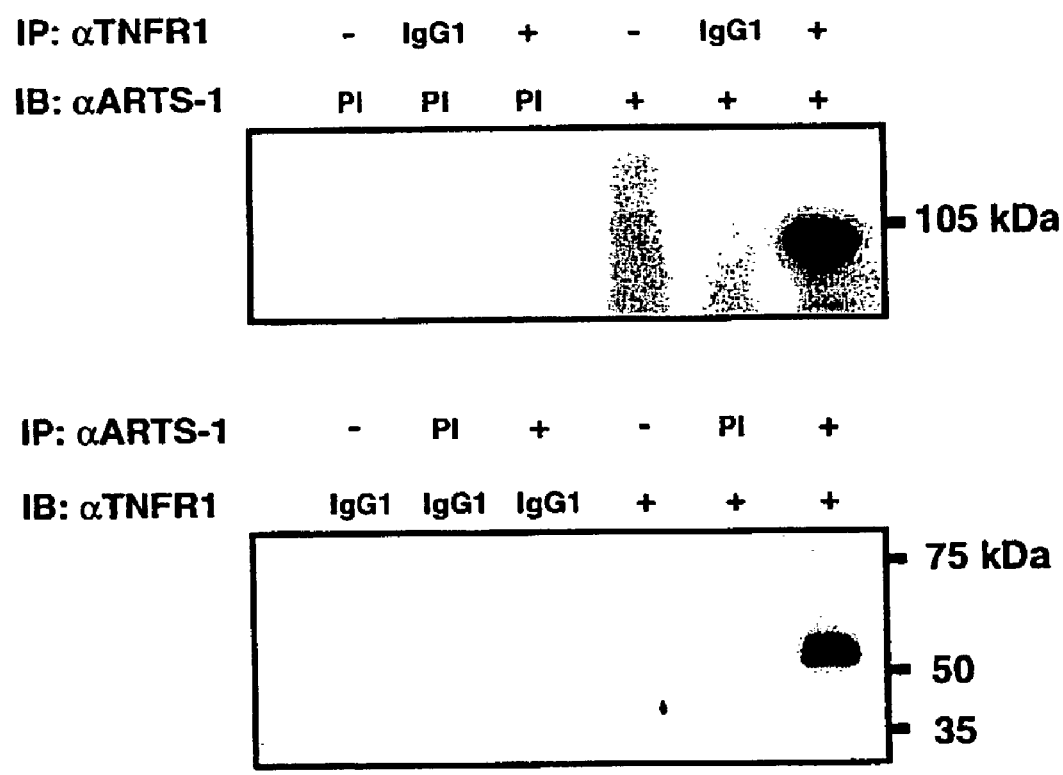
FIG. 12 provides two Western immunoblots following two in vivo immunoprecipitation experiments using membrane protein fractions isolated from cultured NCI-H292 cells. In the top panel, an anti-TNFR1 antibody was used in the immunoprecipitation step (indicated as "IP"), and anti-ARTS-1 antiserum was used as the primary antibody in the immunoblotting (indicated as "IB"). Conversely, in the lower panel, the anti-ARTS-1 antiserum was used in the immunoprecipitation, while the anti-TNFR1 antibody was used as the primary antibody in the immunoblotting.

Two different combinations of precipitation and immunoblotting antibody were used. The results of these immunoprecipitation experiments are shown in FIG. 12. In one experiment (FIG. 12, top panel), the anti-TNFR1 antibody was used in the immunoprecipitation (indicated as "IP" in the Figure), and the anti-ARTS-1 antiserum was used as the primary antibody in the immunoblotting (indicated as "IB" in the Figure). In a second experiment (FIG. 12, bottom panel), the antibodies were reversed, where the anti-ARTS-1 antiserum was used in the immunoprecipitation, while the anti-TNFR1 antibody was used as the primary antibody in the immunoblotting.

As shown in FIG. 12, immunoprecipitation of the NCI-H292 cell membrane proteins with an anti-TNFR1 monoclonal antibody resulted in the coprecipitation of the 100 kDa ARTS-1 species and, conversely, immunoprecipitation with anti-ARTS-1 antiserum coprecipitated the 55 kDa TNFR1. These results indicate an in vivo protein-protein interaction between ARTS-1 and TNFR1 proteins.

Figure 13:
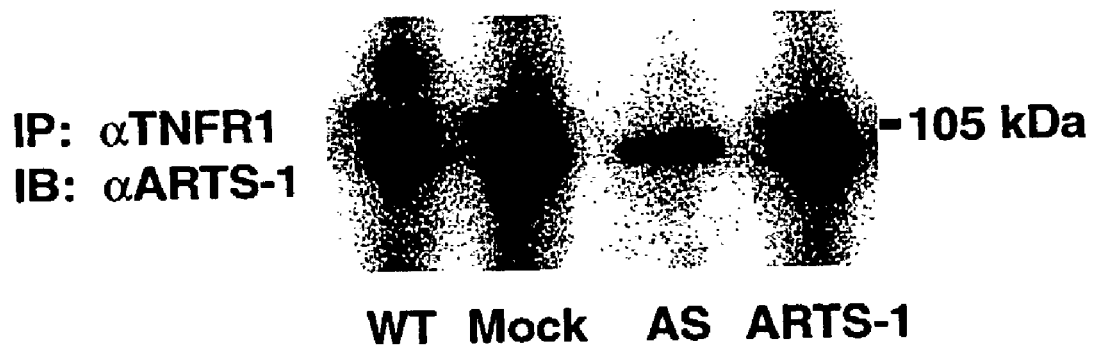
FIG. 13 provides a Western immunoblot following an in vivo immunoprecipitation experiment using an anti-TNFR1 monoclonal antibody for the immunoprecipitation and anti-ARTS-1 antiserum as the primary antibody in the blot. The immunoprecipitations used cell membrane protein fractions derived from stably transfected NCI-H292 cells overexpressing ARTS-1 (ARTS-1), expressing an anti-sense ARTS-1 message (AS), as well as control-transfected (Mock) and non-transfected (WT) cell lines.

Similar immunoprecipitation experiments were also performed using the stably-transfected NCI-H292 cell lines described in Example 9. In this experiment, the anti-TNFR1 antibody was used to immunoprecipitate protein from the various membrane protein fractions, and the resulting immunoprecipitate was examined by Western immunoblotting using anti-ARTS-1 antiserum as the primary antibody. As shown in FIG. 13, immunoprecipitation using an anti-TNFR1 monoclonal antibody of cell membrane protein derived from the anti-sense ARTS-1 cell line (AS) showed decreased amounts of ARTS-1 protein as compared to control-transfected (Mock) or non-transfected (WT) cells, consistent with decreased ARTS-1 protein expression in anti-sense ARTS-1 cells. No increase in ARTS-1 protein levels relative to control cell lines was detected following immunoprecipitation of ARTS-1 overexpressing cell lines with an anti-TNFR1 monoclonal antibody, which likely reflects increased TNFR1 shedding related to ARTS-1 overexpression.

XI. Therapeutic Agents to Treat Immune Diseases and Disorders

The present invention provides at least one polypeptide which promotes the shedding of TNFR1 (i.e., ARTS-1 polypeptide) from the surface of cultured human cells, a gene encoding the polypeptide, recombinant vectors comprising the gene, host cells comprising the vectors and antibodies directed against the ARTS-1 polypeptide. It is contemplated that these compositions will find use as therapeutic agents for the treatment of TNF-mediated immune diseases. It is contemplated that the therapeutic agents or the agents for gene therapy of the present invention will be administered to a subject orally, parenterally, systemically or locally. It is also contemplated that genes and polypeptides which are substantially homologous to the ARTS-1 gene provided by the present invention will also find use in the treatment of TNF mediated diseases and disorders.

When compositions of the present invention are used as therapeutic agents or agents for gene therapy for immune diseases, it is not intended that the present invention be limited to a particular disease. For example, the gene or polypeptide of the invention may be used, alone or in combination, to treat inflammatory diseases including, but not limited to, rheumatoid arthritis, inflammatory bowel disease, septic shock, cachexia, autoimmune disorders, graft-versus-host disease and insulin resistance.

In some preferred embodiments of the present invention, when the therapeutic agent of the invention is administered orally, the agent may be formulated into a tablet, capsule, granule, powder, pill, troche, liquid drops, suspension, emulsion, syrup or the like. Alternatively, the therapeutic agent may be prepared into a dry product which is re-dissolved just before use. In preferred embodiments, when the therapeutic agent of the invention is administered parenterally, the agent may be formulated for intravenous injection, intramuscular injection, intraperitoneal injection, subcutaneous injection, as a suppository, etc. Injections are supplied in the form of unit dosage ampules or multi-dosage containers. The formulations of the present invention may be prepared by conventional methods using appropriate excipients, fillers, binders, wetting agents, disintegrating agents, lubricating agents, surfactants, dispersants, buffers, preservatives, dissolution aids, antiseptics, flavoring/perfuming agents, analgesics, stabilizers, isotonicity inducing agents, etc. conventionally used in pharmaceutical preparations.

Each of the above-described formulations may contain pharmaceutically acceptable carriers or additives. Specific examples of such carriers or additives include water, pharmaceutically acceptable organic solvents, collagen, polyvinyl alcohol, polyvinylpyrrolidone, carboxyvinyl polymers, sodium alginate, water-soluble dextran, sodium carboxymethyl amylose, pectin, xanthan gum, gum arabic, casein, gelatin, agar, glycerol, propylene glycol, polyethylene glycol, vaseline, paraffin, stearyl alcohol, stearic acid, serum albumin, mannitol, sorbitol and lactose. One or a plurality of these additives are selected or combined appropriately depending on the form of the preparation.

The dosage levels of the therapeutic agent of the invention will vary depending on the age of the subject, the route of administration and the frequency and duration of administration and may be varied over a wide range as suitable for each subject. When an effective amount of the polypeptide or antibody of the invention is administered in combination with an appropriate diluent and a pharmaceutically acceptable carrier, the effective amount of the polypeptide or antibody is in the range from 0.01 to 1000 mg/kg per administration, although other amounts are contemplated, as appropriate. One skilled in the art is capable of determining the therapeutically effective amount appropriate any given circumstances. In some embodiments, the therapeutic agent is administered once a day or in several dosages per day for at least one day.

In some embodiments of the present invention, at least one gene of the present invention is used as an agent for therapy for immune diseases or disorders. When used as a therapeutic agent, the gene(s) may be administered systemically or locally. The gene(s) may be delivered by direct application of the nucleic acid to cells or tissues.

In one embodiment, the present invention is used as a gene therapy agent to treat an inflammatory disease or condition. In one embodiment, the gene therapy agent of the present invention is delivered via a viral delivery system. In an alternative embodiment, the gene therapy agent of the present invention involves a non-viral delivery system.

Viral-mediated gene delivery has been shown to be an effective mechanism for gene delivery for use in gene therapy. Indeed, methods for viral-mediated gene therapy have recently been shown to be effective in human and non-human systems (Kordower et al., *Science* 290:767–773 [2000]; Lee et al., *Nature* 408:483–488 [2000]; Cavazzana-Calvo et al., *Science* 288:669–672 [2000]; Kay et al., *Nature Genetics* 24:257–261 [2000]; Amado and Chen, *Science* 285:674–676 [1999]; Burton et al., *Proc. Natl. Acad. Sci. USA* 96(22):12725–12730 [1999]; Zhang, *Cancer Gene Ther.*, 6(2):113–138 [1999]; Connelly et al., *Blood* 91(9): 3273–3281 [1998]; and Connelly et al., *Blood* 88(10): 3846–3853 [1996]). A number of viruses have been demonstrated to be effective or potentially effective tools in recombinant gene delivery to subjects, including adenovirus (lentivirus) vectors, adeno-associated virus vectors, herpes virus vectors, vaccinia virus vectors, and retrovirus vectors. In some preferred embodiments, the recombinant viral vector comprising the ARTS-1 gene of the present invention comprises nucleic acid elements operably linked for the purpose of transcribing and translating the gene of the invention in cells in a subject. In preferred embodiments, these nucleic acid elements consist of a nucleotide sequence encoding the ARTS-1 polypeptide, and operably linked promoter and enhancer elements for expression of the ARTS-1 gene. In some embodiments, these promoter/enhancer elements are widely active in all or many cell types, and direct constitutive expression of the gene (e.g., cytomegalovirus (CMV), SV40 or Rous sarcoma virus (RSV) promoter/enhancer sequences). In alternative embodiments, operably linked promoter/enhancer elements are restricted in activity to a single cell type or tissue (e.g., cardiac-specific or liver-specific promoter/enhancers) (Maniatis et al., *Science* 236:1237–1245 [1987]; Voss et al., *Trends Biochem. Sci.*, 11:287 [1986]). In further embodiments, a promoter/enhancer element that imparts inducible (i.e., conditional) expression of an operably linked open reading frame (e.g., tetracycline inducible or repressible promoters) is used. Furthermore, in other embodiments, operably linked nucleotide sequences include sequences directing proper translation initiation, post-transcriptional splicing/editing, and/or polyadenylation. In still other embodiments, in addition to containing nucleotide sequences controlling the expression of the ARTS-1 gene, a viral gene therapy vector further contains the necessary nucleotide sequences for in vitro replication and propagation of the virus, production of infective virion particles, and sequences that impart stability of the DNA in a cellular host (although many viral functions require the presence of a "helper virus"). Collectively, such sequences are sometimes referred to as the viral "backbone."

Additionally, a genetic sequences of the invention may be enclosed in phospholipid vesicles such as liposomes, and the resultant liposomes administered to a subject. Liposomes are biodegradable vesicles containing an internal aqueous region surrounded by a lipid bilayer. This structure is able to encapsulate materials (e.g., at least one gene of the present invention). By mixing at least one gene of the present invention with phospholipid starting material, a liposome-gene complex will form. Subsequently, when this complex is cultured with cells, the gene(s) in the complex is taken into the cells (i.e., via lipofection). A liposome-gene complex comprising at least one gene of the present invention can be administered to a subject, either locally or systemically. In addition to liposomes, a plasmid encoding the gene(s) of interest may be used.

Alternatively, direct DNA administration, liposome gene transfer, or viral vector, all comprising at least one gene of the present invention, can be used to transfect cells ex vivo (i.e., not within the subject), followed by the transplantation of the recipient cells into the subject. The source of the cells receiving the gene(s) of the invention can be cells that have been removed from the subject, or cells from some other source. Following delivery of the gene(s) of the present invention into these cells, the cells are then placed into the subject to provide therapeutic value.

In some embodiments of the present invention, methods are contemplated for administering gene(s) of the invention locally to tissues via surgical or injection protocols, as well as systemically, such as by intravenous or intra-arterial administration. Further, an administration method combined with catheter techniques and surgical operations may also be employed.

The dosage levels of the agent for delivering the gene(s) of the invention vary depending on the age, sex and conditions of the subject, the route of administration, the number of times of administration, and the type of the formulation, among other considerations. One skilled in the art is capable of determining the therapeutically effective amount appropriate any given circumstances. Usually, it is appropriate to administer a gene of the invention in an amount of 0.1–100 mg/adult body/day, although other concentrations are contemplated, as appropriate.

XII. Diagnostic Agents for Immune Diseases and Disorders

It is contemplated that the ARTS-1 gene of the present invention will find use as a diagnostic marker for TNF signaling activity. Indeed, levels of ARTS-1 mRNA or ARTS-1 polypeptide in biological samples (e.g., blood, urine, serum or any other body fluid) are useful indicators of the levels of TNF signaling activity in vivo. It is contemplated that the presence of elevated ARTS-1 mRNA and/or polypeptide levels correlate with decreased TNF signaling activity, while reduced levels of ARTS-1 mRNA or polypeptide correlate with increased TNF activity. It is contemplated that excessive or inadequate TNF activity is indicative of disease or pathological states. Thus, the present invention provides methods and compositions for rapid quantitation of ARTS-1 mRNA and polypeptide indicative of TNF signaling activity, thereby providing useful tools for assessing the immune condition of an individual suspected of suffering from TNF-mediated immune disorders or diseases. In contrast, existing methods for the assay of TNF activity involve lengthy tissue culture assays which are not readily applicable for use as a rapid diagnostic tool in a clinical setting (Suffredini et al., *J. Immunol.*, 155:5038–5045 [1995]; Suffredini et al., *N. Eng. J. Med.*, 321:280–287 [1989]; and Eskandari et al., *Immunol. Invest.*, 19:69–79 [1990]).

The present invention further provides compositions for use in diagnostic kits which can be used to rapidly assess ARTS-1 mRNA or polypeptide using either a nucleic acid probe specific for ARTS-1 mRNA, or PCR primers capable of amplifying ARTS-1 mRNA (all derived from the nucleic acid of SEQ ID NO:1) or the antibody directed against at least a portion of an ARTS-1 polypeptide. Such kits may be designed to incorporate PCR, nucleic acid probe hybridization, and/or antibody immunoassay protocols for ARTS-1 marker detection. These kits may further include any reagent(s) or material(s) which makes possible or facilitates the analysis of a sample (e.g., apparatus for sample collection, sample tubes, holders, trays, racks, dishes, plates, instructions to the kit user, solutions or other chemical reagents, and samples to be used for standardization, normalization, and or as control samples).

XIII. Identification of Genes Substantially Homologous to ARTS-1

In other embodiments, the present invention provides compositions and methods for the identification of genes substantially homologous to the ARTS-1 gene (i.e., SEQ ID NO:1). It is contemplated that genes similar to the gene set forth in SEQ ID NO:1 have the ability to regulate the cleavage and shedding of TNFR1 ectodomain. In particular, it is contemplated that the compositions and methods of the present invention will find use in stringent hybridization and/or PCR methods to identify genes substantially homologous to SEQ ID NO:1.

It is further contemplated that genes similar to the gene set forth in SEQ ID NO:1 have the ability to regulate the cleavage and shedding of the ectodomains of other pro-inflammatory cytokine receptors (e.g., type II IL-1 receptor and IL-6 receptor). As discussed above, TNF, IL-1 and IL-6 all are multi-functional pro-inflammatory cytokines which regulate acute phase protein production during innate immune responses to infection and tissue injury (Suffredini et al., *J. Clin. Immunol.*, 19:203–214 [1999]). Consequently, it is contemplated that genes significantly homologous to ARTS-1 will find utility in the treatment of immune disorders or diseases mediated by abnormal TNF, IL-1 or IL-6 activity. It is contemplated that the methods and compositions of the present invention will find use in promoting the cleavage and shedding of the TNFR1 ectodomain, as well as the ectodomains of IL-1 and IL-6 cytokine receptors. Although it is not intended that the present invention be so limited, two methods for isolation of genes substantially homologous to the ARTS-1 gene are provided below.

A. Hybridization to Identify Genes Significantly Homologous to the ARTS-1 Gene

In this method, a probe derived from the nucleic acid of SEQ ID NO:1 is used to screen a phage EDNA library. The probe is preferably derived from the ARTS-1 gene coding region. The probe may be an oligonucleotide amplified or excised from a larger nucleic acid (e.g., from a purified restriction digest product of a plasmid or other vector) or produced synthetically, recombinantly or by PCR amplification. There is no limitation on the size of the probe, although it is preferably longer than 25 nucleotides, and most preferably encompasses the entire coding region of the ARTS-1 cDNA. This probe may be single or double stranded. In particularly preferred embodiments the probe is labelled with a "reporter molecule," so that is detectable in a detection system of choice. A detection system may include, but is not limited to, enzymatic detection, fluorescence, radioactivity, and luminescent systems. Indeed, it is not intended that the present invention be limited to any particular detection system or label.

As a source of nucleic acid to be used in the hybridization screening, it is contemplated that nucleic acid from a wide variety of eukaryotic sources may be used. However, λgt10-based EDNA bacteriophage libraries derived from human sources are preferred and advantageous in this embodiment of the invention. Nonetheless, the source of the nucleic acid to be screened is by no means limited.

Example 1 provides experimental protocols used in the development of the present invention, and specifically, a protocol for the screening of a phage plaque library with a radiolabelled DNA probe. This same protocol finds use in identification of genes which are substantially homologous to SEQ ID NO:1. Briefly, a bacteriophage cDNA library is plated in a lawn of DH-5α host bacteria. The DNA contained in each of the plaques is replica plated via a plaque-lift onto a membrane suitable for subsequent hybridization. The DNA is fixed to the filter, and probed in solution using the ARTS-1 derived probe under stringent conditions. Phage plaque DNA with the ability to hybridize to the probe is isolated, analyzed and sequenced.

B. PCR to Identify Genes Significantly Homologous to the ARTS-1 Gene

PCR may be used to identify genes significantly homologous to the ARTS-1 gene. In a preferred embodiment, a sense primer and an anti-sense primer derived from the polypeptide coding region of the ARTS-1 gene are synthesized and used in a polymerase chain reaction (PCR). In an alternative embodiment, "degenerate" PCR primers are used. In these embodiments, the PCR primers have nucleotide sequences which encode amino acid domains of the ARTS-1 polypeptide, but differ from the ARTS-1 gene nucleotide sequence. Criteria for designing "degenerate" PCR primers are well known in the art. It is not intended that the present invention be limited to any particular primer or primer set.

It is also contemplated that nucleic acid from a wide variety of eukaryotic sources may be used as template in the PCR methods. It is not intended that the present invention be limited as to the source of the template nucleic acid. However, nucleic acid template derived from human sources is the most preferred embodiment of the present invention.

In preferred PCR methods, a nucleic acid that is substantially homologous to the ARTS-1 gene is amplified using materials and methods known in the art. Conditions of the PCR may be manipulated (e.g., the duration or temperature of the cycle times may be changed) to amplify a nucleic acid substantially homologous to the ARTS-1 gene. Indeed, it is contemplated that many suitable PCR conditions as known in the art will find use in the present invention. The nucleic acid amplified in the PCR reaction is visualized, isolated, subeloned, and sequenced using techniques standard in the art.

The isolated nucleic acid obtained by either plaque hybridization or PCR is further examined to determine if the isolated nucleic acid is "substantially homologous" to the ARTS-1 gene of the present invention based on criteria previously discussed. In a preferred embodiment, the isolated nucleic acid which is substantially homologous to the ARTS-1 gene encodes a polypeptide having the ability to promote the cleavage and shedding of at least one of the ectodomains of the group of cytokine receptors consisting of TNFR1, and IL-1 and IL-6 cytokine receptors. The nucleic acid obtained is then tested using methods such as those described in Examples 7, 11, 12 and 13. In a most preferred embodiment, the isolated gene has TNF regulatory activity, as determined using the protocol supplied in Example 14.

XIV. Methods for Drug Screening

It is contemplated that compounds which are able to regulate ARTS-1 activity or receptor ectodomain shedding are candidates for further development as therapeutically advantageous drugs. Such drugs find use as immune response modifiers, to either enhance or attenuate the action of an cytokine signalling (e.g., TNF, IL-1 or IL-6). The present invention provides compositions and methods for the screening and identification of test compounds which can regulate ARTS-1 activity, ARTS-1 transcript or protein expression, and receptor shedding, and thus, identifies drug candidates for further development as therapeutics. However, an understanding of the mechanism(s) of how a particular compound regulates cytokine signalling and proinflammatory immune responses is not necessary in order to use the present invention.

A. Method for Drug Screening to Identify Compounds Having the Ability to Regulate ARTS-1 Expression The present invention provides screening methods to identify compounds which can regulate the level of ARTS-1 transcript or protein in a tissue. Test compounds which are able to regulate ARTS-1 transcript or protein levels in a cell or tissue are candidates for further development as therapeutic agents. It is contemplated that compounds which can upregulate or downregulate ARTS-1 expression also have the ability to downregulate or upregulate cytokine signalling (i.e., a proinflammatory immune response), respectively.

In one embodiment of the present invention, the screening method uses Northern blotting to assess the levels of the ARTS-1 transcript in a cell culture following exposure of the culture to a test compound. In this embodiment, cultured cells are exposed to a test compound, and samples of tissue are collected at intervals ranging from approximately 0 to 48 hours. RNA is isolated from these cells and subjected to Northern blot analysis, as described in Example 3, using a probe specific for the ARTS-1 mRNA. Comparison of the ARTS-1 transcript levels before and after exposure to the test compound identifies those compounds that upregulate or downregulate ARTS-1 transcript levels. It is contemplated that compounds that can regulate ARTS-1 transcript levels provide targets for further development as therapeutic agents.

In a preferred embodiment, cultured human NCI-H292 pulmonary mucoepidermoid carcinoma cells are used in the screening. However, it is not intended that the invention be limited to the use of only this cell type, as other cell types are equally suitable, and are known to those in the art. Similarly, it is not intended that the reagents, methods or apparatus for RNA collection and analysis be limited to those described herein, as numerous suitable equivalents are known to those in the art.

Figure 14:
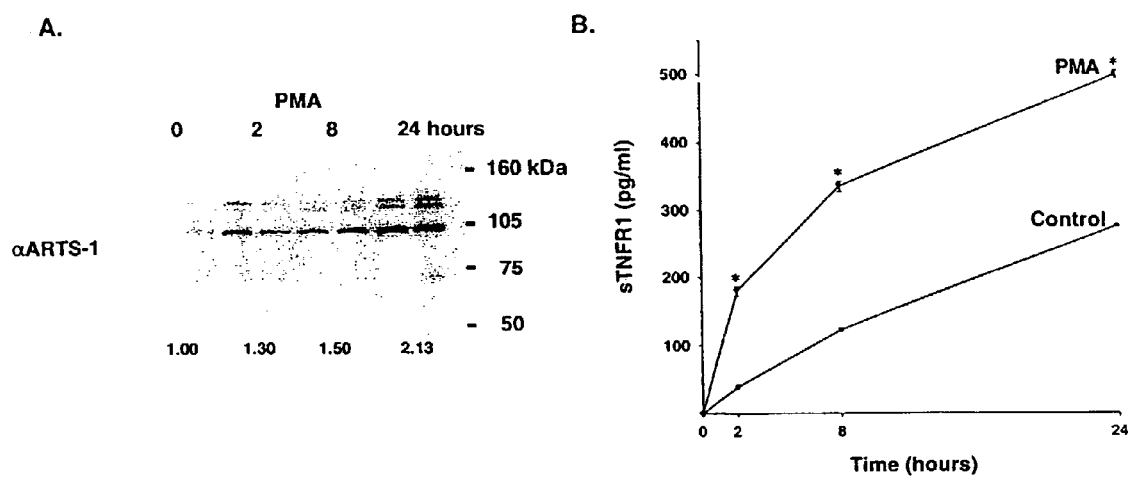
FIG. 14 provides results of two drug screening assays. Panel A provides a Western immunoblot using anti-ARTS-1 polyclonal antiserum as the primary antibody, tested with membrane protein fractions from NCI-H292 cells following exposure to 4b-phorbol 12-myristate 13-acetate (PMA) (over a time course). Panel B provides the results of an ELISA to determine the levels of sTNFR1 in cell culture supernatants from NCI-H292 cell cultures following exposure PMA, over time.

In another embodiment of the screening method of the present invention, Western immunoblotting is used to assess the levels of ARTS-1 protein following exposure of a cell culture to a test compound. In this embodiment, cultured cells were exposed to a test compound, in this case, 4b-phorbol 12-myristate 13-acetate (PMA), and samples of tissue were collected at 0, 2, 8 and 24 hours following the exposure. Membrane proteins were isolated from these cells and subjected to Western immunoblot analysis, as described in Examples 4 and 5, using antiserum specific for the ARTS-1 protein. Results of this screening are shown in FIG. 14, Panel A. Comparison of the ARTS-1 protein levels in the cells before and after exposure to the test compound demonstrated that treatment of the cells with PMA resulted in an upregulation of ARTS-1 protein expression. It is contemplated that compounds that can upregulate ARTS-1 protein levels are therapeutically advantageous, as such compounds can suppress a proinflammatory immune response by enhancing receptor ectodomain shedding. However, an understanding of the mechanism(s) is not required in order to use the present invention. As indicated herein, PMA is a candidate for further development as a therapeutic agent.

In an alternative preferred embodiment, cultured human NCI-H292 pulmonary mucoepidermoid carcinoma cells are used in the screening. However, it is not intended that the invention be limited to the use of only this cell type, as other cell types are equally suitable, and are known to those in the art. Similarly, it is not intended that the reagents, methods or apparatus for protein collection and Western immunoblot analysis be limited to those described herein, as numerous suitable equivalents are known to those in the art.

B. Method for Drug Screening to Identify Compounds Having the Ability to Enhance Receptor Ectodomain Shedding The present invention provides screening methods to identify compounds which can regulate receptor ectodomain shedding. Test compounds which are able to regulate ectodomain shedding are identified as candidates for further development as therapeutic agents. It is contemplated that compounds which can upregulate or downregulate ectodomain shedding also have the ability to downregulate or upregulate a proinflanunatory immune response, respectively.

In one embodiment of the present invention, the screening method uses an ELISA to assess the levels of sTNFR1 in the supernatant of cell cultures. In the experiments described herein, an ELISA was used to assess the levels of sTNFR1 in the supernatants from human NCI-H292 pulmonary mucoepidermoid carcinoma cells following exposure of the culture to PMA. In this embodiment, the cultured cells were exposed to the compound, and samples of supernatant were collected at 0, 2, 8 and 24 hours following the exposure. The samples were analyzed using an ELISA with an anti-sTNFR1 antibody as described in Example 11. The results of this ELISA screening are shown in FIG. 14, Panel B. As can be seen in the Figure, treatment of the cultured cells resulted in an increase in sTNFR1 shedding over the course of 24 hours compared to a control culture (n=5,*P<0.05). Thus, this screening method identified a compound as a candidate for further drug development.

It is contemplated that compounds that can upregulate sTNFR1 ectodomain shedding are therapeutically advantageous, as such compounds can suppress a proinflammatory immune response. However, an understanding of the mechanism(s) is not required in order to use the invention. Based on the criteria set forth and described herein, PMA is a candidate for further development as a therapeutic agent.

It is not intended that the method for drug screening assessing sTNFR1 ectodomain shedding be limited to analysis of sTNFR1 shedding. It is contemplated that the analysis of ectodomain shedding other cytokine receptors, such as type II interleukin-1 cytokine receptor and interleukin-6 cytokine receptor alpha-chain gp80 also find use with the present invention.

C. Method for Drug Screening to Identify Compounds Having the Ability to Regulate the Peptidase Activity of ARTS-1 Protein The present invention provides screening methods to identify compounds which can regulate the peptidase activity of ARTS-1 protein. Test compounds which are able to regulate ARTS-1 peptidase activity are candidates for further development as therapeutic agents. It is contemplated that compounds which can upregulate or downregulate ARTS-1 peptidase activity also have the ability to downregulate or upregulate a proinflammatory immune response, respectively.

In one embodiment of the present invention, the screening method uses amino acid p-nitroanilide substrates to assess the aminopeptidase activity (described in Example 7) of purified recombinant GST-ARTS-1 fusion protein (described in Example 6). In this screening method, the amino acid p-nitroanilide hydrolysis reaction is conducted in the absence and presence of a test compound, according to the reaction conditions provided in Example 7, and the rate of amide bond hydrolysis by ARTS-1 is determined. It is then observed whether a test compound has the ability to regulate the rate of amide bond hydrolysis.

It is contemplated that compounds that can regulate ARTS-1 amide bond hydrolysis are therapeutically advantageous, as such compounds can regulate a proinflammatory immune response, and are targets for further development as therapeutic agents. However, an understanding of the mechanism(s) is not required in order to use the present invention.

It is not intended that this method for drug screening be limited to those reagents itemized in Example 7. For example, it is contemplated that purified ARTS-1 proteins in addition to ARTS-1-GST also find use with the present invention. Furthermore, it is contemplated that more than one amino acid p-nitroanilide substrate finds use with the screening method, as isoleucine p-nitroanilide, phenylalanine p-nitroanilide and glycine p-nitroanilide substrates can all be used in the hydrolysis reaction.

Experimental

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); Accurate Chemical and Scientific Corporation (Accurate Chemical and Scientific Corporation, Westbury, N.Y.); Advanced Biotechnologies (Advanced Biotechnologies Incorporated, Columbia, Md.); Amersham/Pharmacia (Amersham/Pharmacia Biotech, Piscataway, N.J.); ATCC (American Type Culture Collection, Rockville, Md.); Bachem (Bachem, King of Prussia, Pa.); Biofluids (Biofluids, Inc, Rockville, Md.); Boehringer Mannheim (Roche/Boehringer Mannheim Corporation, Indianapolis, Ind.); Calbiochem (Calbiochem-Novabiochem Corp, San Diego, Calif.); Clontech (Clontech Laboratories, Inc., Palo Alto, Calif.); Genzyme (Genzyme Corporation, Cambridge, Mass.); Life Technologies (Life Technologies/Gibco/BRL, Gaithersburg, Md.); Novex (Novex/Invitrogen, Carlsbad, Calif.); Pierce (Pierce, Rockford, Ill.); Promega (Promega Corporation, Madison, Wis.); R & D Systems (R & D Systems, Minneapolis, Minn.); Research Genetics (Research Genetics, Huntsville, Ala.); Roche (Roche/Boehringer Mannheim Corporation, Indianapolis, Ind.); Sigma (Sigma Chemical Co., St. Louis, Mo.); Stratagene (Stratagene, La Jolla, Calif.).

The following Examples are provided in order to demonstrate and further illustrate certain preferred embodiments and aspects of the present invention and are not to be construed as limiting the scope thereof.

EXAMPLE 1

Identification of ARTS-1, a Novel Human Aminopeptidase Regulator of Type1 Tumor Necrosis Factor Receptor (TNFR1) Shedding A) Yeast Two-Hybrid Library Screening A yeast two-hybrid library screening was conducted to identify proteins that interact with or are capable of interacting with the extracellular domain of the type I, 55 kDa TNF receptor (TNFR1). A human lung cDNA library (Clontech), cloned into pGAD10 (GAL4 DNA-activation domain vector), was screened to detect interactions with a GAL4BD-TNFR1 fusion protein using a Matchmaker System 2 (Clontech) using methods known in the art as well as the manufacturer's recommended protocols. Amino acids 26 to 216 of TNFR1, corresponding to the extracellular domain (i.e., the ectodomain) located between the putative leader domain and the transmembrane domain (Nophar et al., *EMBO J.*, 10:3269–3278 [1990]) were cloned into pAS2-1 (GAL4 DNA-binding domain vector) to generate the bait GAL4 DNA-binding domain fusion protein, GAL4BD-TNFR1. The Y190 yeast strain was transformed with the pAS2-1 GAL4BD-TNFR1 bait plasmid by the lithium acetate method utilizing the Yeastmaker Transformation System (Clontech). Transformed yeast were selected on synthetic drop-plates deficient in tryptophan, leucine and histidine in the presence of 25 mM 3 amino-1,2,4-triazole (SIGMA). His$^+$ colonies were then subjected to β-galactosidase colony-lift filter assays and β-galactosidase producing colonies were selected and restreaked on synthetic drop-out plates. Approximately 7.11×10$^6$ transformants were screened. β-galactosidase positive colonies which produced a blue signal within 2 hours were selected for further study. Selected colonies were analyzed for expression of the GAL4 binding domain (GAL4BD) fusion protein by immunoblotting using an anti-GAL4BD monoclonal antibody (Clontech). Thirty three positive clones were identified which activated the β-galactosidase reporter construct. All 33 positive clones were sequenced using an ABI Perkin Elmer 377 automated fluorescent sequencer.

One positive clone, L26C-53A, encoding a consensus zinc metalloprotease catalytic motif was selected for further study. This clone contained a 2355-bp insert containing an open reading frame of 631 amino acids, but did not contain a poly(A) tail or a putative translation initiation site. The gene encoded by this insert was entitled aminopeptidase regulator of type-1, 55 kDa tumor necrosis factor receptor shedding (or ARTS-1). The L26C-53A sequence corresponds to ARTS-1 bases 1044 to 3082.

B) ARTS-1 cDNA Cloning/Phage Plaque Hybridization

Using $^{32}$P-labelled DNA derived from clone L26C-53A as a probe, a PMA-stimulated NCI-H292 cell line cDNA library (Stratagene) was screened to obtain ARTS-1 cDNA clones. The NCI-H292 cell line was derived from human pulmonary mucoepidermoid carcinoma cells and has been demonstrated to shed cell surface sTNFR1 in response to PMA stimulation (Levine et al., *Am. J. Respir. Cell Mol. Biol.*, 14:254–261 [1996]). The uni-ZAP XR phage cDNA library (Stratagene) was constructed with NCI-H292 cell poly (A$^+$) mRNA isolated following 24 hours of stimulation with 1 μM PMA (phorbol 12-myristate, 13-acetate, Sigma).

Bacteriophage from the uni-ZAP library were plated in a lawn of XL1-Blue (MRF-) *E. coli* (Stratagene) at a density of 50,000 pfu per 150 mm plate and incubated overnight at 37° C. Plaques were transferred to Hybond N+ filters (Amersham/Pharmacia) and denatured for 5 minutes in 1.5M sodium chloride, 0.5 M sodium hydroxide. Filters were then neutralized in two washes of 5 minutes each in 1.5M sodium chloride, 1M Tris-base, rinsed in 3×SSC and UW cross-linked. Filters were pre-hybridized in 10×Denhardt's solution, 6×SSPE, 1% SDS at 42° C. for 4 hours in hybridization buffer. Filters were hybridized overnight at 42° C. with approximately 10$^7$ CPM of $^{32}$P-labelled L26C-53A insert which was generated by random priming. Filters were then washed in 2×SSC, 0.5% SDS for 20 minutes at room temperature, followed by two 1 hour washes in 1×SSC, 0.1% SDS at 65° C. Filters were then exposed to x-ray film overnight and positive plaques were selected. Positive plaques were subjected to two additional rounds of plaque hybridization prior to sequencing. Positive plaques were recovered via in vivo excision utilizing the ExAssist helper phage (Stratagene).

Following 3 rounds of screening, four hybridizing phage clones were identified, then sequenced utilizing the ThermoSequenase cycle sequencing kit (Amersham/Pharmacia). These four hybridizing clones overlapped the L26C-53A sequence, but none encoded a full-length cDNA. Sequencing revealed one phage clone (bp 1–1777) which contained the putative 5' UTR and three phage clones which contained the putative 3' UTR and the poly(A) tail (bp 2181–4845). cDNA sequence encoding the portion of the gene lying between these 5' and 3' terminal clones was obtained via PCR from Marathon-Ready™ human lung cDNA (Clontech) utilizing Pfu Turbo DNA Polymerase (Stratagene) and the following primers:

```
                                          (SEQ ID NO:3)
    5'-ATAACCATCACAGTGAGGGGAGG-3'  (1684–2279) and (SEQ ID NO:4)
    5'-TAGTTGACTCCGCAGCATTCGCTC-3'  (2257–2280)
```

The cDNA segment amplified with these primers was cloned into pGemTEasy (Promega) and both strands were sequenced by automated fluorescent sequencing using an ABI Perkin Elmer 377 automated fluorescent sequencer.

Sequences of all overlapping regions from the original two-hybrid clone L26C-53A (bp 1044 to 3082), the four NCI-H292 cDNA library clones and the PCR product (bp 1684 to 2280) showed no discrepancies in the nucleotide sequence in their overlapping regions.

EXAMPLE 2

Molecular Analysis of the ARTS-1 cDNA and Predicted Polypeptide

The complete cDNA corresponding to the human ARTS-1 transcription unit contains 4845 nucleotides and encodes an open reading frame of 2823 bp, as shown in FIG. 1 and set forth in SEQ ID NO:1. The first in-frame ATG codon, located at nucleotide 88, follows an in-frame stop codon, located at nucleotide 76, and matches the −3 and +4 nucleotides of the consensus Kozak sequence consistent with a strong initiator codon (aagatgg) (Kozak, J. Cell Biol., 108: 229–241 [1989]). Sequence analysis revealed five potential N-glycosylation sites and a TAA stop codon, located at nucleotide 2911. The putative 3' untranslated region contained a consensus polyadenylation site (AATAAA), located at nucleotides 4876 to 4800, which is 18 nucleotides upstream of a 27 nucleotide poly(A) tail. The 3' untranslated region also included two ATTTA sites, located at nucleotides 3929 and 4457; this sites have been identified as an mRNA destabilization motif in mRNA's for cytokines, oncogenes and transcriptional activating factors (Stephens et al., J. Biol. Chem., 267:8336–8341 [1992]).

The open reading frame predicted from the human ARTS-1 cDNA encodes a protein of 941 amino acid residues (See, FIG. 1 and SEQ ID NO:2) with a calculated molecular weight of 107,227 Da and an estimated pI of 6.0. Sequence analysis, including Kyte-Doolittle hydropathy prediction (Kyte and Doolittle, J. Mol. Biol., 157:105–132 [1982]) was performed using MacVector 7.0 software (Oxford Molecular). The location of the putative hydrophobic transmembrane α-helical domain was predicted utilizing several web-based analysis programs (MEMSAT2 (McGuffin et al., Bioinform., 16:404–405 [2000]; Sosui (Hirokawa et al., Bioinform., 14:378–379 [1998]; TMAP (Persson and Argos, J. Mol. Biol., 237:182–192 [1994]); TMpred (Hofmann and Stoffel, Biol. Chem. Hoppe-Seyler 374:166 [1993]; and TopPred2 (von Heijne, J. Mol. Biol., 225:487–494 [1992]). In sum, ARTS-1 is predicted to be a type II integral membrane protein with a single hydrophobic transmembrane α-helical domain, located between amino acids 5 and 28 (See, FIGS. 1 and 3), and a very short hydrophobic intracellular amino-terminal domain (See, McGuffin et al., Bioinform., 16:404–405 [2000]; Hirokawa et al., Bioinform., 14:378–379 [1998]; Persson and Argos, J. Mol. Biol., 237: 182–192 [1994]); Hofmann and Stoffel, Biol. Chem. Hoppe-Seyler 374:166 [1993]; and von Heijne, J. Mol. Biol., 225:487–494 [1992]).

The protein sequence analysis using MacVector software revealed a zinc metalloprotease consensus catalytic motif (HEXXH(Y)$_{18}$E) (SEQ ID NO:10), which is predictive of an active metalloprotease (Hooper, Zinc Metalloproteases in Health and Disease, Taylor & Francis, London, England [1996], p. 1–21). Utilizing various web-based analysis programs, a putative amino acid transmembrane domain (as predicted by von Heijne, J. Mol. Biol., 20:487–494 [1992]), extending from amino acids 5 to 28, was identified. These features suggest that human ARTS-1 is a type II integral membrane protein with a single hydrophobic transmembrane α-helical domain, located between amino acids 5 and 28 (See, FIGS. 1 and 2), and a very short, hydrophobic intracellular amino-terminal domain (See, McGuffin et al., Bioinform., 16:404–405 [2000]; Hirokawa et al., Bioinform., 14:378–379 [1998]; Persson and Argos, J. Mol. Biol., 237: 182–192 [1994]); Hofinann and Stoffel, Biol. Chem. Hoppe-Seyler 374:166 [1993]; and von Heijne, J. Mol. Biol., 225:487–494 [1992]).

A BLAST protein homology comparison revealed that the human ARTS-1 contained significant homology with several members of the aminopeptidase family of gluzincin zinc metalloproteases (See, Tables 1 and 2, supra) (Wang and Cooper, Zinc Metalloproteases in Health and Disease, Taylor & Francis, London, England [1996]). As has previously been reported for other aminopeptidase family members, the human ARTS-1 was found to contain a 375 amino acid domain that is highly conserved with human placental leucine aminopeptidase (PLAP) (Rogi et al., J. Biol. Chem., 271:56–61 [1996]), rat insulin-regulated aminopeptidase (IRAP) (Keller et al., J. Biol. Chem., 270:23612–23618 [1995]), human aminopeptidase A (AMP A) (Nanus et al., Proc. Natl. Acad. Sci. USA 90:7069–7073 [1993]; Li et al., Genomics 17:657–664 [1993]), human aminopeptidase N (AMP N) (Olsen et al., FEBS Lett., 238:307–314 [1988]), human puromycin sensitive aminopeptidase (PSA) (Tobler et al., J. Neurochem., 68:889–897 [1997]), rat thyrotropin-releasing hormone degrading enzyme (TRH DE) (Schauder et al., Proc. Natl. Acad. Sci. USA 91:9534–9538 [1994]), Saccharomyces cerevisiae aminopeptidase YSCII (Garcia-Alvarez et al., Eur. J. Biochem., 202:993–1002 [1991]), C. elegans cosmid F49E8.3 gene product (Wilson et al., Nature 368:32–38 [1994]), and Lactococcus lactis aminopeptidase N (Tan et al., FEBS Lett., 306:9–16 [1992]). This highly conserved domain contains the putative consensus zinc binding domain and catalytic site ($T^{350}$VAHELAHQWFG (SEQ ID NO:8) and $L^{372}$WLNEGFA (SEQ ID NO:9) which is characteristic of aminopeptidase family members (Wang and Cooper, Zinc Metalloproteases in Health and Disease, Taylor & Francis, London, England [1996]; Keller et al., J. Biol. Chem., 270:23612–23618 [1995]). Furthermore, PLAP, AMP A, AMP N, IRAP and TRH DE share structural similarity with human ARTS-1, based upon the presence of a transmembrane domain and a short intracytoplasmic tail, consistent with a type II integral membrane protein.

EXAMPLE 3

ARTS-1 mRNA Expression Analysis

Following analysis of the ARTS-1 cDNA, the expression pattern of endogenous of ARTS-1 mRNA was investigated using a Northern immunoblotting protocol. RT-PCR was performed on human lung poly(A$^+$) mRNA (Clontech) to generate the human ARTS-1 cDNA coding sequence utilizing the following primers:

(SEQ ID NO:5)
5'-GCAAGAAGATGGTGTTTCTGCCCCTC-3' (80–105) and (SEQ ID NO:6)
5'-TTACATACGTTCAAGCTTTTCACT-3' (2890–2913).

The full length ARTS-1 coding sequence amplified by these primers was cloned into the pTarget mammalian expression vector (Promega). The DNA sequence of this cloned open reading frame was obtained from both strands by automated fluorescent sequencing, as known in the art. There were no discrepancies between the sequence obtained from these two strands, nor from the sequence obtained from the PMA-stimulated NCI-H292 cell line cDNA library. A $^{32}$P-labelled cDNA probe, corresponding to the full length ARTS-1 coding sequence, was utilized as a probe for Northern blotting of human multiple tissue Northern blots (Clontech) according to the manufacturer's protocol.

As shown in FIG. 3, Northern blot analysis utilizing poly(A+) mRNA from multiple human tissues revealed that the human ARTS-1 transcript was expressed in multiple tissues, including spleen, thymus, small and large intestine, peripheral blood leukocyte, heart, placenta, lung, skeletal muscle, kidney and pancreas. In these tissues, an approximately 5.7 kB predominant mRNA species was detected (See, FIG. 3, top panel). Also shown is the same blot following stripping and rehybridization to a probe specific for the human GAPDH transcript as a reference for RNA loading normalization (See, FIG. 3, bottom panel).

EXAMPLE 4

The Generation of Polyclonal Anti-ARTS-1 Antiserum

In order to conduct studies of the ARTS-1 polypeptide, polyclonal antiserum was generated against the ARTS-1 polypeptide. Specifically, a 17 amino acid ARTS-1 synthetic peptide was used to immunogenize New Zealand white rabbits and subsequently collect immune serum using a commercial service (Research Genetics). This peptide corresponded to amino acids 538 to 554 of the ARTS-1 protein and had the sequence:

R$^{538}$GRNVHMKQEHYMKGSD$^{554}$ (SEQ ID NO:7)

This particular peptide was chosen based upon its antigenic potential and its lack of homology with other protein sequences via BLAST homology search.

Rabbits were immunized with this peptide using standard techniques. The ARTS-1 peptide was conjugated to KLH and mixed with an equal volume of Freund's complete adjuvant. The amount of antigen utilized per immunization was 0.1 mg, which was injected into three subcutaneous dorsal sites. The animals received boosts at weeks 2, 6, and 8. Bleeds were obtained at weeks 4, 8 and 10 and tested for the presence of anti-ARTS-1 antibody. In subsequent experiments, the antiserum obtained from the 10 week bleed was used.

EXAMPLE 5

Analysis of ARTS-1 Polypeptide Expression in Cultured Cell Lines and Primary Cells Following the production of ARTS-1 polyclonal antiserum, the expression of endogenous ARTS-1 polypeptide in cultured cell lines and primary cells was investigated using standard Western immunoblotting as known in the art. Protein concentrations were determined via the BCA protein assay (Pierce). Following protein quantitation, 20 microgram samples of protein were boiled for 5 minutes in Laemmli buffer. Samples were then resolved via SDS-PAGE (6% polyacrylamide) and electroblotted onto nitrocellulose (Novex). Blots were incubated overnight in blocking buffer (5% wt/vol nonfat dry milk in PBS/0.1% Tween-20), then incubated for 2 hours with ARTS-1 antiserum at a 1:20,000 dilution in blocking buffer. Membranes were washed three times for 5 minutes each wash in PBS/0.1% Tween; incubated for 2 hours with 0.8 mg/ml horseradish peroxidase conjugated goat anti-rabbit IgG (Life Technologies) diluted to 1:5,000 in blocking buffer, then washed three times for 5 minutes each wash in PBS/0.1% Tween and finally washed three times for 5 minutes each wash in PBS/0.3% Tween. Membranes were then incubated in chemiluminescent detection substrate for 1 minute and signal detected on X-ray film.

Crude homogenates made from NCI-H292 cells for immunoblot analysis were produced by cell lysis in homogenization buffer consisting of 200 μl of 50 mM Tris-HCl, pH 7.2, containing 0.1% Triton X-100 and Complete™ protease inhibitor cocktail tablet (Boehringer Mannheim) and sonicated for four times at 15 seconds each using a microprobe. The homogenate was centrifuged at 1,000×g for 5 minutes to remove nuclei, unbroken cells and debris. The low speed supernatant was either utilized as a whole cell lysate or was further fractionated by ultracentrifugation at 100,000×g for 1 hour to generate a crude cytosolic and membrane fractions. The crude membrane fraction was resolubilized in homogenization buffer prior to immunoblotting.

Specificity of the resulting polyclonal antiserum was first tested using crude whole cell homogenates, and membrane and cytosolic fractions prepared from cultured NCI-H292 cells. These results are shown in FIG. 4. Comparing the top two panels of FIG. 4, the antiserum was shown to detect a predominant 100 kDa membrane form and a predominant 68 kDa cytosolic form from the NCI-H292 cells. The whole cell extracts revealed a mixture of these two forms. The preimmune serum showed no reactivity towards the same samples when used at the same concentration.

Specificity of the immune serum was further demonstrated in competition experiments as shown in the bottom two panels of FIG. 4. In these competition experiments, 1 μl of the ARTS-1 antiserum was pre-incubated with 1 mg of either bovine serum albumin or RGRNVHMKQE-HYMKGSD peptide (SEQ ID NO:7) for two hours prior to utilization for immunoblotting. Preincubation of the immune serum with the peptide against which the polyclonal antiserum was raised resulted in almost complete attenuation of the immune signal (Bottom panel). In contrast, preincubation of the immune serum with bovine serum albumin resulted in minimal attenuation of immune signal (Third panel).

The expression of endogenous ARTS-1 polypeptide in primary cells and other cell lines was further investigated using the anti-ARTS-1 antiserum and Western immunoblot technique, as shown in FIG. 5. These experiments analyzed membrane and cytosolic fractions made from human bronchial brushing specimens, the airway epithelial cell lines BEAS-2B and BET-1A, human lung carcinoma cell line A549, cultured NCI-H292 cells, primary cultures of normal human bronchial epithelial cells (NHBE), human umbilical vein endothelial cells (HUVEC) and human fibroblasts. These experiments also revealed multiple sized forms of ARTS-1 polypeptide on the Western immunoblot, including 132, 100 and 68 kDa forms which may localize to various subcellular fractions. These multiple sized forms may be due to regulated processing of the ARTS-1 polypeptide, and furthermore may indicate that this processing is compartmentalized.

EXAMPLE 6

Expression and Purification of Recombinant GST-ARTS-1 Polypeptide

The cDNA sequence of the ARTS-1 extracellular domain (i.e., the ectodomain; amino acids 30–941) was PCR amplified from the pTarget plasmid containing the full length ARTS-1 coding sequence. The ARTS-1 extracellular domain was then cloned into the pGEX-6P-1 plasmid (Amersham/Pharmacia) and used to transform the BL21 *E. coli* host strain. Colonies expressing GST-ARTS-1 fusion protein were selected by Western blotting utilizing an anti-GST antibody (Amersham/Pharmacia). Positive clones were grown at room temperature, stimulated for 4 hours with 0.6 mM isopropyl β-D-thiogalactoside (IPTG) and subsequently lysed with B-PER protein extraction reagent (Pierce). Cells were centrifuged at 27,000×g for 15 minutes to separate the soluble from the insoluble fractions. Following treatment with 0.2 mg/ml lysozyme for 5 minutes, the GST-ARTS-1 fusion protein was isolated from the insoluble fraction by denaturation with 6M urea in PBS. The GST-ARTS-1 fusion protein was refolded by serial dialysis against PBS baths containing decreasing urea concentrations (5 M to 0 M). The GST-ARTS-1 fusion protein was purified utilizing a glutathione sepharose 4B affinity column and eluted with reduced glutathione buffer using techniques known in the art.

To assess the purity of the eluted recombinant GST-ARTS-1 fusion protein, samples were subjected to SDS-PAGE on a 4%–12% gradient gel (Novex) and stained with Coomassie brilliant blue. FIG. 6A shows the result of this experiment. In this Figure, soluble and insoluble protein fractions from BL21 *E. coli* transformed with empty pGEX-6P-1 vector (lanes 1 and 2) or the pGEX-6P-1-ARTS-1 vector (lanes 3 and 4) are shown. The GST-ARTS-1 fusion protein following elution is shown in lane 5 as a predominant 132 kDa band, corresponding to the predicted molecular weight of a GST-ARTS-1 fusion protein (104 kDa ARTS-1 extracellular domain plus 26 kDa GST tag). The control purified GST tag is revealed as a predicted 26 kDa band in lane 6.

Purified recombinant GST-ARTS-1 fusion protein samples were further subjected to FPLC analysis (LKB LCC-500 plus, Amersham/Pharmacia) utilizing a Superose 6 HR 10/30 gel filtration column (Amersham/Pharmacia). Recombinant purified GST-ARTS-1 fusion protein samples were eluted with PBS at a flow rate of 0.5 ml/min and fractions were collected every 1 minute. Absorbance was recorded at 280 mn with a chart speed of 0.25 cm/min. FIG. 6B shows the result of this analysis. In this figure, FPLC analysis of the purified GST-ARTS-1 revealed a single major protein elution peak which eluted at approximately 40 minutes.

Using the aminopeptidase activity assay described below, FPLC fractions were assessed for aminopeptidase activity utilizing a phenylalanine p-nitroaniline substrate. As shown in FIG. 6C, the single major protein peak revealed by FPLC analysis coeluted with a peak of aminopeptidase activity against a phenylalanine p-nitroaniline substrate in pooled fractions from 38–44 minutes.

EXAMPLE 7

ARTS-1 Aminopeptidase Activity Assay

Aminopeptidase activity of the recombinant GST-ARTS-1 fusion protein was assessed by determination of the rate of amide bond hydrolysis of amino acid p-nitroanilide substrates (Bachem). Amino acid p-nitroanilides (final concentrations 0.25 to 8 mM) were incubated at room temperature with 24 pmoles of GST-ARTS-1 fusion protein in 200 μl of 50 mM Tris, pH 7.5 for 1 hour. Reactions were terminated by addition of 280 μl of 3M sodium acetate (pH 5.2). The rate of amide bond hydrolysis was determined by measuring the absorbance of p-nitroaniline at 380 nm (See, Table 3, supra). Spontaneous hydrolysis of the substrate was corrected for by subtracting the absorbance of control incubations which were terminated immediately. Kinetic constants were determined by Lineweaver-Burk analysis. Each experimental point was assayed in triplicate and each determination utilized six concentrations of each amino acid p-nitroanilide substrate. Correlation coefficients for each line generated were greater than 0.997.

As shown in Table 3, recombinant GST-ARTS-1 protein possessed selective aminopeptidase activity against non-polar amino acid substrates with a four-fold range of enzyme activity. Isoleucine-pNA was found to be the most favorable amino acid substrate based upon $k_{cat}/K_m$ determination, followed by Phe>Gly>Cys>Leu>Met>Ala>Pro>Val. Recombinant GST-ARTS-1 had no activity against either acidic (Asp or Glu) or basic (Arg, His, or Lys) amino acid substrates.

EXAMPLE 8

ARTS-1 Endopeptidase Activity Assay

The endopeptidase activity of recombinant GST-ARTS-1 fusion protein was also assessed. In this assay, 5 μg of recombinant GST-ARTS-1 fusion protein was incubated with 10 μg of either bovine serum albumin, human albumin, rabbit myosin heavy chain or transferrin overnight. Sample were then subjected to SDS-PAGE utilizing 4 to 12% gradient gels (Novex) and stained with Coomassie brilliant blue. In this assay, recombinant GST-ARTS-1 was shown to have no demonstrable endopeptidase activity against bovine serum albumin, human albumin, rabbit myosin heavy chain or human transferrin.

EXAMPLE 9

Construction of Stably Transfected Cell Lines Expressing Sense and Antisense ARTS-1 cDNA's In light of the ability of the ARTS-1 polypeptide to bind to the TNFR1 ectodomain in the yeast two-hybrid interaction assay, the following experiment was conducted in order to determine whether ARTS-1 has the ability promote the cleavage and shedding of the TNFR1 ectodomain from the surface of human cells in culture. This experiment was done in two phases. The first phase involved construction of stably transfected cell lines which expressed either reduced or elevated levels of ARTS-1 polypeptide. The NCI-H292 cell line was stably transfected with one of three constructs, all based on the pTarget vector (Promega). Transfection was by the Fugene system (Roche). The pTarget vector expresses a gene product (encoded by the neo gene) which imparts resistance to the antibiotic G-418, which kills both prokaryotic and eukaryotic cells. The construct also contains a constitutively active CMV promoter which will express cloned DNA inserts in mammalian cells. The pTarget vectors used to transfect the NCI-H292 cells were:

1) an empty pTarget vector,
2) pTarget vector containing the full length ARTS-1 cDNA coding region in the sense orientation,
3) pTarget vector containing ARTS-1 cDNA bases 61 to 213 in the anti-sense orientation. This region overlaps the putative transcription start site and intracellular and transmembrane domains. Following the transfection of these constructs into the host cells, the transfectants were cultured under selective pressure in RPMI-1640 media supplemented with 10% heat-inactivated fetal calf serum and 1× antibiotic-antimycotic (Biofluids) and 500 µg/ml of the G-418 (Promega). Two independent clones of stable transfectants containing either sense or anti-sense ARTS-1 plasmid were then generated via limiting dilutions. Both sense and anti-sense clones were screened by immunoblotting (described above) utilizing anti-ARTS-1 polyclonal serum to select duplicate clones for subsequent analysis.

Cell lines were then selected based upon enhanced or suppressed ARTS-1 protein expression as determined by the immunoblotting of cell membrane fractions, as shown in FIG. 7. Integration of the empty pTarget vector (indicated "Mock") had little effect on endogenous ARTS-1 expression compared to cells that do not contain any stably integrated plasmid (WT). The two cell lines expressing the full length ARTS-1 cDNA in the sense orientation (ARTS-1) showed a significant increase in ARTS-1 protein expression, while the two cell lines expressing ARTS-1 antisense sequence (AS) showed significant reduction in ARTS-1 protein expression. These stably integrated cell lines were examined for sTNFR1 shedding activity (See, Example 11, below).

EXAMPLE 10

Construction of Stably Transfected Cell Lines Expressing Mutant ARTS-1 cDNA's

The predicted ARTS-1 polypeptide contains a peptidase/protease consensus motif found in the aminopeptidase family of gluzincin zinc metalloproteases. It was determined if this peptidase/protease catalytic motif was necessary for the ability of ARTS-1 to promote shedding of the TNFR1 ectodomain. To conduct this experiment, a series of ARTS-1 mutants were constructed which contain point mutations predicted to abolish the ARTS-1 peptidase/protease activity (Devault et al., *FEBS Lett.*, 23154–23158 [1988]; Devault et al., *J. Biol. Chem.*, 263:4033–4040 [1988]; Vallee and Auld, *FEBS Lett.*, 257:138–140 [1989]; Vallee and Auld, *Biochemistry* 29:5647–5659 [1990]; Wang and Cooper, *Proc. Natl. Acad. Sci. USA* 90:1222–1226 [1993]). These mutations lie within the zinc metalloprotease family zinc-binding/catalytic domain consensus HEXXH$(Y)_{18}$E (SEQ ID NO:10; consisting of a zinc binding and catalytic site domains). In the ARTS-1 polypeptide, this motif is located at $H^{333}$ELAH$(Y)_{18}E^{376}$ (SEQ ID NO:11). The mutations made were H353P, E354V, H353P and E354V in combination, and H357V. Mutagenesis of the ARTS-1 gene open reading frame was performed using a QuikChange Site-Directed Mutagenesis Kit (Stratagene) according to the manufacturer's instructions.

The NCI-H292 cell line was stably transfected with one of six constructs, all based on the pTarget expression vector. The method used to produce stably transfected cell lines containing these constructs is the same as that provided in Example 9. These constructs (and resulting cell lines) were:

1) an empty pTarget vector, 2) the ARTS-1 cDNA (WT) coding region, 3) the ARTS-1 cDNA encoding a H353P mutation, 4) the ARTS-1 cDNA encoding a E354V mutation, 5) the ARTS-1 cDNA encoding a H353P and E354V double mutation, and 6) the ARTS-1 cDNA encoding a H357V mutation.

EXAMPLE 11

TNFR1 Ectodomain Shedding Assay

The amount of TNFR1 ectodomain shedding occurring in each of the stably transfected cell lines described in Example 9 was assessed. The levels of sTNFR1 ectodomain in cell culture supernatants from these cell lines were assayed by a commercially available sandwich-enzyme-linked immunosorbent assay (ELISA) technique (R & D Systems) with a lower limit of detection of 7.8 pg/ml. The protocol used was according to the manufacturer's instructions. The results of this assay are depicted in FIG. 8 as the mean of 5 independent experiments, with accompanying SEM (standard error of the mean) indicated above the bar. As can be seen in FIG. 8, the cell lines with increased ARTS-1 protein expression also showed a significant increase in the amount of sTNFR1 present in cell culture supernatants as compared to cells transfected with the empty pTarget vector (Mock) or non-transfected (WT) controls. This change in sTNFR1 concentration represents an approximately 200% increase in sTNFR1 shedding resulting from overexpression of the ARTS-1 protein.

Conversely, cell lines showing decreased ARTS-1 protein expression showed significantly decreased levels of sTNFR1 in cell culture supernatants as compared to cells transfected with the empty pTarget vector, as shown in FIG. 8. This change in concentration represents an approximately 80% decrease in sTNFR1 shedding resulting from expression of an ARTS-1 anti-sense transcript encompassing the putative translation start site.

A similar experiment analyzing the ability of ARTS-1 overexpression to potentiate the cleavage and shedding of TNFR ectodomain from the surface of NCI-H292 cells in response to PMA stimulation using these same cell lines is shown in FIG. 9. Cell lines overexpressing full length ARTS-1 mRNA were stimulated with 0.1 µM phorbol 12-myristate 13-acetate (PMA), which has previously been shown to upregulate sTNFR1 shedding in NCI-H292 cells (Levine et al., *Am. J. Respir. Cell Mol. Biol.*, 14:254–261 [1996]). As shown in FIG. 9, the cell line containing only the empty pTarget vector showed only a modest increase in sTNFR1 shedding following 24 hours of PMA treatment, increasing from approximately 300 pg/ml to 415.3±4.5 pg/ml. However, the cell line overexpressing the ARTS-1 cDNA showed a more dramatic increase in sTNFR1 shedding following 24 hours of PMA treatment, increasing from 485±16.9 pg/ml to 914.2±9.5 pg/ml This assay was further used to measure the sTNFR1 ectodomain shedding activity of ARTS-1 peptidase/protease catalytic mutants. The construction of these mutations (and resulting mutant cell lines) are described in Example 10. The ability of theses mutants to regulate sTNFR1 shedding was ascertained by measuring the concentration of sTNFR1 in the cell culture supernatant as described above in this Example. These results are depicted in FIG. 10 as the mean of five independent experiments, with accompanying SEM (standard error of the mean).

As shown in FIG. 10, the cell line overexpressing the ARTS-1 cDNA (ARTS-1) showed a significantly elevated level of sTNFR1 in the culture supernatant compared to control cell lines containing no integrated DNA (WT) or containing the empty pTarget vector (MOCK). Unexpectedly, each of the cell lines containing mutant forms of the ARTS-1 polypeptide showed elevated levels of sTNFR1 compared to the control lines (i.e., WT and MOCK). This experiment demonstrates the unexpected property where the peptidase/protease activity of the ARTS-1 polypeptide is not required for the sTNFR1 shedding regulatory activity of ARTS-1 polypeptide.

Although not described here, IL-1 and IL-6 receptor ectodomain shedding can also be measured by ELISA-based assays using commercially available kits that measure soluble forms of the IL-1 and IL-6 receptors (R & D Systems, Catalog numbers DR1B00 and DR600, respectively). These ELISA-based assays measure the concentration of sIL-1RII and sIL-6R, both with a lower limit of detection of 31 pg/ml.

EXAMPLE 12

Effect of ARTS-1 Expression on Membrane-Associated TNFR1

The degree of TNFR1 ectodomain shedding as a function of ARTS-1 protein expression was also indirectly assessed by determining the relative amounts of membrane-bound TNFR1 fragment in each of the stably transfected cell lines described in Example 9 using Western immunoblotting.

Crude membrane fractions from the stably transfected NCI-H292 cells described in Example 9 were prepared and protein concentrations were quantitated, as described above. Samples from these membrane-derived protein preparations were resolved by SDS-PAGE and analyzed by Western immunoblotting as described above in Example 5 using a murine anti-human TNFR1 monoclonal primary antibody which detected the membrane fragment of the receptor (R & D System). This Western blot is shown in FIG. 11. Two independent strains of each cell line were analyzed in parallel.

As shown in FIG. 11, cell lines over-expressing ARTS-1 (ARTS-1) demonstrated a decrease in membrane-associated TNFR1 relative to non-transfected (WT) or control transfected (Mock) cell lines, consistent with an increase in constitutive TNFR1 ectodomain shedding. Conversely, cell lines expressing anti-sense ARTS-1 mRNA (AS) demonstrated an increase in membrane-associated TNFR1 relative to non-transfected (WT) or control transfected (Mock) cell lines, consistent with a reduction in constitutive TNFR1 ectodomain shedding.

EXAMPLE 13

ARTS-1/TNFR1 in vivo Co-Immunoprecipitation Assays

The ability of ARTS-1 to directly interact with TNFR1 ectodomain was assessed in vivo using a co-immunoprecipitation assay. This assay utilized anti-ARTS-1 antiserum and monoclonal anti-TNFR1 antibodies. The immunoprecipitated proteins were visualized by Western immunoblotting.

Crude membrane fractions from cultured NCI-H292 cells were prepared and protein concentrations were quantitated as described above. From these membrane-derived protein preparations, 200 μg samples were incubated with 20 μg of murine anti-human TNFR1 monoclonal antibody (R & D System) or 1 ml of anti-ARTS-1 antiserum overnight at 4° C. in immunoprecipitation buffer (50 mM Tris-HCl, 120 mM NaCl, 0.1% Triton X-100 and COMPLETE™ protease inhibitor (Roche), pH 7.2). Following the incubation, the resulting antibody complexes were immunoprecipitated by binding to 200 μl of immobilized protein A/G beads (Pierce) for 2 hours at room temperature. Proteins contained in the samples were then resolved by SDS-PAGE and analyzed by Western immunoblotting as described above.

Two different combinations of precipitation and immunoblotting antibody were used. The results of these immunoprecipitation experiments are shown in FIG. 12. In one experiment (FIG. 12, top panel), the anti-TNFR1 antibody was used in the immunoprecipitation (indicated as "IP" in the Figure), and the anti-ARTS-1 antiserum was used as the primary antibody in the immunoblotting (indicated as "IB" in the Figure). In a second experiment (FIG. 12, bottom panel), the antibodies were reversed, where the anti-ARTS-1 antiserum was used in the immunoprecipitation, while the anti-TNFR1 antibody was used as the primary antibody in the immunoblotting. Also in these experiments, anti-ARTS-1 pre-immune serum (written "PI") and a purified murine IgG1 isotype (written "IgG1") were used as negative controls.

As shown in the top panel of FIG. 12, immunoprecipitation of the NCI-H292 cell membrane proteins with an anti-TNFR1 monoclonal antibody resulted in the coprecipitation of the 100 kDa ARTS-1 species and, conversely, as seen in the bottom panel, immunoprecipitation with anti-ARTS-1 antiserum coprecipitated the 55 kDa TNFR1. These results indicate an in vivo protein-protein interaction between ARTS-1 and TNFR1 proteins.

Similar immunoprecipitation experiments were also performed using the stably-transfected NCI-H292 cell lines described in Example 9. In these experiments, the anti-TNFR1 antibody was used to immunoprecipitate protein from the various membrane protein fractions, and the resulting immunoprecipitate was examined by Western immunoblotting using anti-ARTS-1 antiserum as the primary antibody. As shown in FIG. 13, immunoprecipitation using an anti-TNFR1 monoclonal antibody of cell membrane protein derived from the anti-sense ARTS-1 cell line (AS) showed decreased amounts of ARTS-1 protein as compared to control-transfected (Mock) or non-transfected (WT) cells, consistent with decreased ARTS-1 protein expression in anti-sense ARTS-1 cells. No increase in ARTS-1 protein levels relative to control cell lines was detected following immunoprecipitation of ARTS-1 overexpressing cell lines with an anti-TNFR1 monoclonal antibody, which likely reflects increased TNFR1 shedding related to ARTS-1 overexpression.

EXAMPLE 14

Methods for Drug Screening

The present invention provides two examples of methods for drug screening. These methods identify test compounds which are able to regulate ARTS-1 protein expression in a tissue, or regulate sTNFR1 shedding in a cell culture system.

In the first method, cultured human NCI-H292 pulmonary mucoepidermoid carcinoma cells were exposed to a test compound, in this case, 4b-phorbol 12-myristate 13-acetate (PMA) at a concentration of 0.1 μM. Cells were harvested and the membrane protein fraction isolated at intervals from prior to exposure to the test compound (Time=0) to 24 hours following exposure to the compound. The protein samples were analyzed in a Western immunoblot using the anti-ARTS-1 antiserum at the primary detection antibody, as described in Examples 4 and 5. The protein fractions were analyzed in duplicate, and the relative densitometry units for each lane are shown beneath the columns. Each immunoblot is representative of 3 independent experiments. The results of this screening are shown in FIG. 14, Panel A. As can be seen in the Figure, treatment of the cultured cells resulted in an increase in ARTS-1 protein expression over the course of 24 hours. Thus, this screening method identified a compound that is a candidate for further drug development.

Results from a second screening method are illustrated in FIG. 14, Panel B. In this screening method, cultured human NCI-H292 pulmonary mucoepidermoid carcinoma cells were again exposed to a test compound, PMA, at a concentration of 0.1 μM. Culture medium supernatant was collected from the cultures at intervals between 0 and 24 hours post treatment. The samples were analyzed by the TNFR1 ectodomain shedding assay using an ELISA as described in Example 11. In this assay, anti-sTNFR1 antibody was used to quantitate the concentrations of sTNFR1 in the cell culture supernatants. The results of this ELISA screening are shown in FIG. 14, Panel B. As can be seen in this Figure, treatment of the cultured cells resulted in an increase in sTNFR1 shedding over the course of 24 hours compared to a control culture (n=5,*P) <0.05). Thus, this screening method also identified a compound that is a candidate for further drug development.

EXAMPLE 15

Tumor Necrosis Factor Bioactivity (Cytotoxicity) Assay

The bioactivity of tumor necrosis factor (TNF) is measured by a cell cytotoxicity assay utilizing the WEHI 164 clone-13 mouse fibrosarcoma cell line (ATCC, CRL 1751). This cell line has been shown to be highly sensitive to the cytotoxic effects of human tumor necrosis factor at concentrations as low as 0.1 pg/ml TNF following pretreatment with actinomycin D (Eskandari et al., Immunol. Invest., 19:69–79 [1990]). In this assay, WEHI 164 cells are seeded into 96-well microtiter plates at a density of 40,000 cells per well in RPMI-1640 supplemented with penicillin (100 units/ml) (Advanced Biotechnologies), streptomycin (100 μg/ml) (Advanced Biotechnologies), L-glutamine (2 mM) (Advanced Biotechnologies), 10% heat-inactivated fetal-calf serum (Inovar), and actinomycin-D (0.5 μg/ml) (Calbiochem). Test samples (serum, plasma or any other body fluid) to be tested for TNF activity are diluted 6-fold in RPMI-1640 culture medium (Advanced Biotechnologies), heat-inactivated at 56° C. for 30 minutes, and sterile filtered. A volume of 50 μl of the diluted, heat-inactivated sample is added to the microtiter plate wells containing the WEHI cells. Duplicate test samples are incubated in the presence of polyclonal rabbit anti-human TNF antiserum (Genzyme) or control rabbit serum (Life Technologies). Cells are incubated for 20 hours, after which time 20 μl of a 5 mg/ml stock solution of the tetrazolium salt 3-(4,5-dimethyl-thiazol-2-yl)-2,5-diphenyltetrazolium bromide (also called MTT or Thiazolyl blue; Sigma, Catalog Number M2128) in phosphate buffered saline (PBS) is added to each well. Following an additional 4 hours incubation, the plates are spun at 950×g for 10 minutes, the media from each well is aspirated, and 100 μl of 0.04N HCl/2-propanol is added to each well, and the plates are incubated overnight in the dark at room temperature. In the morning, an additional 100 μl of 0.04N HCl/2-propanol is added to each well and incubated for two hours in the dark at room temperature. Cell survival is then measured colorimetrically using a microplate reader with a 570 nm wavelength test filter and a 630 nm reference filter. Cell survival in each test well is determined as a percentage of the optical density of control wells. TNF-specific killing is defined as the difference in cell killing with or without the anti-TNF antiserim and is compared with standard curves produced with recombinant human TNF-α (R & D Systems).

EXAMPLE 15

Statistical Analysis

Data are presented as mean±standard error of the mean. Comparisons were made utilizing a paired two-tailed student's T test with a Bonneferoni correction for multiple comparisons. A P value<0.005 was considered significant.

These experiments demonstrate that expression of ARTS-1 protein directly correlates with and is necessary for soluble TNFR1 ectodomain shedding. Furthermore, ARTS-1 represents the first gene and protein which have been identified which have the ability regulate TNTFR1 ectodomain shedding. In addition, the present invention provides the nucleic acid and amino acid sequences of this gene and protein.

Furthermore, the compositions and methods of the present invention provide therapeutic applications for the treatment of a wide variety of disorders of the immune system which arise as a result of improper TNF activity.

All publications and patents mentioned in the above specification are herein incorporated by reference. Various modifications and variations of the described methods and compositions of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology and immunology and/or related fields are intended to be within the scope of the present invention.

What is claimed is:

1. A method for promoting the shedding of the extracellular domain of at least one cytokine receptor, comprising the steps of:
   a) providing:
      i) a polypeptide comprising the amino acid sequence set forth in SEQ ID NO: 2, and
      ii) one or more cells expressing a cytokine receptor on their plasma membrane extracellular surface, wherein the cytokine receptor is selected from the group consisting of a type-1 tumor necrosis factor receptor, a type I interleukin-1 cytokine receptor, a type II interleukin-1 cytokine receptor, and an interleukin-6 cytokine receptor alpha-chain gp80; and
   b) delivering said polypeptide to said one or more cells, whereby said polypeptide promotes the shedding of the cytokine receptor from the surface of said cells.

2. The method of claim 1, wherein said cytokine receptor is a type-1 tumor necrosis factor receptor.

3. The method of claim 1, wherein said cytokine receptor is a type I interleukin-1 cytokine receptor.

4. The method of claim 1, wherein said cytokine receptor is a type II interleukin-1 cytokine receptor.

5. The method of claim 1, wherein said cytokine receptor is an interleukin-6 cytokine receptor alpha-chain gp80.

6. The method of claim 1, wherein the one or more cells are cultured cells.

7. The method of claim 1, wherein the one or more cells are human cells.

8. The method of claim 2, wherein the one or more cells are human cells.

9. The method of claim 3, wherein the one or more cells are human cells.

10. The method of claim 4, wherein the one or more cells are human cells.

11. The method of claim 5, wherein the one or more cells are human cells.

12. The method of claim 1, wherein the one or more cells are in a tissue.

13. The method of claim 2, wherein the one or more cells are in a tissue.

14. The method of claim 3, wherein the one or more cells are in a tissue.

15. The method of claim 4, wherein the one or more cells are in a tissue.

16. The method of claim 5, wherein the one or more cells are in a tissue.

17. The method of claim 7, wherein the one or more cells are in a tissue.

* * * * *